US006153395A

United States Patent [19]
Gallatin et al.

[11] Patent Number: 6,153,395
[45] Date of Patent: Nov. 28, 2000

[54] ICAM-RELATED PROTEIN

[75] Inventors: W. Michael Gallatin; Rosemay Vazeux, both of Seattle, Wash.

[73] Assignee: ICOS Corporation, Bothell, Wash.

[21] Appl. No.: 08/296,749

[22] Filed: Aug. 26, 1994

Related U.S. Application Data

[60] Division of application No. 08/102,852, Aug. 5, 1993, abandoned, which is a continuation-in-part of application No. 08/009,266, Jan. 22, 1993, abandoned, which is a continuation-in-part of application No. PCT/US93/00787, Jan. 26, 1993, which is a continuation-in-part of application No. 07/894,061, Jun. 5, 1992, abandoned, which is a continuation-in-part of application No. 07/889,724, May 26, 1992, abandoned, which is a continuation-in-part of application No. 07/827,689, Jan. 27, 1992, abandoned.

[51] Int. Cl.$^7$ ................................................ G01N 33/566
[52] U.S. Cl. ........................... 435/7.24; 435/7.8; 436/501
[58] Field of Search ................................. 435/7.24, 7.8; 436/501

[56] References Cited

U.S. PATENT DOCUMENTS

| | | | |
|---|---|---|---|
| 3,654,090 | 4/1972 | Schurrs et al. | 436/518 |
| 5,081,034 | 1/1992 | Bevilacqua et al. | 435/252.33 |
| 5,318,890 | 6/1994 | Rosen et al. | 435/7.24 |
| 5,629,162 | 5/1997 | De Fougerolles et al. | 435/7.1 |

FOREIGN PATENT DOCUMENTS

| | | |
|---|---|---|
| 0 289 949 A2 | 11/1988 | European Pat. Off. |
| 0 314 317 A2 | 5/1989 | European Pat. Off. |
| 0 314 863 A2 | 5/1989 | European Pat. Off. |
| 0 362 531 A1 | 4/1990 | European Pat. Off. |
| 0 386 906 A1 | 9/1990 | European Pat. Off. |
| 0 387 668 A1 | 9/1990 | European Pat. Off. |
| 0 408 859 A2 | 1/1991 | European Pat. Off. |
| 0 468 257 A1 | 1/1992 | European Pat. Off. |
| WO 88/06592 | 9/1988 | WIPO. |
| WO 89/02922 | 4/1989 | WIPO. |
| WO 90/05539 | 5/1990 | WIPO. |
| WO 90/05786 | 5/1990 | WIPO. |
| WO 90/06953 | 6/1990 | WIPO. |
| WO 90/13300 | 11/1990 | WIPO. |
| WO 91/10683 | 7/1991 | WIPO. |
| WO 91/16928 | 11/1991 | WIPO. |
| WO 91/18010 | 11/1991 | WIPO. |
| WO 91/18011 | 11/1991 | WIPO. |
| WO 92/00751 | 1/1992 | WIPO. |
| WO 92/04034 | 3/1992 | WIPO. |
| WO 92/06119 | 4/1992 | WIPO. |
| WO 92/22323 | 12/1992 | WIPO. |

OTHER PUBLICATIONS

G. Bernard et al, *J. Immunol.*, 152(11), 5161–5170, 1994.

U.S. application No. 07/712,879, de Fougerolles et al., filed Jun. 11, 1991.

Ashkenazi et al., "Protection Against Endotoxic Shock by a Tumor Necrosis Factor Receptor Immunoadhesin", *Proc. Natl. Acad. Sci. USA*, 88:10535–10539 (1991).

Ballatyne et al., "Assignment of the Gene for Intercellular Adhesion Molecule 1 (Icam–1) to Proximal Mouse Chromosome 9", *Genomics*, 9:547–550 (1991).

Beatty et al., "Definition of a Common Leukocyte Cell–Surface Antigen (Lp95–150) Associated with Diverse Cell–Mediated Immune Functions[1]", *J. Immunol.*, 131:2913–2918 (1983).

Cannizzaro et al., "The Human Gene Encoding Phosphatidylinositol–3 Kinase Associated p85α Is at Chromosome Region 5q12–13[1]", *Cancer Res.*, 51:3818–3820 (1991).

Kapecchi, "Altering the Genome by Homologous Recombination", *Science*, 244:1288–1292 (1989).

Capon et al., "Designing CD4 Immunoadhesins for AIDS Therapy", *Nature*, 337:525–531 (1989).

Chen et al., "High Efficiency Transformation of Mammalian Cells by Plasmid DNA",*Molecular and Cellular Biology*, 7:2745–2752 (1987).

Corpet et al., "Multiple Sequence Alignment with Hierarchical Clustering", *Nucleic Acids Res.*, 16(22):10881–10890 (1988).

de Fougerolles et al., "Characterization of ICAM–2 and Evidence for a Third Counter–Receptor for LFA–1",*J. Exp. Med.*, 174:253–267 (1991).

de Fougerolles et al., "Cloning and Expression of Intercellular Adhesion Molecule 3 Reveals Strong Homology to Other Immunoglobulin Family Counterreceptors for Lymphocyte Function–associated Antigen 1", *J. Exp. Med.*, 177:1187–1192 (Apr. 1993).

Dustin et al., "Structure and Regulation of the Leukocyte Adhesion Receptor LFA–1 and Its Counterreceptors, ICAM–1 and ICAM–2", *CSH Symp. Qual.*, 54:753–765 (1989).

Dustin et al., "T–Cell Receptor Cross–Linking Transiently Stimulated Adhesiveness Through LFA–1", *Nature*, 341:619–624 (1989).

Edwards, "Cell Adhesion Molecules as a Target for Therapy", *Current Opinion in Therapeutic Patents*, 1(11):1617–1630 (1991).

Geppert et al., "Association of Various T Cell–Surface Molecules With The Cytoskeleton", *J. Immunol.*, 146:3298 (1990).

Goding, "Conjugation of Antibodies with Fluorochromes: Modifications to the Standard Methods", *J. Immunol. Meth.*, 13:215 (1976).

Hadam, "N11 Cluster Report: CDw50", pp. 667–670 in Knapp et al., eds., *Leukocyte Typing IV*, Oxford, Oxford University Press (1989).

(List continued on next page.)

*Primary Examiner*—David Saunders
*Attorney, Agent, or Firm*—Marshall, O'Toole, Gerstein, Murray & Borun

[57] ABSTRACT

DNA sequences encoding a novel human intercellular adhesion molecule polypeptide (designated "ICAM-R") and variants thereof are disclosed along with methods and materials for production of the same by recombinant procedures. Binding molecules specific for ICAM-R and variants thereof are also disclosed as useful in both the isolation of ICAM-R from natural cellular sources and the modulation of ligand/receptor binding biological activities of ICAM-R.

4 Claims, 33 Drawing Sheets

OTHER PUBLICATIONS

Hochuli et al., "Genetic Approach to Facilitate Purification of Recombinant Proteins With A Novel Chelate Adsorbent", *Bio/Technology*, 6:1321–1325 (1988).

Hunkapiller et al., "The Growing Immunoglobulin Gene Superfamily", *Nature*, 323:15–16 (1986).

Janknecht et al., "Rapid and Efficient Purification of Native Histidine–Tagged Protein Expressed by Recombinant Vaccinia Virus", *Proc. Natl. Acad. Sci.*, USA, 88:8972–8976 (1991).

Johnstone et al., p. 52 in Blackwell, *Immunochemistry in Practice*, Oxford Press (1982).

Knapp et al., "CD Antigens 1989", *Blood*, 74(4):1488–1450 (Sep. 1989).

Kunkel et al., "Rapid and Efficient Site–Specific Mutagenesis Without Phenotypic Selection", *Proc. Natl. Acad. Sci.* USA, 82:488–492 (1985).

Kyte et al., "A Simple Method for Displaying the Hydropathic Character of a Protein",*J. Mol. Biol.*, 157:105–132 (1982).

Ledbetter et al., "Antibodies to Tp67 and Tp44 Augment and Sustain Proliferative Responses to Activated T Cells", *J. Immunol.*, 135(4):2331–2336 (1985).

Lozano et al., "Effect of Protein Kinase C Activators on the Phosphorylation and the Surface Expression of the CDw50 Leukocyte Antigen", *Eur. J. Biochem.*, 203:321–326 (Mar. 1992).

Lozano et al., "Isolation and Characterisation of a CDw50 Negative Jurkat T–Cell Line Variant", *Leukemia Research*, 17(1):9–16 (1993).

Newman et al., "PECAM–1 (CD31) Cloning and Relation to Adhesion Molecules of the Immunoglobulin Gene Superfamily", *Science*, 247:1219–1222 (1990).

Pierschbacher and Ruoslahti, "Influence of Stereochemistry of the Sequence Arg–Gly–Asp–Xaa on Binding Specificity in Cell Adhesion", *J. Biol. Chem.*, 262(36):17294–17298 (1987).

Simmons et al., "ICAM, An Adhesion Ligand of LFA–1, Is Homologous to the Neural Cell Adhesion Molecule NCAM", *Nature*, 331:624–627 (1988).

Springer, "Adhesion Receptors of the Immune System", *Nature*, 346:425–434 (1990).

Staunton et al., "The Arrangement of the Immunoglobulin–like Domains of ICAM–1 and the Binding Sites for LFA–1 and Rhinovirus", *Cell*, 61:243–254 (1990).

Vilella et al., "Involvement of the CDw50 Molecule in Allorecognition", *Tissue Antigens*, 36:203–210 (1990).

Williams et al., "The Immunoglobulin Superfamily—Domains For Cell Surface Recognition [1,2]", *Ann. Rev. Immunol.*, 6:381–405 (1988).

DeFougerolles et al, Jour. Exper. Med., 175, 185–190, 1992.

Fawcett et al, Nature, 360, 481–484, 1992.

Jaun et al, Europ. Jour. Immunol. 23, 1508–1512, 1993.

Vazeux et al, Nature, 360, 485–488, 1992.

Yalow et al, In Odell et al (Eds.), Principles of Competitive Protein Binding Assays, J. B. Lippincott Company, 1971, pp. 1–6.

```
CAGCTCTCTGTCAGA ATG GCC ACC ATG GTA CCA TCC GTG TTG TGG CCC    48
                 M   A   T   M   V   P   S   V   L   W   P
                -29             -26 -25                  -20

AGG GCC TGC TGG ACT CTG CTG GTC TGC TGT CTG CTG ACC CCA GGT    93
 R   A   C   W   T   L   L   V   C   C   L   L   T   P   G
            -15                 -10                      -5

GTC CAG GGG CAG GAG TTC CTT TTG CGG GTG GAG CCC CAG AAC CCT   138
 V   Q   G │ Q   E   F   L   L   R   V   E   P   Q   N   P
        -1 │+1              5                       10

GTG CTC TCT GCT GGA GGG TCC CTG TTT GTG AAC TGC AGT ACT GAT   183
 V   L   S   A   G   G   S   L   F   V   N*  C   S   T   D
            15                  20                  25

TGT CCC AGC TCT GAG AAA ATC GCC TTG GAG ACG TCC CTA TCA AAG   228
 C   P   S   S   E   K   I   A   L   E   T   S   L   S   K
            30                  35                  40

GAG CTG GTG GCC AGT GGC ATG GGC TGG GCA GCC TTC AAT CTC AGC   273
 E   L   V   A   S   G   M   G   W   A   A   F   N*  L   S
            45                  50                  55
```

FIGURE 1A

```
AAC GTG ACT GGC AAC AGT CGG ATC CTC TGC TCA GTG TAC TGC AAT    318
 N*  V   T   G   N   S   R   I   L   C   S   V   Y   C   N*
G                   65              70
GGC TCC CAG ATA ACA GGC TCC TCT AAC ATC ACC GTG TAC GGG CTC    363
 G   S   Q   I   T   G   S   S   N*  I   T   V   Y   G   L
         75                  80              85
CCG GAG CGT GTG GAG CTG GCA CCC CTG CCT CCT TGG CAG CCG GTG    408
 P   E   R   V   E   L   A   P   L   P   P   W   Q   P   V
         90                  95             100
GGC CAG AAC TTC ACC CTG CGC TGC CAA GTG GAG GGT TCG CCC        453
 G   Q   N*  F   T   L   R   C   Q   V   E   G   S   P
        105                 110             115
CGG ACC AGC CTC ACG GTG GTG CTG CTT CGC TGG GAG GAG CTG        498
 R   T   S   L   T   V   V   L   L   R   W   E   E   L
        120                 125             130
CGG CAG CCC GCA GTG GAG GAG CCA GCG GAG GTC ACT GCC ACT        543
 S   R   Q   P   A   V   E   E   P   A   E   V   T   A   T
        135                 140             145
```

FIGURE 1B

```
GTG CTG GCC AGC AGA GAC CAC GGA GCC CCT TTC TCA TGC CGC      588
 V   L   A   S   R   D   D   H   G   A   P   F   S   C   R
             150                 155                 160

ACA GAA CTG GAC ATG CAG CCC CAG GGG CTG GGA CTG TTC GTG AAC   633
 T   E   L   D   M   Q   P   Q   G   L   G   L   F   V   N*
             165                 170                 175

ACC TCA GCC CCC CGC CAG CTC GTC CGA ACC TTT GTC CTG CCC ACC   678
 T   S   A   P   R   Q   L   R   T   F   V   L   P   V   T
             180                 185                 190

CCC CCG CGC CTC GTG GCC CCC CGG TTC TTG GAG GTG GAA ACG TCG   723
 P   P   R   L   V   A   P   R   F   L   E   V   E   T   S
             195                 200                 205

TGG CCG GTG GAC TGC ACC CTA GAC GGG CTT TTT CCA GCC TCA GAG   768
 W   P   V   D   C   T   L   D   G   L   F   P   A   S   E
             210                 215                 220

GCC CAG GTC TAC CTG GCG CTG GGG GAC CAG ATG CTG AAT GCG ACA   813
 A   Q   V   Y   L   A   L   G   D   Q   M   L   N*  A   T
             225                 230                 235
```

FIGURE 1C

```
GTC ATG AAC CAC GGG GAC ACG CTA ACG GCC ACA GCC ACG                858
 V   M   N   H   G   D   T   L   T   A   T   A   T
                     240                 245                 250

GCG CGC GCG GAT CAG GAG GGT GCC CGG GAG ATC GTC TGC AAC GTG        903
 A   R   A   D   Q   E   G   A   R   E   I   V   C   N*  V
             255                 260                 265

ACC CTA GGG GGC GAG AGA CGG GAG GCC CGG GAG AAC TTG ACG GTC        948
 T   L   G   G   E   R   R   E   A   R   E   N*  L   T   V
             270                 275                 280

TTT AGC TTC CTA GGA CCC ATT GTG AAC CTC AGC GAG CCC ACC GCC        993
 F   S   F   L   G   P   I   V   N*  L   S   E   P   T   A
             285                 290                 295

CAT GAG GGG TCC ACA GTG ACC GTG AGT TGC ATG GCT GGG GCT CGA       1038
 H   E   G   S   T   V   T   V   S   C   M   A   G   A   R
         300                 305                 310

GTC CAG GTC ACG CTG GAC GGA GTT CCG GCC GCG GCC CCG GGG CAG       1083
 V   Q   V   T   L   D   G   V   P   A   A   A   P   G   Q
         315                 320                 325
```

FIGURE 1D

```
CCA GCT CAA CTT CAG CTA AAT GCT ACC GAG AGT GAC GAC GGA CGC    1128
 P   A   Q   L   Q   L   N*  A   T   E   S   D   D   G   R
         330             335             340

AGC TTC TTC TGC AGT GCC ACT CTC GAG GTG GAC GGC GAG TTC TTG    1173
 S   F   F   C   S   A   T   L   E   V   D   G   E   F   L
         345             350             355

CAC AGG AAC AGT AGC GTC CAG CTG CGA GTC CTG TAT GGT CCC AAA    1218
 H   R   N*  S   S   V   Q   L   R   V   L   Y   G   P   K
         360             365             370

ATT GAC CGA GCC ACA TGC CCC CAG CAC TTG AAA TGG AAA GAT AAA    1263
 I   D   R   A   T   C   P   Q   H   L   K   W   K   D   K
         375             380             385

ACG AGA CAC GTC CTG CAG TGC CAA GCC AGG GGC AAC CCG TAC CCC    1308
 T   R   H   V   L   Q   C   Q   A   R   G   N   P   Y   P
         390             395             400

GAG CTG CGG TGT TTG AAG GAA GGC TCC AGC CGG GAG GTG CCG GTG    1353
 E   L   R   C   L   K   E   G   S   S   R   E   V   P   V
         405             410             415
```

FIGURE 1E

```
GGG ATC CCG TTC TTC GTC AAC GTA ACA CAT AAT GGT ACT TAT CAG         1398
 G   I   P   F   F   V   N*  V   T   H   N*  G   T   Y   Q
        420                 425                 430

TGC CAA GCG TCC AGC TCA CGA GGC AAA TAC ACC CTG GTC GTG GTG         1443
 C   Q   A   S   S   S   R   G   K   Y   T   L   V   V   V
        435                 440                 445

ATG GAC ATT GAG GCT GGG AGC TCC CAC TTT GTC CCC GTC TTC GTG         1488
 M   D   I   E   A   G   S   S   H   F---V---P---V---F---V
        450                 455                 460

GCG GTG TTA CTG ACC CTG GGC GTG GTG ACT ATC GTA CTG GCC TTA         1533
 A---V---L---L---T---L---G---V---V---T---I---V---L---A---L
        465                 470                 475

ATG TAC GTC TTC AGG GAG CAC CAA CGG AGC GGC AGT TAC CAT GTT         1578
 M---Y---V---F---R   E   H   Q   R   S   G   S   Y   H   V
        480                 485                 490

AGG GAG GAG AGC ACC TAT CTG CCC CTC ACG TCT ATG CAG CCG ACA         1623
 R   E   E   S   T   Y   L   P   L   T   S   M   Q   P   T
        495                 500                 505
```

FIGURE 1F

```
GAA GCA ATG GGG GAA GAA CCG TCC AGA GCT GAG TGACGCTGGGATCCG    1671
 E   A   M   G   E   E   P   S   R   A   E
        510             515             518

GGATCAAAGTTGGGCGGGGGGCTTGGGCTGTGCCCCTCAGATTCCGCACCAATAAAGCCTTCA    1730

AACTCCCAAAAAAAAAAAAAAAAAAAAAAAAAAAAAAAAAAAAAAAAAAA    1781
```

FIGURE 1G

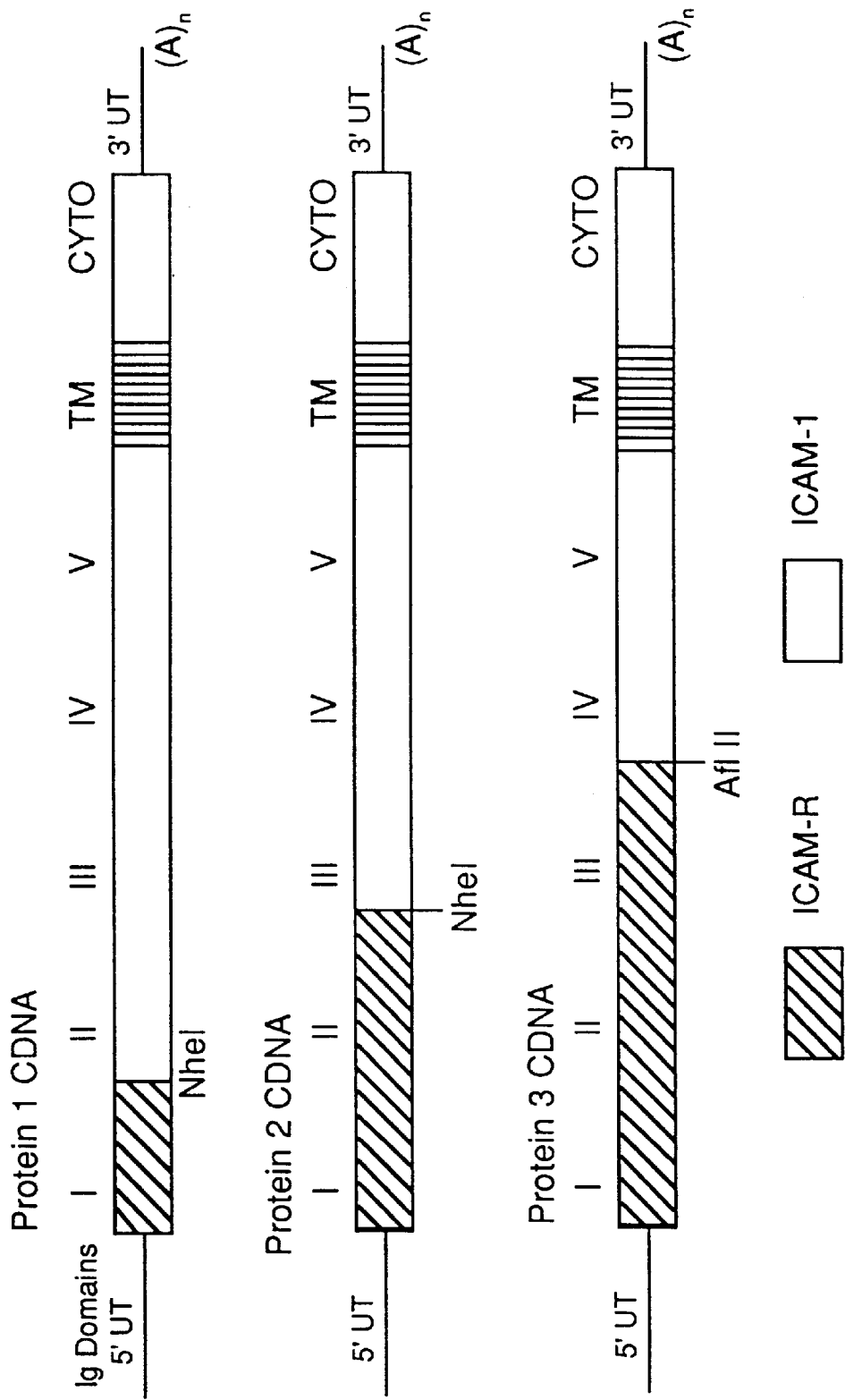

PRE-INCUBATION WITH IMMOBILIZED ICAM-R
SPECIFIC MONOCLONAL ANTIBODIES
INHIBITS STAPH ENTEROTOXIN
INDUCED LYMPHOCYTE PROLIFERATION

[Bar chart: Y-axis "COUNTS PER MINUTE ($\times 10^{-3}$)" 0 to 100; X-axis "PRE-INCUBATION TIME" with groups 3 HOURS, 5 HOURS, 7 HOURS, 72 HOURS]

▨ αHLA-1(γ1)
◩ αHLA-1(γ2)
▧ ICR-4.2
☐ ICR-1.1

FIGURE 12

ICAM-RELATED PROTEIN

This is a divisional of U.S. patent application Ser. No. 08/102,852, Filed Aug. 5, 1993 and now abandoned; which is a continuation-in-part of U.S. patent application Ser. No. 08/009,266, filed Jan. 22, 1993 and now abandoned, and International Application No. PCT/US93/00787, filed Jan 26, 1993; which are continuations-in-part of U.S. patent application Ser. No. 07/894,061, filed Jun. 5, 1992 and now abandoned; which is a continuation-in-part of U.S. application Ser. No. 07/889,724, filed May 26, 1992 and now abandoned; which is a continuation-in-part of U.S. application Ser. No. 07/827,689, filed Jan. 27, 1992 and now abandoned.

FIELD OF THE INVENTION

The present invention relates generally to cellular adhesion molecules and more particularly to the cloning and expression of DNA encoding a heretofore unknown human polypeptide designated "ICAM-R" which possesses structural relatedness to the intercellular adhesion molecules ICAM-1 and -2.

BACKGROUND OF THE INVENTION

Research spanning the last decade has significantly elucidated the molecular events attending cell-cell interactions in the body, especially those events involved in the movement and activation of cells in the immune system. See generally, Springer, *Nature*, 346: 425–434 (1990). Cell surface proteins, and especially the so-called Cellular Adhesion Molecules ("CAMS") have correspondingly been the subject of pharmaceutical research and development having as its goal intervention in the processes of leukocyte extravasation to sites of inflammation and leukocyte movement to distinct target tissues. The isolation and characterization of cellular adhesion molecules, the cloning and expression of DNA sequences encoding such molecules, and the development of therapeutic and diagnostic agents relevant to inflammatory processes, viral infection and cancer metastasis have also been the subject of numerous U.S. and foreign applications for Letters Patent. See Edwards, *Current Opinion in Therapeutic Patents*, 1(11): 1617–1630 (1991) and particularly the published "patent literature references" cited therein.

Of fundamental interest to the background of the present invention are the prior identification and characterization of certain mediators of cell adhesion events, the "leukointegrins," LFA-1, MAC-1 and gp 150.95 (referred to in WHO nomenclature as CD18/CD11a, CD18/CD11b, and CD18/CD11c, respectively) which form a subfamily of heterodimeric "integrin" cell surface proteins present on B lymphocytes, T lymphocytes monocytes and granulocytes. See, e.g., Table 1 of Springer, supra, at page 429. Also of interest are other single chain adhesion molecules (CAMs) that have been implicated in leukocyte activation, adhesion, motility and the like, which are events attendant the inflammatory process. For example, it is presently believed that prior to the leukocyte extravasation which characterizes inflammatory processes, activation of integrins constitutively expressed on leukocytes occurs and is followed by a tight ligand/receptor interaction between the integrins (e.g., LFA-1) and one or both of two distinct intercellular adhesion molecules (ICAMs) designated ICAM-1 and ICAM-2 which are expressed on blood vessel endothelial cell surfaces and on other leukocytes.

Like the other CAMs characterized to date, [e.g., vascular adhesion molecule (VCAM-1) as described in PCT WO 90/13300 published Nov. 15, 1990; and platelet endothelial cell adhesion molecule (PECAM-1) as described in Newman et al., *Science*, 247: 1219–1222 (1990) and PCT WO 91/10683 published Jul. 25, 1991], ICAM-1 and ICAM-2 are structurally homologous to other members of the immunoglobulin gene superfamily in that the extracellular portion of each is comprised of a series of domains sharing a similar carboxy terminal motif. A "typical" immunoglobulin-like domain contains a loop structure usually anchored by a disulfide bond between two cysteines at the extremity of each loop. ICAM-1 includes five immunoglobulin-like domains; ICAM-2, which differs from ICAM-1 in terms of cell distribution, includes two such domains; PECAM-1 includes six; VCAM includes six or seven, depending on splice variations, and so on. Moreover, CAMs typically include a hydrophobic "transmembrane" region believed to participate in orientation of the molecule at the cell surface and a carboxy terminal "cytoplasmic" region. Graphic models of the operative disposition of CAMs generally show the molecule anchored in the cell membrane at the transmembrane region with the cytoplasmic "tail" extending into the cell cytoplasm and one or more immunoglobulin-like loops extending outward from the cell surface.

A variety of therapeutic uses have been projected for intercellular adhesion molecules, including uses premised on the ability of ICAM-1 to bind human rhinovirus. European Patent Application 468 257 A published Jan. 29, 1992, for example, addresses the development of multimeric configurations and forms of ICAM-1 (including full length and truncated molecular forms) proposed to have enhanced ligand/receptor binding activity, especially in binding to viruses, lymphocyte associated antigens and pathogens such as *Plasmodium falciparum*.

In a like manner, a variety of uses have been projected for proteins immunologically related to intercellular adhesion molecules. WO91/16928, published Nov. 14, 1991, for example, addresses humanized chimeric anti-ICAM-1 antibodies and their use in treatment of specific and non-specific inflammation, viral infection and asthma. Anti-ICAM-1 antibodies and fragments thereof are described as useful in treatment of endotoxic shock in WO92/04034, published Mar. 19, 1992. Inhibition of ICAM-1 dependent inflammatory responses with anti-ICAM-1 anti-idiotypic antibodies and antibody fragments is addressed in WO92/06119, published Apr. 16, 1992.

Despite the fundamental insights into cell adhesion phenomena which have been gained by the identification and characterization of intercellular adhesion proteins such as ICAM-1 and lymphocyte interactive integrins such as LFA-1, the picture is far from complete. It is generally believed that numerous other proteins are involved in inflammatory processes and in targeted lymphocyte movement throughout the body. Quite recently, for example, Springer and his co-workers postulated the existence of a third counter-receptor for LFA-1 [de Fougerolles et al., *J. Exp. Med.*, 174: 253–267 (1991)] and subsequently reported success in immunoprecipitating a "third" ICAM ligand, designated "ICAM-3" [de Fougerolles, et al., *J. Exp. Med.*, 175: 185–190 (1992)]. This molecule was reported to bind soluble LFA-1 and to be highly expressed by resting lymphocytes, monocytes and neutrophils. Unlike ICAM-1 and ICAM-2, however, the new ligand was not found to be expressed by endothelial cells. The immunoprecipitated product was noted to display a molecular weight of about 124,000 and to be heavily glycosylated, as revealed by a drop in apparent molecular weight to about 87,000 upon N-glyanase treatment. More recently, another research group described a cDNA sequence for a counter-receptor for LFA-1 which was also designated "ICAM-3" [see Fawcett et al., Nature, 360: 481–484 (1992)]. Even more recently, two articles were published by Springer and his coworkers [de Fougerolles et al., J. Exp. Med., 177: 1187–1192 (1993) and Juan et al., Eur. J. Immunol., 23: 1508–1512 (1993)] which respectively report the amino acid sequence for ICAM-3 as being identical to that of ICAM-R and note the identity of ICAM-3 to the differentiation antigen CDw50 based on patterns of immunological reactivity of antibodies specific for each protein.

There thus continues to be a need in the art for the discovery of additional proteins participating in human cell-cell interactions and especially a need for information serving to specifically identify and characterize such proteins in terms of their amino acid sequence. Moreover, to the extent that such molecules might form the basis for the development of therapeutic and diagnostic agents, it is essential that the DNA encoding them be elucidated. Such seminal information would inter alia, provide for the large scale production of the proteins, allow for the identification of cells naturally producing them, and permit the preparation of antibody substances or other novel binding proteins specifically reactive therewith and/or inhibitory of ligand/receptor binding reactions in which they are involved.

BRIEF SUMMARY

In one of its aspects, the present invention provides purified and isolated polynucleotides (e.g., DNA sequences and RNA transcripts thereof) encoding a novel human polypeptide, "ICAM-R," as well as polypeptide variants (including fragments and analogs) thereof which display one or more ligand/receptor binding biological activities and/or immunological properties specific to ICAM-R. ICAM-R-specific ligand/receptor binding biological activities encompass interactions of both the ICAM-R extracellular and cytoplasmic domains with other molecules (e.g., in processes of cell-cell adhesion and/or signal transduction). Preferred DNA sequences of the invention include genomic and cDNA sequences as well as wholly or partially chemically synthesized DNA sequences. Biological replicas (i.e., copies of isolated DNA sequences made in vivo or in vitro) of DNA sequences of the invention are contemplated. Also provided are autonomously replicating recombinant constructions such as plasmid and viral DNA vectors incorporating ICAM-R sequences and especially vectors wherein DNA encoding ICAM-R or an ICAM-R variant is operatively linked to an endogenous or exogenous expression control DNA sequence.

According to another aspect of the invention, host cells, especially unicellular host cells such as procaryotic and eucaryotic cells, are stably transformed with DNA sequences of the invention in a manner allowing the desired polypeptides to be expressed therein. Host cells expressing such ICAM-R and ICAM-R variant products can serve a variety of useful purposes. To the extent that the expressed products are "displayed" on host cell surfaces, the cells may constitute a valuable immunogen for the development of antibody substances specifically immunoreactive with ICAM-R and ICAM-R variants. Host cells of the invention are conspicuously useful in methods for the large scale production of ICAM-R and ICAM-R variants wherein the cells are grown in a suitable culture medium and the desired polypeptide products are isolated from the cells or from the medium in which the cells are grown.

Novel ICAM-R and ICAM-R variant products of the invention may be obtained as isolates from natural cell sources, but are preferably produced by recombinant procedures involving host cells of the invention. The products may be obtained in fully or partially glycosylated, partially or wholly de-glycosylated, or non-glycosylated forms, depending on the host cell selected for recombinant production and/or post-isolation processing.

Products of the invention include monomeric and multimeric polypeptides having the sequence of amino acid residues numbered −29 through 518 as set out in SEQ ID NO: 1 herein. As explained in detail infra, this sequence includes a putative signal or leader sequence which precedes the "mature" protein sequence and spans residues −29 through −1, followed by the putative mature protein including, in order, five putative immunoglobulin-like domains (respectively spanning residues ~1 to 90, ~91 to 187, ~188 to 285, ~286 to 387, and ~388 to 456), a hydrophobic "transmembrane" region extending from about residue 457 to about residue 481 and a "cytoplasmic" region constituting the balance of the polypeptide at its carboxy terminus. Based on amino acid composition, the calculated molecular weight of the mature protein lacking glycosylation or other post-translational modification is approximately 52,417. ICAM-R variants of the invention may comprise water soluble or insoluble monomeric, multimeric or cyclic ICAM-R fragments which include all or part of one or more of the domain regions specified above and having a biological or immunological property of ICAM-R including, e.g., the ability to bind to a binding partner of ICAM-R and/or inhibit binding of ICAM-R to a natural binding partner. ICAM-R variants of the invention may also comprise polypeptide analogs wherein one or more of the specified amino acids is deleted or replaced: (1) without loss, and preferably with enhancement, of one or more biological activities or immunological characteristics specific for ICAM-R; or (2) with specific disablement of a particular ligand/receptor binding function. Analog polypeptides including additional amino acid (e.g., lysine or cysteine) residues that facilitate multimer formation are contemplated.

Also comprehended by the present invention are antibody substances (e.g., monoclonal and polyclonal antibodies, antibody fragments, single chain antibodies, chimeric antibodies, CDR-grafted antibodies and the like) and other binding proteins (e.g., polypeptides and peptides which are specific (i.e., non-reactive with the ICAM-1 and ICAM-2 intercellular adhesion molecules to which ICAM-R is structurally related) for ICAM-R or ICAM-R variants. Antibody substances can be developed using isolated natural or recombinant ICAM-R or ICAM-R variants or cells expressing such products on their surfaces. Specifically illustrating antibodies of the present invention are the monoclonal antibodies produced by the hybridoma cell lines designated 26E3D-1, 26I8F-2, 26I10E-2, 26H11C-2 which were deposited with the American Type Culture Collection (ATCC), 12301 Parklawn Drive, Rockville, Md. 20852, on Jun. 2, 1992 as Accession Nos. HB 11054, HB 11056, HB 11053, and HB 11055, respectively, in support of U.S. Ser. No. 07/894,061 (abandoned); the hybridoma cell line designated 43H7C which was deposited with the ATCC on Dec. 16, 1992 as Accession No. HB 11221 and the hybridoma cell lines designated 42C5H and 42D9B which were deposited with the ATCC on Jan. 15, 1993 as Accession Nos. HB 11235 and HB 11236, respectively, in support of U.S. Ser. No. 08/009,266 (abandoned); the hybridoma cell lines 46D7E and 46I12H which were deposited with the ATCC on Jan. 7, 1993 as Accession Nos. HB 11232 and HB 11231, respectively, also in support of U.S. Ser. No. 08/009,266 (abandoned); and the hybridoma cell lines 63E11D, 63G4D, 63H4C, 63H6H, 63I1C and 63I6G which were deposited with the ATCC on Jul. 15, 1993 as Accession Nos. HB 11405, HB 11409, HB 11408, HB 11407, HB 11406 and HB 11404, respectively, in support of this application. Various distinguishing properties of binding proteins of the invention are illustrated by these antibodies and are summarized in Table 11 of Example 21 herein. Such properties include the ability to modulate CD18-dependent and CD18-independent binding of ICAM-R to cells and cell surface molecules as well as the ability to modulate lymphocyte activation by SEA and/or alloantigen. Binding proteins of the invention are additionally susceptible to characterization in terms of binding site structure (e.g., epitopes and/or sensitivity of binding properties to modifications in ICAM-R amino acid sequence).

Binding proteins are useful, in turn, in compositions for immunization as well as for purifying polypeptides of the invention and identifying cells displaying the polypeptides on their surfaces. They are also manifestly useful in modulating (i.e., blocking, inhibiting or stimulating) ligand/receptor binding biological activities involving ICAM-R, especially those ICAM-R effector functions involved in specific and non-specific immune system responses. Anti-idiotypic antibodies specific for anti-ICAM-R antibody substances and uses of such anti-idiotypic antibody substances in modulating immune responses are also contemplated. Assays for the detection and quantification of ICAM-R on cell surfaces and in fluids such as serum may involve, for example, a single antibody substance or multiple antibody substances in a "sandwich" assay format.

The scientific value of the information contributed through the disclosures of DNA and amino acid sequences of the present invention is manifest. As one series of examples, knowledge of the sequence of a cDNA for ICAM-R makes possible the isolation by DNA/DNA hybridization of genomic DNA sequences encoding ICAM-R and specifying ICAM-R expression control regulatory sequences such as promoters, operators and the like. DNA/DNA hybridization procedures carried out with DNA sequences of the invention and under stringent conditions are likewise expected to allow the isolation of DNAs encoding allelic variants of ICAM-R, other structurally related proteins sharing one or more of the biological and/or immunological properties specific to ICAM-R, and non-human species proteins (e.g., rodent) homologous to ICAM-R. DNAs of the invention are useful in DNA/RNA hybridization assays to detect the capacity of cells to synthesize ICAM-R. Also made available by the invention are antisense polynucleotides relevant to regulating expression of ICAM-R by those cells which ordinarily express the same. As another series of examples, knowledge of the DNA and amino acid sequences of ICAM-R makes possible the generation by recombinant means of ICAM-R variants such as hybrid fusion proteins (sometimes referred to as "immunoadhesions") characterized by the presence of ICAM-R protein sequences and immunoglobulin heavy chain constant regions and/or hinge regions. See, Capon et al., *Nature*, 337: 525–531 (1989); Ashkenazi et al., *P.N.A.S.* (*USA*), 88: 10535–10539 (1991); and PCT WO 89/02922, published Apr. 6, 1989. ICAM-R variant fusion proteins may also include, for example, selected extracellular domains of ICAM-R and portions of other cell adhesion molecules.

The DNA and amino acid sequence information provided by the present invention also makes possible the systematic analysis of the structure and function of ICAM-R and definition of those molecules with which it will interact on extracellular and intracellular levels. The idiotypes of anti-ICAM-R monoclonal antibodies of the invention are representative of such molecules and may mimic natural binding proteins (peptides and polypeptides) through which ICAM-R intercellular and intracellular activities are modulated or by which ICAM-R modulates intercellular and intracellular events. Alternately, they may represent new classes of modulators of ICAM-R activities. Anti-idiotypic antibodies, in turn, may represent new classes of biologically active ICAM-R equivalents. In vitro assays for identifying antibodies or other compounds that modulate the activity of ICAM-R may involve, for example, immobilizing ICAM-R or a natural ligand to which ICAM-R binds, detectably labelling the nonimmobilized binding partner, incubating the binding partners together and determining the effect of a test compound on the amount of label bound wherein a reduction in the label bound in the presence of the test compound compared to the amount of label bound in the absence of the test compound indicates that the test agent is an inhibitor of ICAM-R binding. The DNA sequence information provided by the present invention also makes possible the development, by homologous recombination or "knockout" strategies [see, e.g., Kapecchi, *Science*, 244: 1288–1292 (1989)], of rodents that fail to express a functional ICAM-R protein or that express a variant ICAM-R protein. Such rodents are useful as models for studying the activities of ICAM-R and ICAM-R modulators in vivo.

BRIEF DESCRIPTION OF THE DRAWING

Numerous other aspects and advantages of the present invention will be apparent upon consideration of the following detailed description thereof, reference being made to the drawing wherein:

FIG. 1(A through G) depicts an isolated cDNA clone insert (SEQ ID NO: 2) derived from HL60 cells encoding ICAM-R and the deduced amino acid sequence (SEQ ID NO: 1) of an open reading frame therein;

FIG. 6 is a diagram of three chimeric ICAM-R proteins utilized to map epitopes of anti-ICAM-R monoclonal antibodies of the invention;

FIG. 11(A through B) comprises bar graphs illustrating the effects of anti-ICAM-R monoclonal antibodies on superantigen-induced proliferation of human peripheral blood lymphocytes, while

FIG. 12 is a bar graph depicting the effects of anti-ICAM-R monoclonal antibodies on alloantigen-induced T-cell proliferation.

DETAILED DESCRIPTION

Figure 2A:
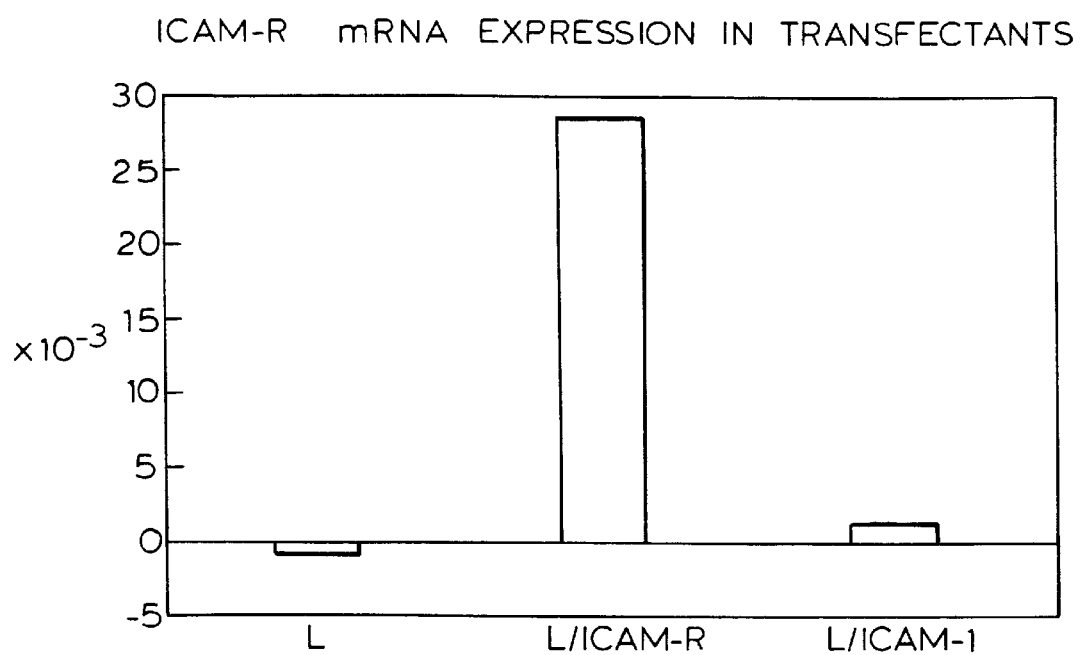
FIG. 2(A through B) comprises bar graphs illustrating the results of Northern blot hybridization of transfected L cells using ICAM-R and ICAM-1 DNA probes.

The present invention is illustrated by the following examples relating to the isolation of a full length cDNA clone encoding ICAM-R from a cDNA library derived from human HL60 promyelocytic cells (ATCC CCL 240) and to the expression of ICAM-R DNA in L cells. More particularly, Example 1 addresses the design and construction of oligonucleotide probes for PCR amplification of ICAM related DNAs. Example 2 addresses the use of the probes to amplify a genomic DNA fragment homologous to, but distinct from, DNAs encoding ICAM-1 and ICAM-2. Example 3 treats the screening of cDNA libraries with the genomic fragment to isolate additional ICAM-R coding sequences. Example 4 refers to the further screening of cDNA libraries to isolate a full length human cDNA encoding ICAM-R. Example 5 provides a characterization of DNA and amino acid sequence information for ICAM-R and relates the structures thereof to ICAM-1 and ICAM-2. Example 6 describes the isolation of DNA sequences encoding rodent homologues of ICAM-R. Example 7 relates to the development of mammalian host cells expressing ICAM-R. Example 8 describes preliminary experiments indicative of ICAM-R participation in intercellular adhesion events involving CD18-dependent and CD18-idependent pathways. Example 9 presents experiments illustrating inhibition of cell adhesion to ICAM-R by ICAM-R derived peptides. Example 10 describes the construction and expression of a panel of rodent ICAM-R/glutathione S-transferase fusion proteins. Example 11 relates to the construction and expression of a soluble variant of ICAM-R. Example 12 describes the construction and expression of ICAM-R variants having point mutations in their extracellular domains. Example 13 describes the preparation and preliminary characterization of anti-ICAM-R antibodies and the preparation of Fab' fragments thereof. Example 14 relates to mapping of the ICAM-R epitopes recognized by the anti-ICAM-R monoclonal antibodies of the invention. Examples 15, 16 and 17 relate to assessment of the distribution and biochemical characterization of ICAM-R polypeptide and RNA encoding the same in normal cells and tissues as well as in various cell lines. Example 19 describes assays for the involvement of ICAM-R in homotypic cell-cell adhesion. Example 20 addresses experiments indicating that ICAM-R is involved in immune cell activation/proliferation. Example 21 comprises a summary of characteristics of ICAM-R specific monoclonal antibodies of the invention. Example 22 describes experiments showing differential phosphorylation of and cytoskeletal associations with the cytoplasmic domain of ICAM-R.

EXAMPLE 1

Nucleic acid and amino acid alignments of individual sets of CAMs (e.g., ICAM-1 and ICAM-2) did not manifest sufficient conservation between molecules to yield information useful in the design of consensus-type probes for isolating related novel genes. The strategic focus of attempts to isolate unknown DNAs encoding cellular adhesion molecules therefore involved the development of degenerate consensus oligonucleotides representing putative spaced apart DNA sequences of various known molecules and the use of these oligonucleotides as primers for polymerase chain reaction (PCR) amplification of DNA replicas of intermediate gene sequences which resemble, but are not identical to, the known DNAs. The starting point for oligonucleotide primer design was the notation that the amino acids in regions surrounding cysteines which form immunoglobulin-like loops of certain CAMs are somewhat conserved. At the amino terminal side of the motif, the sequence:

SEQ ID NO: 3

G—X—X—(V or L or I)—X—(V or L or I)—X—C is found, while at the carboxy terminal side of the motif, the sequence:

SEQ ID NO: 4

N—X—G—X—Y—X—C—X—V or A)

is typical. [See Hunkapiller et al., *Nature*, 323: 15–16 (1986); Williams et al, *Ann. Rev. Immunol.*, 6: 381–405 (1988); and Newman et al, supra.] In and of themselves the two amino acid motifs are much too general and do not allow the construction of degenerate sets of oligonucleotides useful as probes for unknown DNAs which might share the motif. In an attempt to solve this problem, each individual CAM sequence was split into a domain of sub files defined by the cysteine motif termini described above. Subfiles were generated for each of the seven domains of human vascular adhesion molecule (VCAM-1), the six domains of human platelet endothelial cell adhesion molecule (PECAM-1), the five domains of ICAM-1, the two domains of ICAM-2, three of the four domains of both human myeloglobin-related glycoprotein and human fibroblast growth factor receptor, and the five domains of mouse neural cell adhesion molecule (NCAM). All the subfiles were pooled and segregated independently from the CAM of origin using a multialignment homology computer algorithm designated "Multalin" [Corpet, *Nucleic Acids Research*, 16(22): 10881–10890 (1988)] providing a tree of alignment allowing the ascertainment of consensus sequences around cysteine motifs. A consensus sequence representing the amino terminal cysteine motif was determined to be:

SEQ ID NO: 5

G—K—(N or S)—(L or F)—T—(L or I)—(R or E)—C while the carboxy terminal consensus sequence was determined to be:

SEQ ID NO: 6

(D or E)—(H or D)—(H or G)—(G or H)—(A or R)—N—F—S—C.

Employing human preferences for codon usage to partially eliminate degeneracy, three separate sets of degenerate oligonucleotides totalling 1152 probes were generated for use as top strand PCR primers for amplification from a putative amino terminus of the motif. The specific degenerate sequences of the three pools are set out below in IUPAC nomenclature.

SEQ ID NO: 7

ATTCTGCAGGCAARAAYCTSACHMTBMGSTG

SEQ ID NO: 8

ATTCTGCAGGCAARAGYTTYACHMTBGARTG

SEQ ID NO: 9

ATTCTGCAGGCAARTCYTTYACHMTBGARTG

Each of the primers included a PstI restriction endonuclease recognition site (CTGCAG) to facilitate cloning of amplified products.

A total of 768 probes were designed as bottom strand primers as set out below in IUPAC nomenclature for amplification from a putative carboxy terminus of the motif. Each of these primers included an XbaI recognition site (TCTAGA) to facilitate cloning of amplified products.

SEQ ID NO: 10

ATTTCTAGARAARTTRGCSCCRTGRTSRTC

SEQ ID NO: 11

ATTTCTAGARAARTTSCKRTGSCCRTSKTC

Oligonucleotides were synthesized with an automated Applied Biosystems, Inc. (Foster City, Calif.) Model 394 DNA synthesizer using an 0.2 micromolar scale synthesis program and employing beta-cyanoethyl chemistry. Protective groups were then removed by heating at 55° C. for in excess of six hours. Oligonucleotides were then lyophilized to dryness, rehydrated in TE (10 mM Tris, pH 7.0, 1 mm EDTA) and desalted in TE by size exclusion chromatography with G25-150 Sephadex.

EXAMPLE 2

The two sets of probes whose design and synthesis are described in Example 1 were employed in PCR amplification procedures applied to a human genomic DNA template. Briefly put, PCR-generated fragments of a size similar to that of the immunoglobulin-like loop regions of ICAM-1 and ICAM-2 were isolated, subcloned into Bluescript plasmid (Stratagene, La Jolla, Calif.) and screened both directly by sequencing and hybridization in arrays for homology to ICAM-2 DNA. Approximately 50% of the fragments were identical to ICAM-1 or ICAM-2 (except, of course, in the regions of the degenerate primer). One subclone, designated 13-3C7, was found to have an open reading frame homologous to ICAM-1 and ICAM-2 in the region of their respective second domains. It did not correspond to any known sequence present in the Genbank data base. The specific manipulations leading up to the isolation of subclone 13-3C7 were as follows.

The degenerate oligonucleotides were mixed to a final concentration of 10 μg/ml in a PCR reaction to amplify human genomic DNA obtained either from peripheral blood leukocytes or Hela cells. The DNA amplification was performed in PCR buffer (2 mM $MgCl_2$, 25 mM KCl, 10 mM Tris pH 8.3) with 2 mM deoxynucleotides. After a 94° C. denaturation for 4 minutes, 30 PCR cycles were performed with annealing at 60° C. for 2 minutes, elongation at 72° C. for 4 minutes and denaturation at 94° C. for 1 minute. A DNA band migrating at about 0.2 kb was extracted from a 6% polyacrylamide gel by electroelution, digested by XBaI and Pst 1 restriction enzymes, and ligated into the Bluescript vector (Stratagene). The plasmid was electroporated into XL 1-blue strains of E. coli (Stratagene) and colonies were selected on X-gal IPTG, carbenicillin agarose plates. Single strand templates were obtained from 6 white colonies after addition of M13K07 helper phage (Stratagene), carbenicillin, and kanamycin to a 2 ml culture of each colony. For sequence analysis, the single strand templates were then sequenced using the Sanger method both by DNA automatic sequencing (Applied Biosystems) and with a sequenase kit (UCB, Belgium). Four sequences (clones 1.1, 1.3, 1.4, 1.6) were obtained which were 184–185 base pairs (bp) long and were 92–95% homologous to the second domain of ICAM-2. In addition, a 182 bp long DNA sequence (clone 1.5) was obtained which contained a frameshift in the open reading frame of an ICAM-1-like domain along with a 66 bp DNA (clone 1.2) corresponding to a truncated immunoglobulin-like domain.

The sequence of clones 1.6, 1.5, 1.2 was used to design three oligonucleotide probes (RM16, RM15, RM12) that were used in subsequent tests to eliminate from further consideration additional colonies containing cDNAs that were highly homologous to the previous isolated clones. The sequences of probes RM16, RM15 and RM12 are set out below.

Probe RM16 (SEQ ID NO: 12)

GAGACTCTGCACTATGAGACCTTCG

Probe RM15 (SEQ ID NO: 13)

CAGGTGATTCTCATGCAGAGTCCAGG

Probe RM12 (SEQ ID NO: 14)

CCGACATGCTGGTAAGTGTGTCCAA

In a second round of tests, new colonies were obtained from the original PCR products that had been XbaI and Pst 1 digested and from additional PCR products that had been rendered blunt-ended by treatment with the Klenow fragment of polymerase I and subcloned by blunt-end ligation. The colonies containing the vector with an insert were selected on carbenicillin L broth agarose plates containing X-gal and IPTG. Single strand templates were then synthesized in 96-well plates by growing individual white colonies in 300 μl L broth, to which was added M13K07 phage, carbenicillin and kanamycin. Ten μl of each template was transferred with a pronging device to a nylon membrane, denatured and fixed with UV light. (Ten μl of each template were transferred to three different nylon membranes for each 9-well plate.) Oligonucleotides RM16, RM15, RM12 were labelled by phosphorylation using [λ-$^{32}$P]ATP. The nylon membranes were pre-hybridized in 20% formamide, 5×SSC, 5×Denhardt's solution and 0.5% SDS for 3 hours at 42° C. then hybridized overnight with the different radiolabelled oligonucleotide probes under the same conditions. The membranes were then washed in 0.2×SSC, 0.5% SDS three times for 15 minutes each at room temperature then washed in the same buffer at 37° C. for 15 minutes, rinsed in 2×SSC and exposed. Each template that did not hybridize with either of the three oligonucleotide probes was further sequenced using the Sanger technique by DNA automatic sequencing and by sequenase kit. Using this technique, the 170 bp DNA sequence of a clone designated 13-3C7 was determined.

EXAMPLE 3

The cDNA insert of subclone 13-3C7 isolated in Example 2 was used as a hybridization probe to screen four different lambda phage cDNA libraries prepared from human spleen, human placenta (two libraries) and human leukocyte cell line U937 (ATCC CRL 1593). Briefly summarized, one hundred and twenty positive clones were picked (from among the approximately 1.6 million clones screened), subcloned, rescreened with the 13-3C7 probe, and the rescreening positive were size selected for inserts of greater than approximately 500 bp by analytical PCR with primers corresponding to the plasmid DNA flanking the insertion for DNAs. A 1.3 kb clone derived from U937 cDNA, designated clone 19C, was sequenced and revealed DNA regions encoding two immunoglobulin-like domains separated by what appeared to be an intervening sequence (intron) resulting from improper or incomplete mRNA splicing prior to cDNA formation. The two regions displayed significant homology, but overall distinctness, in comparison to domains 2 and 3 of ICAM-1 and less homology to domains 1 and 2 of ICAM-2.

The specific procedures leading up to isolation of clone 19C were as follows. The four libraries were constructed in lambda gt10 phage (λgt10) using cDNA obtained from the U937 cell line, from the spleen of a patient with chronic myelomonocytic leukemia and from human placenta. Exact match oligonucleotides designated 1 Hr-5' and 1Hr-3' were designed corresponding to the 5' and 3' sides of the domain-like region of subclone 13-3C7 (including bases attributable to incorporation of the original degenerate primer). The sequences of the 1 Hr-5' and 1 Hr-3' oligonucleotide primers are set out below.

Primer 1 Hr-5' (SEQ ID NO: 15)
GACCATGAGGTGCCAAG
Primer 1 Hr-3' (SEQ ID NO: 16)
ATGGTCGTCTCTGCTGG Using these oligonucleotides in a PCR reaction with the 13-3C7 insert template and $^{32}$P-dCTP, a 148 bp long DNA probe was generated. The cDNA libraries were plated and transferred to nylon membranes. The membranes were pre-hybridized in 40% formamide, 5×SSC, 5×Denhardt's, 0.5% SDS at 42° C. for at least 15 minutes, then hybridized overnight with the probe in the same buffer at 42° C. The membranes were washed several times at room temperature in 2×SSC and exposed. Most of the phage plaques that hybridized with the probe were derived from the U937 cDNA library. These phages were further purified and tested by PCR (using 1 Hr-5' and 1 Hr-3' as primers) for the presence of the domain inside the cDNA clones. The phage were also tested by PCR to determine the length of the clones and the location of the domain within the cDNA fragment (using a combination of 13-3C7 specific primers and primers homologous to flanking λgt10 vector sequences). Two clones were selected. Clone 1F was 0.7 kb long and clone 19C was 1.3 kb long. These cDNAs were digested with EcoRI and subcloned in the Bluescript vector. In addition, the largest cDNA (clone 19C) was sonicated to obtain small pieces which were sub-cloned into Bluescript for sequencing. By homology with the ICAM-1 molecule, clone 19C cDNA contains 2 regions having homology to domains 2 and 3 of ICAM-1, respectively, with an intervening sequence of unrelated DNA. Hereinafter, these DNA regions are referred to as domains 2 and 3 of ICAM-R.

EXAMPLE 4

The 1.3 kb (clone 19C) DNA isolated in Example 3 and having regions encoding immunoglobulin-like loops resembling domains 2 and 3 of ICAM-1 was then employed to generate a probe for the screening of additional cDNA libraries in an attempt to isolate a full length cDNA clone. Briefly, the domain 2 and 3 regions within clone 19C were each amplified by PCR using unique probes designated to match respective amino (5') and carboxy (3') terminal portions of the domains. These amplified DNAs, in turn, provided probes for screening of cDNA libraries derived from: (1) the HL60 myelomonocytic cell line; (2) lipopolysaccharide-activated human monocytes; (3) HUT-78 T-cells (ATCC T1B161); and (4) activated peripheral blood leukocytes. The latter two libraries yielded no positive upon rescreening. Positives derived from HL60 and monocyte cDNA libraries were then screened with a probe representing domain 2 of ICAM-1 DNA (GenBank, Accession No. 22634) in order to eliminate ICAM-1 clones. A single phagmid clone derived from lambda 345 and designated pVZ-147, repeatedly tested positive for hybridization with the probe(s) based on the DNA isolated in Example 4 and negative for hybridization with the ICAM-1 DNA probe. The approximately 1.7 kb insert from clone pVZ-147 was isolated and sequenced to provide the 1781 bp sequence set out in SEQ ID NO: 2. The deduced amino acid sequence of the polypeptide encoded by this DNA is set out in SEQ ID NO: 1. The polypeptide was designated "ICAM-R" on the basis of its structural relatedness to ICAM-1 and ICAM-2. The DNA and deduced amino acid sequences of ICAM-R were published after the priority dates of this application in Vazeux et al., *Nature*, 360: 485–488 (1992). The open reading frame of the DNA sequence of ICAM-3 published after the priority dates of this application in Fawcett et al., supra, differs at two nucleotide positions from the coding region of the DNA sequence of ICAM-R presented in FIG. 1(A through G) herein. (See nucleotide positions 194 and 1275.)

The specific manipulations involved in the isolation of lambda phage clone pVZ147 are as follows. All cDNA libraries were constructed in λgt10 except for the HL60 library which cloned into phage lambda 345. Oligonucleotides for use in library screening and rescreening had the following sequences.

Probe IHr2-5' (SEQ ID NO: 17)
TTCACCCTGCGCTGCCAA
Probe IHr2-3' (SEQ ID NO: 18)
AAAGGGGCTCCGTGGTCG
Probe IHr 3-5' (SEQ ID NO: 19)
CCGGTTCTTGGAGGTGGAA
Probe IHr 3-3' (SEQ ID NO: 20)
CATGACTGTCGCATTCAGCA
Probe Icam 1-5 (SEQ ID NO: 21)
GCAAGAACCTTACCCTAC
Probe Icam 1-3 (SEQ ID NO: 22)
GAAATTGGCTCCATGGTGA Probes IHr 2-5' and IHr 2-3' were employed in a PCR amplification using $^{32}$P-dCTP on the clone 19C template to generate a domain 2 specific probe for cDNA screening. Likewise, probes IHr 3-5' and IHr 3-3' were employed to generate a domain 3 specific probe. Finally, probes Icam 1-5 and Icam 1-3 were employed to amplify an ICAM-1 segment probe corresponding to bases 440 through 609 of the ICAM-1 cDNA sequence (GenBank, Accession No. 22634), i.e., the ICAM-1 second domain.

The cDNA libraries were plated, transferred on nylon membranes, hybridized with the domain 2 probe (derived from clone 19C) in 40% formamide, 5×SSC, 5×Denhardt, 0.5% SDS and washed as described above. All the plaques that hybridized with the domain 2 probe were derived from the monocyte and HL60 libraries. These phage plaques were purified by dilution, plating, transfer and hybridization with the domain 2 probe. To further characterize the cDNA clones, each plaque that had hybridized with the domain 2 probe was grown on an array in triplicate, transferred to a nylon membrane and hybridized under higher stringency conditions (50% formamide, 5×SSC, 5×Denhardt, 0.5% SDS) with three different probes: the domain 2 probe; the domain 3 probe, and the ICAM-1 second domain probe. Five clones were found in the HL60 library and 2 clones in the monocyte library which hybridized with both domain 2 and domain 3 probes and not with the ICAM-1 second domain probe. A sixth clone from the HL60 library hybridized only with domain 2 probe and did not hybridize with either domain 3 or with ICAM-1 second domain. The cDNAs of the 6 clones from the HL60 library were further analyzed. The phages were tested by PCR for the presence of properly spliced cDNA using oligonucleotide primers corresponding to the 5' extremity (IHr2-5') of domain 2 and to the 3' extremity (IHr3-3') of domain 3. The clones were also tested by PCR for length and location of the domains inside the clones. The cDNA plasmids were extracted and cyclized from phage lambda 345 by digestion with SfiI and self-ligation. To facilitate making single strand templates and sequencing in both orientations, each cDNA was also subcloned in Bluescript SK+ vector (Stragene). Plasmid pVZ147 was determined to include the entire ICAM-R coding sequence in a single open reading frame.

EXAMPLE 5

A. Characterization of the ICAM-R Polypeptide

FIG. 1(A through G) graphically illustrates the sequence of the human cDNA insert of the lambda phage clone pVZ 147 isolated in Example 4, above. The total of 1781 bp shown are as set out in SEQ ID NO: 2. The deduced amino acid sequence of the ICAM-R polypeptide as set out in SEQ ID NO: 1 is graphically subdivided in FIG. 1(A through G) into the following regions:

(1) A putative signal or leader sequence is illustrated preceding the sequence of the "mature" protein and spanning amino acids designated −29 through −1. Determination of whether the translation product is actually initiated at −29 or −26 will be provided by amino acid sequencing of intercellular expression products. The designation of the first residue of the mature protein was based on generalized analogy to amino acids (and corresponding bases) for residues of secreted human proteins in the region of the junction of the mature protein and leader sequences. Confirmation of the actual initial residue of the mature protein awaits sequencing of a secreted recombinant product or, e.g., an immunopurified natural product.

(2) Within the mature protein spanning residues +1 through 518, five putative immunoglobulin-like loop regions are shown (white on black) bounded by cysteines within the five putative immunoglobulin-like domains (shown in boxes). Note that in the first domain (residues 1 through 91), cysteine residues potentially significant to loop formation are present at positions 24, 28, 67 and 71. Each of the remaining putative loops has a single relevant cysteine at each of its ends.

(3) Also within the mature protein, a putative hydrophobic "transmembrane" region is illustrated with dashes connecting residues 457 through 481 which follow the fifth immunoglobulin-like domain. A putative carboxy terminal "cytoplasmic" region constitutes residues 482 through 518.

(4) Potential N-linked glycosylation sites [characterized by the consensus sequence, Asparagine-X-(Serine or Threonine)] are indicated with an asterisk. Potential O-linked glycosylation sites occur at any serine or threonine residue.

A comparison was made between the amino acid sequence (SEQ ID NO: 1) of ICAM-R and the published 537 residue amino acid sequence of ICAM-1 (GenBank Accession No. 22634; cf, FIG. 8 of European Patent Application 0 289 949 published Nov. 11, 1988). This comparison revealed 249 matches within the aligned 537 residues, indicating an overall amino acid identity of 48% between the two polypeptides. The highest percentage of matches was noted to be present between domains 2 and 3 of ICAM-1 and putative domains 2 and 3 of ICAM-R. Likewise the alignment of SEQ ID NO: 1 with the published 295 residues of the amino acid sequence of ICAM-2 (GenEank accession No. 22635; cf, FIG. 2 of European Patent Application 0 387 668 published Sep. 19, 1990) revealed 78 matches among the 282 aligned residues, for a 27% overall identity of amino acids in one possible alignment. The cytoplasmic domain of ICAM-R was found to be 20% identical to the cytoplasmic domain of ICAM-1 and 34% identical to the cytoplasmic domain of ICAM-2 in one possible alignment.

B. Characterization of ICAM-R DNA

A comparative alignment of the human ICAM-R DNA sequence (SEQ ID NO: 2) was made with the published DNA sequences of ICAM-1 and ICAM-2, supra. A total of 677 matches were noted among the 1623 aligned bases of ICAM-R and ICAM-1 providing an overall identity of 41%. A 42% identity (484 matches) between the aligned 1136 bases of ICAM-R and ICAM-2 DNAs was noted.

Reference points in the FIG. 1(A through G) DNA having "historical" significance. to the isolation of the ICAM-R gene include the following:

(a) bases 420 through 567 correspond to the subclone 13-3C7 isolated in Example 2;

(b) bases 373 through 663 correspond to the immunoglobulin-like domain 2 localized in clone 19C of Example 3 (with bases 418 through 435 and 561 through 578, respectively corresponding to probes IHr2-5' and IHr2-3' employed for PCR amplification of domain 2 to provide one of the oligonucleotide probes for use in Example 4); and (c) bases 664 through 957 correspond to the immunoglobulin-like domain 3 localized on clone 19C of Example 3 (with bases 699 through 717 and 800 through 819, respectively corresponding to probes IHr3-5' and IHr3-3' employed for PCR amplification of domain 3 to provide another oligonucleotide probe for use in Example 4.

C. Chromosomal Localization of Sequences Encoding Human ICAM-R

An ICAM-R specific DNA probe was utilized in the methods described in Cannizzaro et al., *Cancer Res.*, 51: 3818–3820 (1991) to determine that the human ICAM-R encoding sequences are located on chromosome 19 with primary localization to the short (p) arm region.

EXAMPLE 6

DNA sequences encoding rodent homologues of human ICAM-R were isolated by low stringency hybridization using ICAM-R specific probes. Such DNAs can be employed in homologous recombination or "knockout" strategies to develop strains of rodents which lack ICAM-R expression. Additionally, the rodent ICAM-R DNA clones can be used to produce recombinant rodent ICAM-R protein useful in the development of agents (e.g., monoclonal antibodies) that can be tested in rodent models for modulation of the activities of ICAM-R in vivo.

A. Isolation of a Rat Genomic ICAM-R Domain 2 Clone

Adult Balb/c mouse PBL cDNA and rat PBC cDNA λ phage libraries (Clonetech, La Jolla, Calif.) and λ phage rat genomic DNA libraries made from rat liver DNA and C6VL lymphoblastoid cell DNA were screened with the full length human ICAM-R gene or fragments thereof. Library plaques were transferred to Hybond N+ nylon membranes (Amersham Corp., Arlington Heights, Ill.). All prehybridizations and hybridizations were carried out in a solution of 40–50% formamide, 5×Denhardt's, 5×SSPE and 1.0% SDS at 42° C. $^{32}$P-radiolabelled probes were added at a concentration of $10^5$–$10^6$ cpm/ml of hybridization solution. Following hybridization, filters were washed extensively at room temperature in 2×SSPE/0.1% SDS and then exposed to X-ray film. Positive clones were plaque purified in another round of hybridization. Lambda DNA was prepared from lysates of each clone and digested with either HaeIII or RsaI. Fragments of the genomic DNA were cloned into a sequencing vector for analysis.

Approximately $2.5 \times 10^6$ plaques from rodent cDNA libraries and $2.0 \times 10^6$ plaques from genomic libraries were screened with the full length human ICAM-R probe. No ICAM-R related clones were identified. An additional $0.5 \times 10^6$ plaques from rodent cDNA libraries and $1.0 \times 10^6$ plaques from rodent genomic libraries were screened with an ICAM-R domain 2 specific probe corresponding to nucleotides 372 to 663 of SEQ ID NO: 2. A genomic clone from rat was identified as a candidate for rodent homologue of domain 2 of ICAM-R. SEQ ID NOs: 23 and 24 set out sequence data (341 bp) for the rat domain 2 clone. Table 1 below indicates the DNA and amino acid sequence identity of the rat clone to corresponding regions of human ICAM-R, ICAM-1 and ICAM-2.

TABLE 1

| | Rat Clone Domain 2 | |
|---|---|---|
| | DNA | Amino Acid |
| Human ICAM-R | 67% | 61% |
| Human ICAM-1 | 65% | 60% |
| Rat ICAM-1 | 60% | 53% |
| Mouse ICAM-1 | 61% | 52% |
| Mouse ICAM-2 | 54% | 38% |

B. Isolation of a Partial Rat ICAM-R cDNA

The rat ICAM-R domain 2 DNA (SEQ ID NO:23) was used as a radiolabelled probe to screen rat macrophage, PBL and spleen λgt10 cDNA libraries (Clonetech, La Jolla, Calif.). The library screening conditions were as described in Section A above. A single clone was isolated from the spleen cDNA library. Sequence analysis of the clone revealed an insert of 1294 bp (including EcoR1 ends) with an open reading frame that spanned the entire insert. Alignment with human ICAM-R sequence demonstrated that the rat cDNA clone included nucleotides encoding domains 2–5 but lacked domain 1 at its 5' end and most of the transmembrane domain and all of the cytoplasmic tail at its 3' end. The DNA sequence of the partial rat ICAM-R cDNA is presented in SEQ ID NO: 25.

C. Isolation of a Full Length Rat Genomic Clone

An additional rat genomic ICAM-R clone that was subsequently isolated by the procedure described in Section A above includes both ICAM-1 and ICAM-R sequences indicating that the ICAM-1 and ICAM-R genes are on the same chromosome. Ballatyne et al., *Genomics*, 3: 547 (1991) reports that the rat ICAM-1 gene is on rat chromosome 9. The DNA sequence of the clone determined to date is presented in IUPAC nomenclature in SEQ ID NO: 26 and includes exons corresponding to the partial rat ICAM-R cDNA clone as well as an additional 1340 bp upstream and 960 bp downstream of the coding sequences.

D. Isolation of a Mouse Genomic Clone

A mouse genomic clone was isolated by the procedure described in Section A using the rat ICAM-R cDNA as a probe. The nucleotide sequences for 1593 bp of the 5' end of the ICAM-R encoding portion of the clone and of 2820 bp of the 3' of the ICAM-R encoding portion of the clone are set out in IUPAC nomenclature in SEQ ID NO: 27. The sequenced portions of the clone—are separated by a gap of approximately 120 bp which is represented by Ns in the DNA sequence of SEQ ID NO: 27.

EXAMPLE 7

Human ICAM-R cDNA was transfected into L-M(TK$^-$) mouse cells (ATCC CCL 1.3) and the cells were assayed for expression of ICAM-R by Northern blot and in situ hybridization.

A. Transfection of ICAM-R DNA

The full length human ICAM-R cDNA insert of pVZ-147 (Example 4) and a small portion of the phagmid vector 3' to the cDNA insert was excised using restriction enzymes NotI and XbaI and ligated into commercial plasmid pcDNA1-neo (Invitrogen Inc., San Diego, Calif.) cut with NotI and XbaI. The resulting plasmid, designated pcDNA1-neo-ICAM-R, was transfected into mouse L cells by the calcium phosphate precipitation method described in Chen et al., *Molecular and Cellular Biology*, 7: 2745–2748 (1987). ICAM-1 DNA (construct pcDNA-neo-ICAM-1) was also transfected into mouse L cells as a control. A cDNA fragment containing the complete ICAM-1 protein coding region was ligated into plasmid pcDNA1-neo and transfected into L cells by the calcium phosphate precipitation method. Following selection for neomycin resistance, individual ICAM-R or ICAM-1 transfectants were subcloned using cloning cylinders (Bellco Glass Inc., Vineland, N.J.). The clones expressing the highest level of ICAM-R and ICAM-1 protein were then sorted on a cell-sorter.

Constructs pcDNA-neo-ICAM-R and pcDNA-neo-ICAM-1 were also transfected into CV-1 cells by the calcium phosphate precipitation method. The clones expressing high levels of ICAM-R and ICAM-1 were selected as described above for L cell tranfectants. Based on FACs analysis with ICAM-R and ICAM-1 specific antibodies the level of protein expression was higher with CV-1 transfectants then with the mouse LTK transfectants.

B. Northern Blot Hybridizations

Following transfection of full length ICAM-R or ICAM-1 cDNAs into mouse L cells, specific expression of the corresponding mRNAs in transfected and untransfected L cells was determined by Northern blot hybridization with $^{32}$P-labelled ICAM-R or ICAM-1 DNA probes. Transfectants were grown in log phase, then centrifuged and washed two times with 150 mM NaCl. The pellet was resuspended in 3.5 ml GIT (guanidinium isothiocyanate) buffer, then sheared in a polytron mixer for 20 seconds. After adding 1.7 ml CsCl buffer to an ultracentrifuge tube, the GIT/RNA mix was layered on top. Samples were spun at 35 K (179,000×g), 20° C., for 21 hours. All liquid was removed and the pelleted RNA was resuspended in 300 μl 0.3M sodium acetate pH 5.2, then precipitated with 750 μl EtOH at −20° C. The precipitate was resuspended in H$_2$O, then treated with Proteinase K to remove any RNAses. After a phenol/chloroform extraction, the RNA was re-precipitated, resuspended in H$_2$O and the OD of the sample at 260 nm was measured.

The RNAs were electrophoresed in 1% formaldehyde agarose gels, prepared with diethyl pyrocarbonate (DEPC) treated solutions. Ten μg of each total RNA sample was loaded per lane. RNA was electrophoresed at 30 V for approximately 18 hours with continuous circulation of buffers accomplished with a peristaltic pump. Each resulting gel was soaked two times in 20×SSPE for 20 minutes each at room temperature. Transfer of RNA to Hybond-C membranes (Amersham Corp., Arlington Heights, Ill.) was accomplished by capillary action overnight in 20×SSPE. Using a Stratagene stratalinker, RNA was stably crosslinked to each membrane by exposure to ultraviolet light.

To generate ICAM-1 DNA probes, 100–200 ng template DNA (a 1.8 kb Xba/Kpn fragment incorporating the entire ICAM-1 coding sequence) was mixed with $H_2O$ and random hexamer, boiled for 5 minutes, and then incubated 5 minutes on ice. To the template DNA were added: $^{32}$P-dCTP and $^{32}$P-dTTP, $10^{-4}$M dGTP/dATP, 10×Klenow Buffer (Boehringer Mannheim Biochemicals, Indianapolis, Ind.) and Klenow enzyme, and the mixture was left at room temperature for 1 hour. Samples were passed over a Quickspin G25 DNA column (Boehringer) to separate incorporated from unincorporated label.

To generate ICAM-R DNA probes, 200 pg of DNA template (a 1.4 kb fragment of clone pVZ-147 truncated to remove the poly-A tail) was amplified by PCR primed with oligonucleotides complimentary to the 5' and 3' extremities of domain 1. $^{32}$P-dCTP was added to the reaction mixture. Samples were held at 94° C. for 4 minutes then run through 30 cycles of the temperature step sequence (94° C., 1 minute; 50° C., 2 minutes; 72° C., 4 minutes) Samples were then run over a Quickspin column and incorporation of label was assessed by scintillation counting of 1 μl aliquots.

The DNA probes were denatured with 5M NaOH, then neutralized with 1M Tris. The Hybond-C membranes were prehybridized at 50° C. for 30 minutes in a 50% formamide pre-hybridization mix. Probe was added to each membrane to a concentration of $1 \times 10^6$ cpm/ml hybridization mix (50% formamide, 5×Denhardt's solution, 5×SSPE, 1% SDS), and the membranes were incubated overnight at 42° C. Each membrane was then washed 5 times in 2×SSPE/0.1% SDS at room temperature for 10 minutes each wash. One 10 minute wash was done at 50° C. in 0.5×SSPE/0.1% SDS, with an additional rinse in 2×SSPE. Hybridization with the major RNA transcript was quantitated using a Molecular Dynamics (Sunnyvale, Calif.) Model 400A PhosphorImager.

Figure 2B:
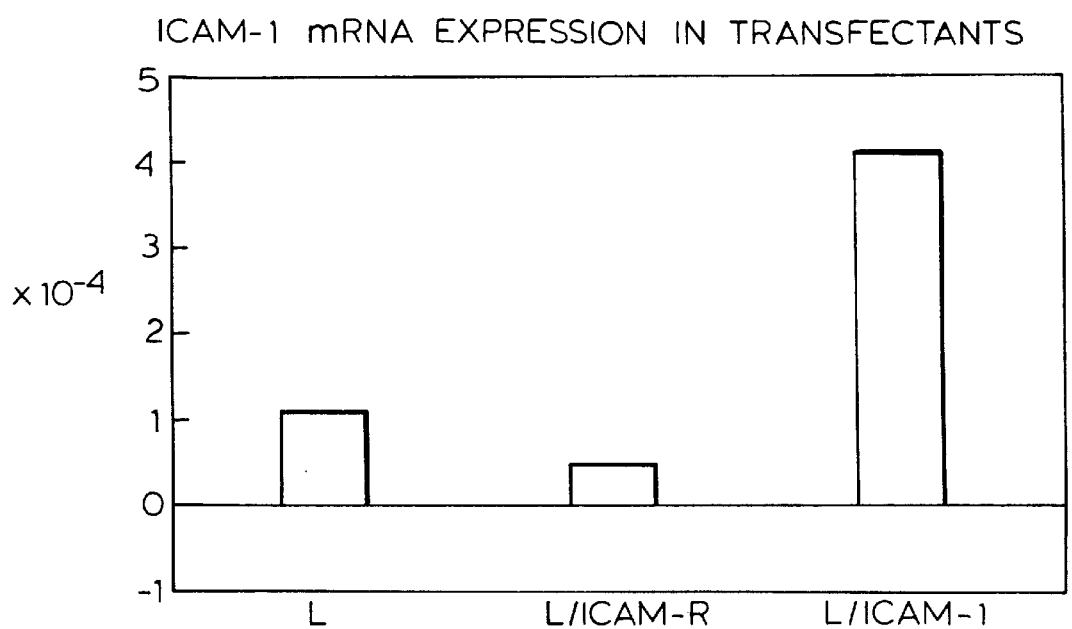
Figure 3A:
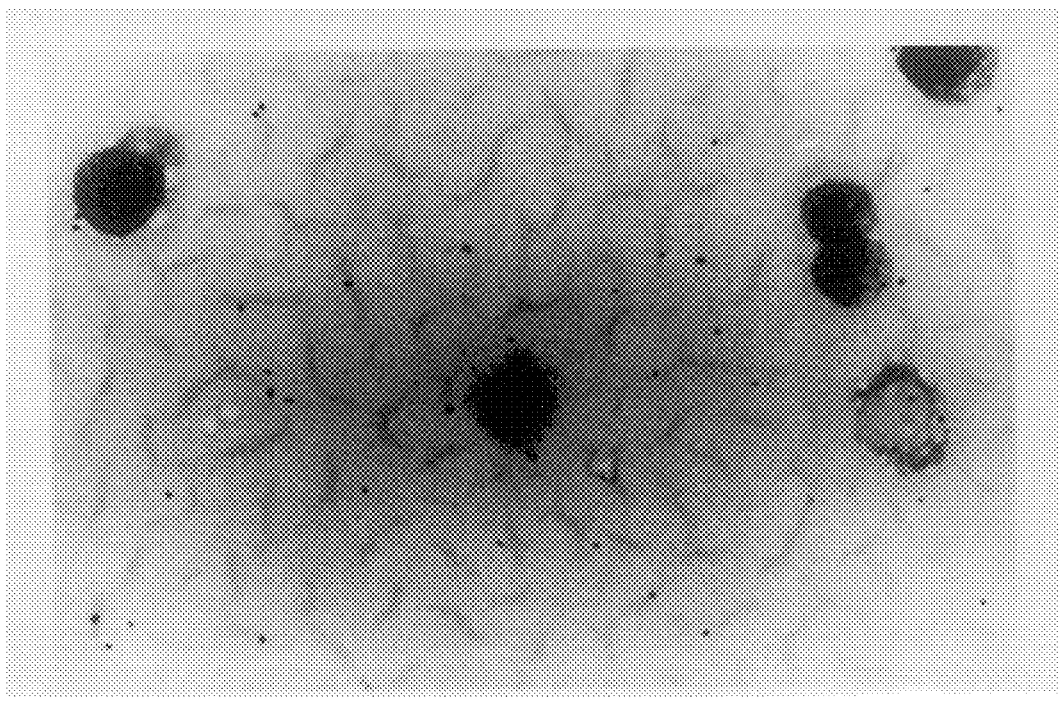
FIG. 3(A through F) presents photomicrographs depicting the results of in situ hybridizations of transfected L cells using ICAM-R or ICAM-1 RNA probes.
Figure 3B:
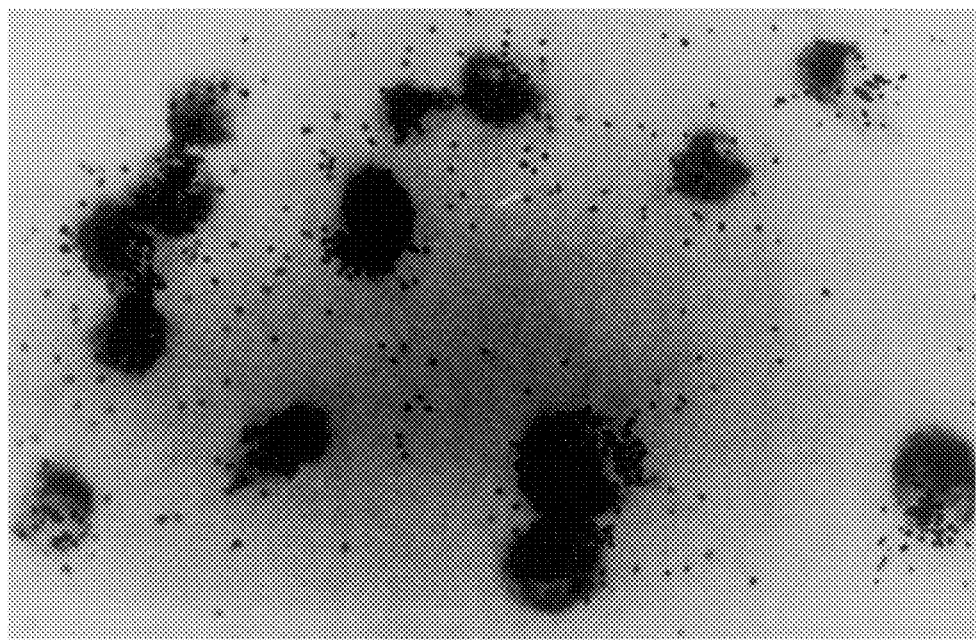
Figure 3C:
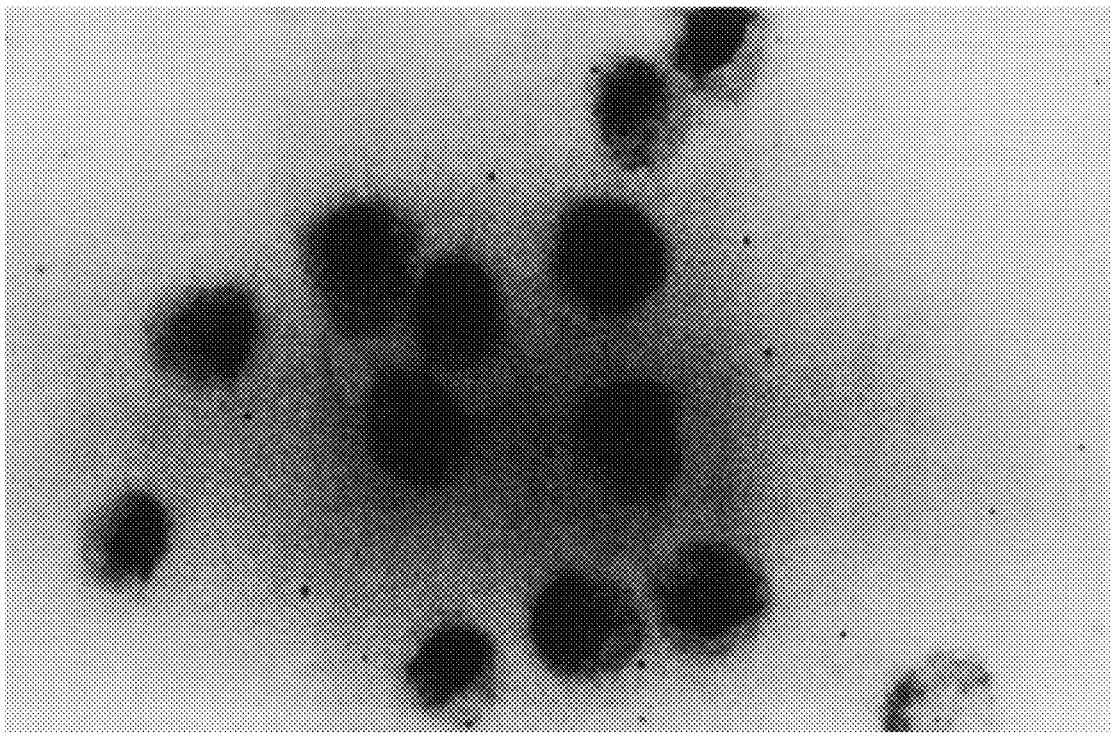
Figure 3D:
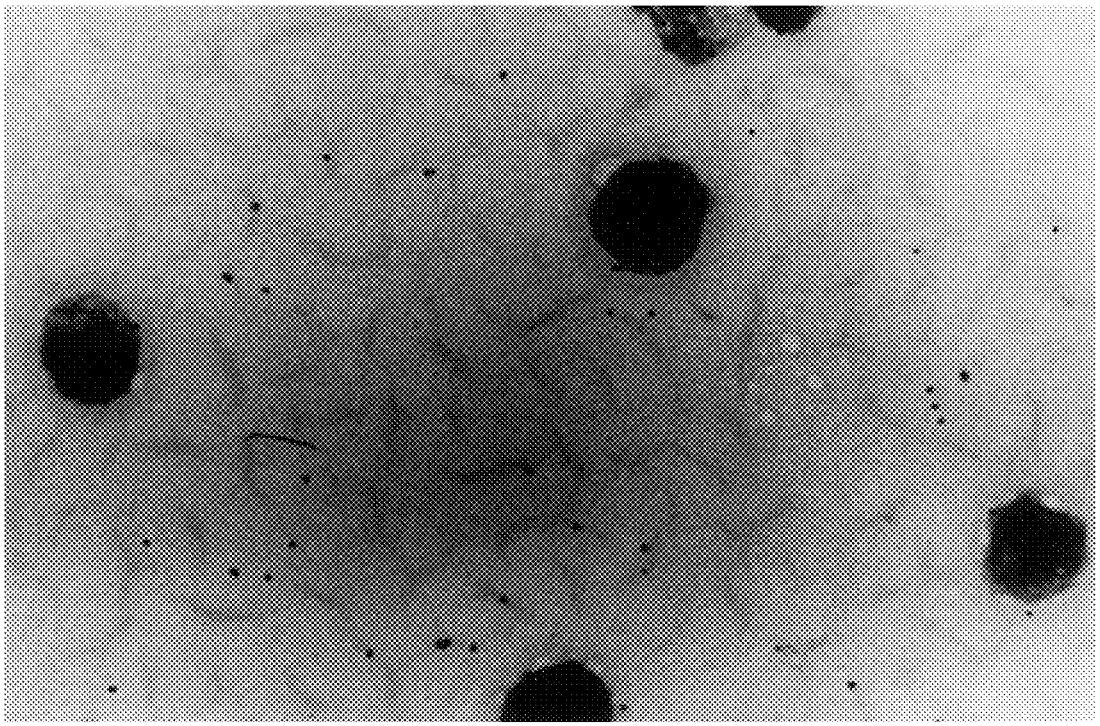
Figure 3E:
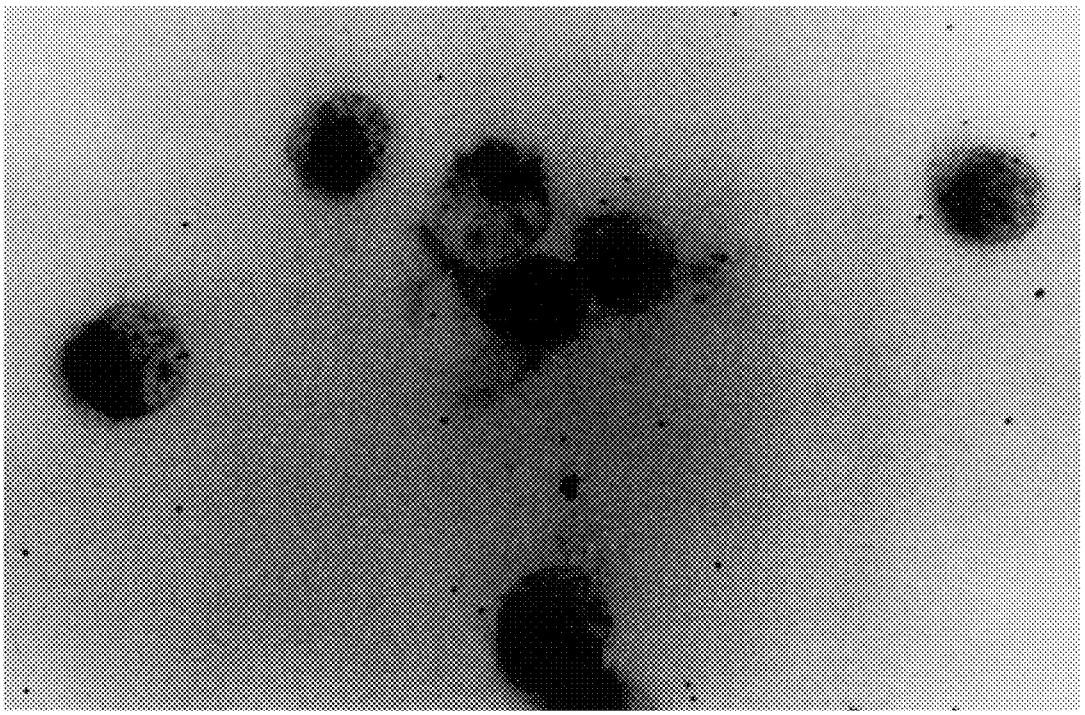
Figure 3F:
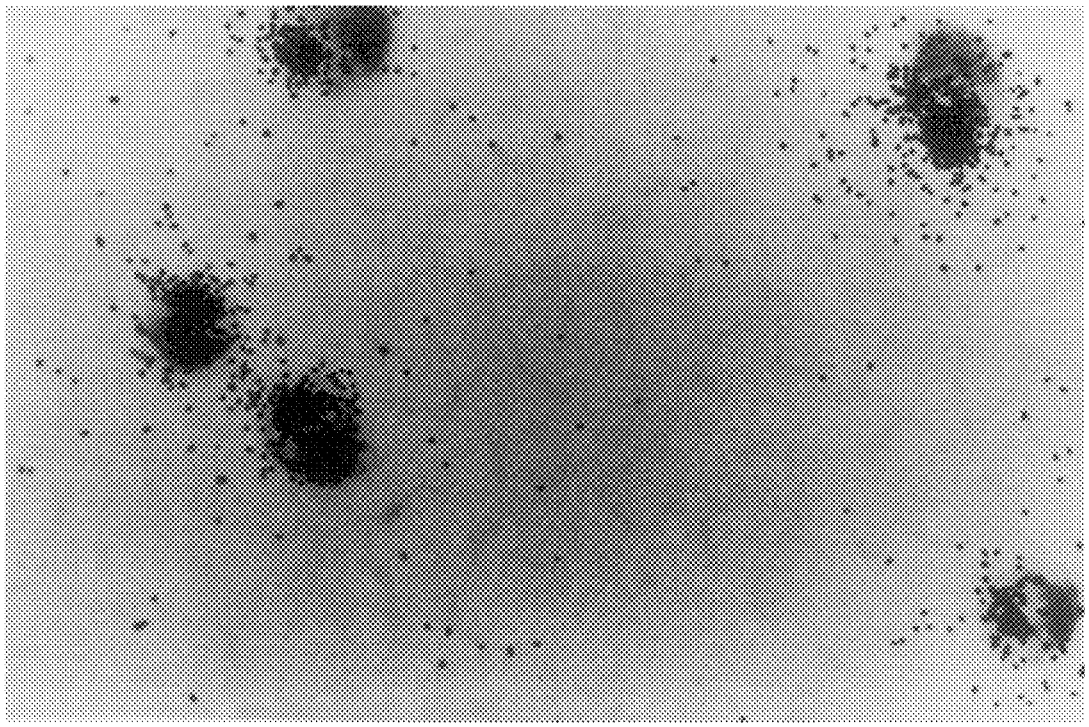

Results of the northern blot hybridizations are presented in bar graph form in FIG. 2(A through B). FIG. 2A illustrates specific hybridization of the ICAM-R probe with RNA extracted from ICAM-R transfectants, but not with RNA from ICAM-1 transfectants or untransfected L cells. Reciprocally, FIG. 2B indicates hybridization of the ICAM-1 probe with RNA extracted from ICAM-1 transfectants, but not with RNA from ICAM-R transfectants or parental L cells.

C. In situ Hybridizations

L cells and L cells transfected as described above with either ICAM-R or ICAM-1 cDNAs were hybridized in situ with radiolabelled single-stranded RNA probes derived from ICAM-R or ICAM-1. Single-stranded RNA probes were generated from DNA templates corresponding to the first (i.e., N-terminal) immunoglobulin-like domain of ICAM-R or ICAM-1 by in vitro RNA transcription incorporating $^{35}$S-UTP. Probes were chemically hydrolyzed to approximately 200 bp.

Transfected and untransfected L cells were layered onto Vectabond (vector Laboratories, Inc., Burlingame, Calif.) coated slides and stored at −70° C. Prior to use, slides were removed from −70° C. and placed at 55° C. for 5 minutes. Sections were then fixed in 4% paraformaldehyde for 20 minutes at 4° C., dehydrated in 70–95–100% EtOH for 10 minutes at room temperature, and allowed to air dry for 30 minutes. Sections were denatured for 2 minutes at 70° C. in 70% formamide/2×SSC, rinsed in 2×SSC dehydrated and then air dried for 30 minutes. Prehybridization for 2 hours at 42° C. with a mixture containing 50% formamide, 0.3M NaCl, 20 mM Tris pH 8.0, 10% dextran sulfate, 1×Denhardt's solution, 100 mM dithiothreitol (DTT) and 5 mM EDTA was performed. Hybridization was carried out overnight (12–16 hours) at 50° C. in the same mixture additionally containing either $^{35}$S-labelled ICAM-1 or $^{35}$S-labelled ICAM-R RNA probes ($6 \times 10^5$ cpm/section). After hybridization, sections were washed for 1 hour at room temperature in 4×SSC/10 mM DTT, then for 40 minutes at 60° C. in 50% formamide/1×SSC/10 mM DTT, 30 minutes at room temperature in 2×SSC, and 30 minutes at room temperature in 0.1×SSC. The sections were alcohol dehydrated, air dried for 30 minutes, developed (after storage at 4° C. in complete darkness) and counterstained with hematoxylin/eosin.

Photomicrographs of the in situ hybridizations are set out in FIG. 3(A through F) wherein photomicrograph 3A is of parental L cells probed with ICAM-R RNA; 3B is of ICAM-R transfected L cells probed with ICAM-R RNA; 3C is of ICAM-1 transfected L cells probed with ICAM-R RNA; 3D is of parental L cells probed with ICAM-1 RNA; 3E is of ICAM-R transfected L cells probed with ICAM-1 RNA; and 3F is of ICAM-1 transfected L cells probed with ICAM-1 RNA. The photomicrographs demonstrate specific hybridization of each RNA probe only with L cells transfected with a homologous cDNA.

EXAMPLE 8

Experiments testing the adhesion of leukocytes to transfected L cells expressing ICAM-R on their surface or to soluble ICAM-R (Example 11) indicate that ICAM-R is a ligand/receptor for an adhesion molecule or molecules on leukocytes.

A. CD18-Dependent Cell Adhesion

SKW3 cells (T lymphoblastoid cells) were pretreated with phorbol ester to activate LFA-1-dependent adhesion as described in Dustin et al., Nature, 341: 619–624 (1989) and were assayed for binding to ICAM-R and ICAM-1 transfectants.

Untransfected L cells or L cells transfected with either ICAM-R or ICAM-1 (see Example 7) were seeded in 24-well tissue culture plates ($3 \times 10^5$ cells per well) 24–48 hours prior to the adhesion assay. SKW3 cells were washed in serum-free RPMI (Gibco, Canada), labelled with Calcein-AM (Molecular Probes Inc., Eugene, Oreg.), and stimulated with 10 ng/ml phorbol myristylacetate (PMA) for 20 minutes at 37° C. Selected stimulated SKW3 cells were then pretreated with anti-CD18 (TS1/18, ATCC HB203), anti-CD11a (TS1/22, ATCC HB202) hybridoma supernatant or control anti-CD2 (ATCC HB195) purified monoclonal antibody for 30 minutes at room temperature before incubation with adherent, transfected L cells. Antibody-treated and non-antibody-treated, calcein-labelled SKW-3 cells were added ($5 \times 10^5$ cells per well) to confluent monolayers of ICAM-R or ICAM-1 transfectants and incubated for 30 minutes at 37° C. in RPMI/1% fetal calf serum (FCS, Hyclone laboratories Inc., Logan, Utah) Unbound cells were aspirated and wells were filled with RPMI-FCS. Plates were sealed, centrifuged in an inverted position at 200 rpm for 4 minutes and aspirated. The plates were then washed with RPMI-FCS and scanned with an automatic fluorescence reader.

Adhesion of stimulated SKW3 cells to both the ICAM-R and the ICAM-1 transfectants was inhibited by monoclonal antibodies against either the α (CD11a) or β (CD18) chains of LFA-1 indicating that ICAM-R may participate in intercellular adhesion events involving a β2 integrin pathway. Intracellular adhesion was unaffected by the control anti-CD2 reagent.

B. CD18-Independent Cell Adhesion

Figure 4A:
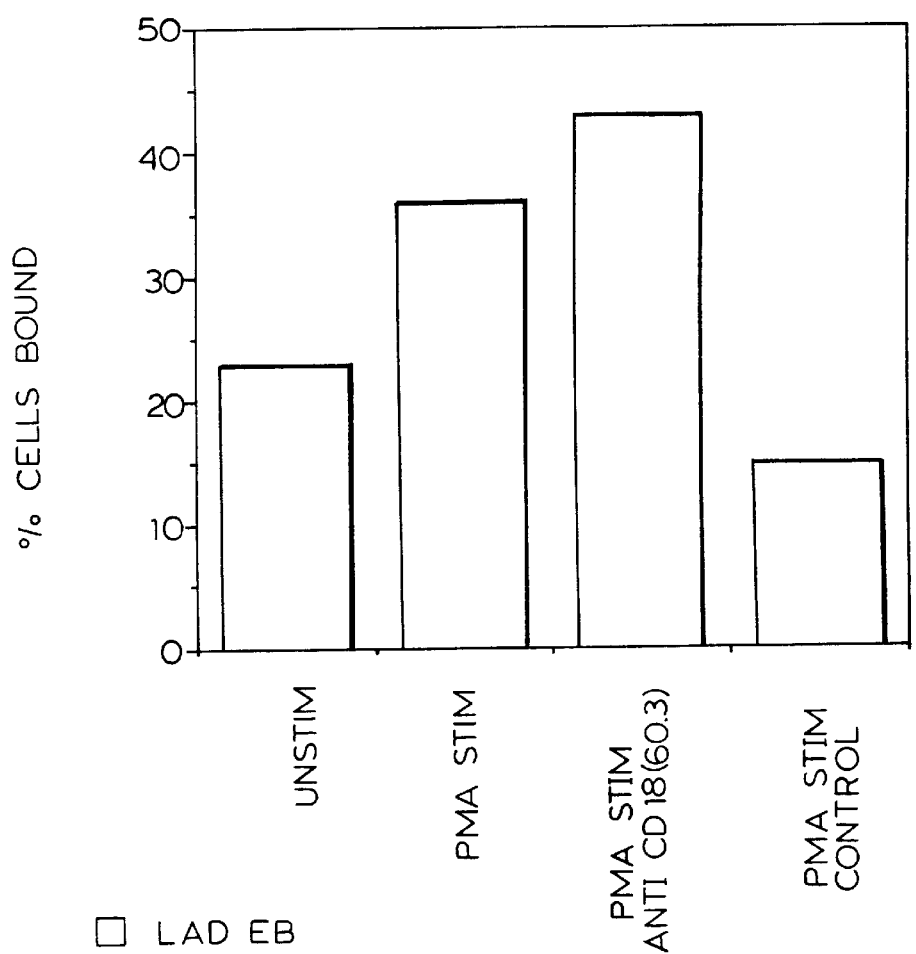
FIG. 4A comprises bar graphs illustrating the results of assays for the adhesion of PMA-stimulated or unstimulated lymphoblastoid cells from patients with leukocyte adhesion deficiency to soluble ICAM-R in the presence and absence of anti-CD18 antibody, while FIG. 4B comprises bar graphs illustrating the results of assays for the adhesion of various other PMA-stimulated or unstimulated cell lines to soluble ICAM-R in the presence and absence of anti-CD 18 or anti-CD11a antibody.
Figure 4B:
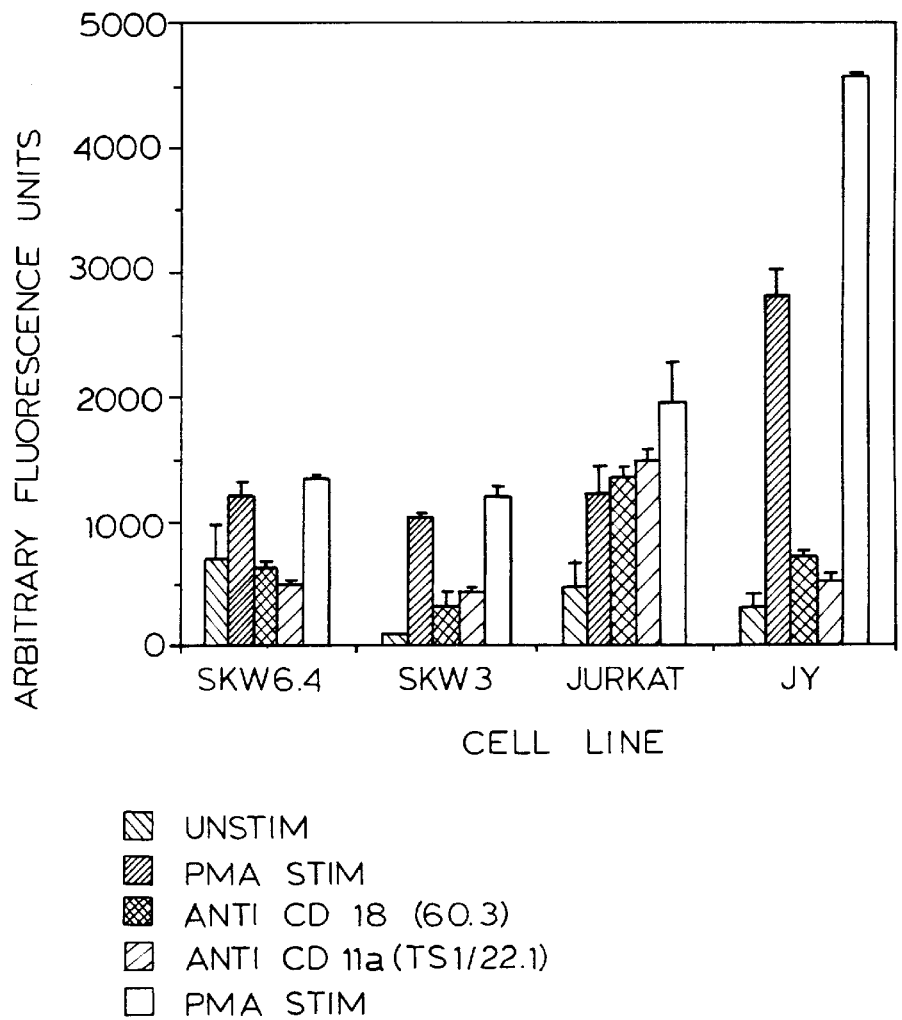

CD18 negative lymphoblastoid cells from patients with leukocyte adhesion deficiency (LAD) bind to soluble ICAM-R described in Example 11. (See FIG. 4A wherein the experimental control was binding of cells to plates coated with 1% BSA.) In addition, the majority (80–90%) of binding of the Jurkat T lymphoblastoid cell line to ICAM-R is not inhibited by anti-CD18 monoclonal antibody [60.3 described in Beatty et al., *J. Immunol.*, 131: 2913–2918 (1983)] or anti-CD11a monoclonal antibody (TS1/22) (FIG. 4B). These results suggest that binding of ICAM-R to these cell lines is CD18-independent and that LAD and Jurkat cells express a counterreceptor for ICAM-R that is not a $β_2$ integrin.

EXAMPLE 9

Human sequence ICAM-R peptides were used to inhibit SKW3 and Jurkat cell binding to ICAM-R. The former type of adhesion is CD18-dependent while the latter is largely CD18-independent.

Based on amino acid sequence alignment with known $β_1$ integrin binding domains in fibronectin and based on epitope mapping of anti-ICAM-R monoclonal antibodies that block cell adhesion (see Table 11 in Example 21), ICAM-R peptides corresponding to potential integrin binding sites were synthesized by Macromolecular Resources (Colorado State University, Fort Collins, Colo.). Four ICAM-R sequences which lie between or at the border of predicted beta strands in domains 1 and 3 of were chosen. Similar but not identical βN-strand predictions for ICAM-1 are set out in Staunton et al., *Cell*, 61: 243–254 (1990). Inhibition was assayed using a system involving cell adhesion to soluble ICAM-R coated plastic. Calcein-labeled cells (see Section A above) were incubated with peptide at 1–2 mg/ml for 20 minutes at 25° C. and the cells were transferred to wells of a 96-well plate previously coated with soluble ICAM-R (see Example 11) and containing 10 μg/ml final concentration phorbol 12-myristate 13-acetate (PMA). After 50 minutes, the plate was inverted in PBS for 10 minutes to remove unbound cells. Bound cells were quantitated using a fluorescence concentration analyzer.

The results of the assay are presented below in Table 2 wherein numbering of peptide residues of ICAM-R corresponds to SEQ ID NO: 1 while numbering of peptide residues of ICAM-1 corresponds to the ICAM-1 amino acid sequence presented in Staunton et al., supra, and wherein the abbreviation "ND" stands for "not determined."

TABLE 2

| Protein | Domain | Peptide Residues | % Inhibition CD18-Dependent Binding (SKW3) | % Inhibition CD18-Independent Binding (Jurkat) |
| --- | --- | --- | --- | --- |
| ICAM-R | 1 | 32–38 | 0% | 10% |
| | 1 | 72–76 | 26% | 17% |

TABLE 2-continued

| Protein | Domain | Peptide Residues | % Inhibition CD18-Dependent Binding (SKW3) | % Inhibition CD18-Independent Binding (Jurkat) |
| --- | --- | --- | --- | --- |
| | 3 | 230–234 | 0% | 36% |
| | 3 | 271–276 | 0% | 11% |
| ICAM-1 | 1 | 29–35 | ND | ND |
| | 1 | 70–74 | 0% | 9% |
| | 3 | 228–232 | ND | 22% |
| | 3 | 268–274 | ND | ND |

ICAM-R peptide sequences from domain 3 inhibited binding of Jurkat ceUs to ICAM-R but not binding of SKW3 cells to ICAM-R. Domain 3 peptides were two-fold more efficient than domain 1 peptide sequences in inhibiting Jurkat cell binding, suggesting that Jurkat binding to ICAM-R may preferentially involve ICAM-R domain 3. The ICAM-R domain 1 peptide (NGSQI) corresponding to residues 72–76 of SEQ ID NO: 1 inhibited SKW3 binding to ICAM-R by 26%. The corresponding ICAM-1 peptide (DGQST, SEQ ID NO: 28) did not inhibit binding. In contrast, the ICAM-R domain 3 peptide (GDQML) corresponding to amino acids 230–234 of SEQ ID NO: 1 demonstrated the best inhibition (36%) of Jurkat binding to ICAM-R. The corresponding ICAM-1 peptide (GDQRL, SEQ ID NO: 29) inhibited Jurkat binding by 22%.

The tri-peptide RGD is a recognition sequence common to extracellular matrix components (e.g., fibronectin and vitronectin) that are ligands of the beta-1 integrins. Cyclizing RGD-containing peptides has resulted in a ten-fold increase in efficiency of blocking integrin binding to vitronectin [Pierschbacher and Ruoslahti, *J. Biol. Chem.*, 262 (36): 17294–17298 (1987)]. ICAM-R peptide sequences corresponding to domain 1 residues 72–77 and domain 3 residues 230–234 are being cyclized using bromoacetic acid preparative to tesing in the assay outlined above.

EXAMPLE 10

A panel of rat ICAM-R/glutathione S-transferase (GST) fusion proteins was generated for use as immunogens using the bacterial expression vector pGEX-2T (Pharmacia Biotech, Inc., Alameda, Calif.). The plasmid vector contains an IPTG inducible promoter adjacent to a multi-cloning site located upstream of GST encoding DNA sequences.

A. Fusion Proteins Comprising Multiple Domains of Rat ICAM-R

The rat ICAM-R partial cDNA clone described in Example 6 was used to generate polynucleotides encoding ICAM-R fragments, the first composed of domains 2, 3 and the N terminal 36 amino acids of domain 4 (amino acids 1 to 240) of rat ICAM-R and the second including the remaining 104 amino acids of domain 4 and all of domain 5 (amino acid 240 to 430). The internal EcoRI site at position 718 of the cDNA clone (SEQ ID NO: 25) was used to generate the polynucleotide fragments. Each fragment was cloned into the EcoRI site of pGEX-2T upstream of GST encoding sequences and the resulting plasmids were transformed into *E. coli*. The insert orientation and reading frame were confirmed by sequence analysis. Bacteria containing the recombinant plasmids were grown overnight and expression of the fusion proteins was induced with 0.1 mM IPTG. Both ICAM-R/GST fusion proteins remained in the insoluble fraction after the bacteria were lysed by sonication in PBS+SDS(1%). The insoluble proteins were boiled in SDS loading dye and run on a 10% preparative polyacrylamide SDS gel. The gel was stained in 0.4M KCl and the fusion protein bands were excised. Fusion proteins were electroeluted from the polyacrylamide gel slices in dialysis tubing using 25 mM Tris/192 mM glycine gel buffer.

B. Fusion Proteins Comprising Single Domains of Rat ICAM-R

Rat ICAM-R domain-specific fusion proteins were also constructed in pGEX-2T. The following primers that correspond to the 5' and 3' ends of domains 1 and 2 were used to generate by PCR DNA fragments that respectively encoded ICAM-R domains 1 and 2. Domain 1 specific PCR primers were based on the sequence of the rat genomic clone and domain 2 specific primers were based on the sequence of the rat cDNA clone (see Example 6).

RRpGEX-D1 5' (SEQ ID NO: 30)
ACCGAATTCGTTTCTGGGCGACCTTCAG
RRpGEX-D1 3' (SEQ ID NO: 31)
TGGAATTCGCTCACGGAAAGTTCGGAT
RRpGEX-D2 5' (SEQ ID NO: 32)
GCGAATTCGGGTAGAGCTAGTGCCTCTG
RRpGEX-D2 3' (SEQ ID NO: 33)
TGGAATTCGAAACGTGCGGAGCTGTCT

PCR was performed with 50 µl reaction mixtures consisting of domain 1 or domain 2 primer pairs (10 µg/ml), a mixture of all four dNTPs (0.2 mM each), template DNA (1 ng of rat ICAM-R genomic clone DNA) and Taq polymerase (1 unit/reaction) in a buffer composed of 10 mM Tris pH 8.3, 50 mM KCl and 1.5 mM MgCl$_2$. Thirty reaction cycles of 95° C. for 2 minutes, 50° C. for 2 minutes, and 72° C. for 4 minutes were performed. The resulting domain 1 and 2 PCR fragments were cloned into the EcoRI site of pGEX-2T and transformants were screened for their ability to produce fusion protein of the appropriate molecular weight. DNA sequence analysis confirmed correct orientation and reading frame. Isolation and purification of the domain 1 and 2/GST fusion proteins was carried out as described above in Section A.

EXAMPLE 11

A soluble variant of ICAM-R was constructed and expressed as follows.

The human cDNA for ICAM-R was altered by standard procedures of site-directed mutagenesis [see, e.g., Kunkel et al., *Proc. Natl. Acad. Sci. USA*, 82: 488–492 (1985)] in order to truncate the protein coding sequence at the predicted junction (amino acid 457) of its extracellular and transmembrane domains as determined by a computer algorithm that predicts hydropathy [Kyte et al., *J. Mol. Biol.*, 157: 105–132 (1982)]. The DNA sequence of ICAM-R was cut from pVZ147 (Example 4) with restriction enzymes SalI and NotI. The resulting fragment included the complete ICAM-R coding sequences beginning at the 5' end of the coding strand and also included at the 3' end a short segment of the multiple cloning sites. This fragment was subcloned into the M13 BM21 vector (Boehringer) linearized with SalI and NotI resulting in a molecule called M13 BM21ICAM-R.

A mutagenizing oligonucleotide was synthesized with the sequence below.

ICAM-Rt1 (SEQ ID NO: 34)
CTGCCCCTGAATCACCCTCGA

The oligonucleotide changes the phenylalanine at position 457 of ICAM-R to a stop codon. The oligonucleotide was utilized as described in Kunkel et al., supra, to generate from M13 BM21ICAM-R six M13 phage isolates encoding a stop codon at position 457. An isolate designated BM21ICAM-Rt1 was chosen for further study.

This single strand template was converted to a double strand DNA molecule by primer extension using Klenow DNA polymerase as follows. Ten µg of purified single strand M13 BM21ICAM-Rt1 DNA was annealed to 50 ng Lac Z universal −20 primer (GTAAAACGACGGCCAGT, SEQ ID NO: 35) in 1×Klenow DNA polymerase buffer (10 mM Tris-Cl pH 7.5, 5 mM MgCl$_2$, 7.5 mM dithiothreitol) by incubating the mix at 6° C. for 5 minutes and then 25° C. for 5 minutes. The following mixture was then added to the annealing reaction: 33 µM final concentration dATP, dGTP, dCTP, dTTP; 4 units of Klenow DNA polymerase (Boehringer), and 1×Klenow buffer. The primer extension reaction was allowed to incubate at 37° C. for 45 minutes prior to being stopped by a single phenol\chloroform (1:1) extraction and ethanol precipitation. A portion of the cDNA insert was released from the M13 BM21ICAM-Rt1 phage by restriction digest using restriction enzymes EcoRV and NcoI. The fragment of DNA released contained the complete coding sequence for the truncated ICAM-R protein, the 3' untranslated region and a small segment of polylinker sequence from the M13 BM21 phage. After agarose gel purification the fragment was ligated to linearized vector Bluebac III (Invitrogen Corp., San Diego, Calif.), a transfer vector containing genomic baculovirus sequences for homologous recombination that flank the ETL promoter driving expression of the *E. coli* beta-galactosidase gene and the polyhedron promoter driving expression of the gene of interest, in this case ICAM-Rt1.

The Bluebac III vector had been prepared in the following way prior to ligation. Three µg of supercoiled plasmid DNA was digested with 20 units HinDIII endonuclease (Boehringer). After a phenol/chloroform extraction and ethanol precipitation the DNA pellet was resuspended in 1×Klenow DNA polymerase buffer; 33 µM final concentration dATP, dGTP, dCTP, dTTP; 2 units of Klenow DNA polymerase (Boehringer) and incubated at 37° C. for 60 minutes to fill in the termini of the molecule. The fill-in reaction was terminated by phenol/chloroform extraction and precipitation with ethanol. The blunt-ended DNA was resuspended in 1×NcoI buffer, 20 units of NcoI endonuclease were added and incubated at 37° C. for 60 minutes.

A portion of the ligation reaction of the ICAM-Rt1 insert and linearized plasmid was used to transform electrocompetent XL-1 *E. coli* (Stratagene) and individual colonies were selected on LB plates supplemented with 60 µg/ml carbenicillin. Twelve individual isolates were analyzed by digestion of mini-prep DNA using PstI or EcoRI for diagnostic purposes. One isolate that exhibited the expected band pattern was designated pBBIII.CAM-Rt1.

Sf-9 cells (Invitrogen) to be transfected or infected with pBBIII ICAM-Rt1 DNA were maintained in spinner flasks in TNM-FH [Grace's medium (Gibco, Grand Island, N.Y.) supplemented with 10% heat inactivated fetal bovine serum and gentamicin at 10 µg/ml] at 27° C. in a forced draft incubator. Spinner flask impellers were rotated at 60 rpm on an insulated five place stir plate. Log phase Sf-9 cells (1.5–2.5×10$^6$/ml) with greater than 90% viability were routinely subcultured twice weekly.

Sf-9 cells at log growth phase were plated (2×10$^6$ cells/60 mm dish) in TNM-FH medium and allowed to attach for 1 hour at 27° C. After this time the following mixture was made up in a sterile polystyrene tube and incubated at room temperature for 15 minutes: 1 ml TNM-FH medium, 1 µg linear *Autographa californica* nuclear polyhidrosis virus (AcNPV, baculovirus) genomic DNA (Invitrogen), 3 µg of pBBIII.ICAM-Rt1 DNA and 20 µl of a stock cationic liposome solution (Invitrogen). Two other independent mixtures were made up with or without pBluebac III substituted for pBBIII.ICAM-Rt1 DNA as controls. The media was removed from the seeded plates, replaced with 2 ml of Grace's medium and allowed to incubate for 2 minutes. All media was removed from the plates and the DNA/liposome mixtures were added dropwise on the cells of individual plates. One plate received TNM-FH medium alone as a mock transfection control. The plates were then incubated at 27° C. for 4 hours with occasional rocking. Following this incubation, 1 ml of TNM-FH medium was added to the plates. After further incubation for 48 hours, the transfection media containing virus was removed and these viral stocks were used to infect plates of Sf-9 cells for plaque identification.

Sf-9 cells were seeded at $2 \times 10^6$ cells/60 mm dish in TNM-FH medium and allowed to attach for approximately 1 hour at 27° C. The media was removed. Several 10-fold serial dilutions were made from each viral stock and 1 µl of each dilution was added to a single dish of adherent Sf-9 cells and incubated for 1 hour at 27° C. Following removal of the virus inoculum, each dish of cells was overlayed with 3 ml of a mixture of TNM-FH medium, 0.625% low melting point agarose (BRL, Gaithersburg, Md.) and 300 µg/ml halogenated idolyl-beta-D-galactosidase (Bluo-gal, BRL) that had been previously equilibrated to about 30° C. and allowed to solidify at room temperature for 1 hour. The plates were then incubated until blue color developed (typically 4–5 days). Twenty-four plaques of recombinant viruses (identified due to their expression of beta-galactosidase and conversion of the chromogenic substrate, Bluo-gal to a blue precipitate in infected cells) were transferred to individual wells of a 24-well cell culture plate that had been seeded with 1 ml of Sf-9 cells ($2 \times 10^5$/ml) in TNM-FH. After 5 days at 27° C. the media was harvested, microfuged at 1,000 rpm for 5 minutes at 4° C. and the resulting supernatant was transferred to a fresh tube. These stocks were designated as BacR.P1 stocks with their respective isolate number.

BacR.P1 stocks were assayed for the production of ICAM-R by an antigen capture (ELISA) assay. Anti-ICAM-R monoclonal antibody 26I10E-2 (see Example 13) was biotinylated as follows. A tenth volume of 1M $NaCO_3$ was added to monoclonal antibody 26I10E at 1 mg/ml. NHS-biotin (Sigma Chemical Co., St. Louis, Mo.) was dissolved into dimethyl sulfoxide (DMSO, Mallinckrodt, Paris, Ky.) at 1 mg/ml. One hundred eighty µl biotin solution was added to each 1 mg antibody and rotated at 4° C. overnight. The biotinylation reaction was terminated by dialysis against PBS for 16 hours with 3 changes at 4° C. For the assay of BacR.P1 stocks, each well of a ninety-six well plate was coated with monoclonal antibody 26E3D (50 µl at 10 µg/ml) for either 2 hours at 37° C. or 16 hours at 4° C. The coating was then aspirated and the wells were rinsed 2 times with PBS. Wells were blocked with 200 µl of 1% BSA in PBS for 30 minutes at 37° C. Two ten-fold serial dilutions of BacR.P1 stocks were made in PBS. Fifty µl from the BacR.P1 stocks (neat) or the dilutions were added to the wells and incubated for 30 minutes at 37° C. After 2 washes with PBS, 50 µl for a 1:250 dilution of biotinylated 26I10E in 1% BSA/PBS was added to the wells and incubated for 30 minutes at 37° C. After 3 washes with PBS, 50 µl/well of horseradish peroxidase conjugated to streptavidin (Zymed Laboratories Inc., San Francisco, Calif.) diluted in 1% BSA/PBS to 1:4000 was added and incubated for 30 minutes at 37° C. After 2 washes with PBS, 200 µl/well substrate buffer with ABTS (Zymed) was added and incubated at room temperature until a color reaction developed. The plate was read in an automated plate reader at a wavelength of 410 nm.

Four of the highest expressors of soluble ICAM-R as determined by the above antigen capture assay were chosen for plaque purification and BacR.P1 stocks of those isolates were diluted by 10-fold serial dilutions and plated with an agar overlay. A single blue plaque from the highest dilution was isolated and placed in 1 ml of TNM-FH medium, vortexed vigorously and serially diluted for one more round of plaque isolation. A final plaque isolate was chosen that was clear of all wildtype baculovirus and removed to a T-25 flask that has been seeded with $2 \times 10^6$ Sf-9 cells in TNM-FH media. After 5 days incubation at 27° C., the media was harvested by centrifugation at 1200 rpm for 5 minutes and 4 ml of the supernatant (designated BAC-R.P2 stock) was transferred to a 1 liter spinner flask containing 500 ml of TNM-FH seeded with $2 \times 10^6$ cells/ml. After another 5 days incubation at 27° C., the infection media was harvested by centrifugation at 1000 rpm for 5 minutes. The supernatant was stored at 4° C. and was designated BAC-R.P3 stock. The BAC-R.P3 stock was titered by plating aliquots of ten fold serial dilutions onto adherent Sf-9 cells and overlaying with 0.625% agarose in TNM-FH supplemented with 300 µg/ml Bluo-gal (BRL). After 4 days incubation at 27° C., the number of plaques was counted and a titer determined.

Infections for expression of soluble ICAM-R protein were carried out in 3 liter flasks containing 1.5 L of EX/Cell 401 medium (JRH Biosciences, Lenexa, Kans.). Sf-9 cells dividing at log phase ($2 \times 10^6$/ml) were infected at a multiplicity of infection (moi) of 5 with BAC-R.P3 virus stock. After 4 days, the media was harvested and was separated from the cells by centrifugation. Soluble ICAM-R protein was purified from the insect cell media as follows. Four ml 1M Tris-Cl pH 7.5. was added to each 200 ml of insect cell supernatant and was pumped at about 35 ml/hour at 4° C. onto a ~3.5 ml column of Lentil Lectin Sepharose (Pharmacia, Uppsala, Sweden) previously equilibrated with 20 mM Tris-Cl pH 7.5/0.1M NaCl (equilibration buffer). After loading, the column was washed with 25 ml equilibration buffer. The column was then eluted with 11 ml equilibration buffer containing 0.2M methyl α-D-mannopyranoside. The eluate contained soluble ICAM-R.

The partially purified soluble ICAM-R protein was assayed for binding to SKW3 cells that were pretreated with phorbol ester as described in Example 8 to activate LFA-1-dependent adhesion. The ICAM-R protein was coated onto 96-well Immulon 4 (Dynatech) plates after adjusting the lectin eluate to 25 mM carbonate pH 9.6 and incubated overnight at 4° C. The plates were washed two times with PBS, blocked for 30 minutes at 37° C. with 200 ul/well PBS, 1% BSA, and washed again with PBS before adding cells. SKW3 cells were washed in serum-free RPMI (Gibco), labelled with Calcein-AM (Molecular Probes), and stimulated with PMA. Cells were then added to the plates and incubated for 1 hour at 37° C. The plates were inverted in prewarmed PBS, 1% BSA and were incubated for 30 minutes. The plates were then removed and half of the contents of each well was aspriated. The plates were then scanned with a fluorescence microscope and an automated fluorescence reader. The results of the assay demonstrated adhesion of phorbol ester-activated lymphocytes to the plate bound ICAM-R protein.

In wtro assays for identifying antibodies or other compounds which modulate the activity of ICAM-R may be developed that utilize soluble ICAM-R. For example, such an assay may involve immobilizing ICAM-R or a natural ligand to which ICAM-R binds, detectably labelling the nonimmobilized binding partner, incubating the binding partners together and determining the effect of a test compound on the amount of label bound wherein a reduction in the label bound in the presence of the test compound compared to the amount of label bound in the absence of the test compound indicates that the test agent is an inhibitor of ICAM-R binding. Functional $\beta_2$ leukointegrins that may be utilized in such assays are described in Dustin et al., *CSH Symp. Qual.*, 54: 753–765 (1989).

The following preliminary experiment shows that purified soluble ICAM-R can be bound to polystyrene beads and retain the ability to bind to purified leukointegrins coated on a plastic surface, thus providing the basis for development of an assay to identify modulators of ICAM-R binding. Purified soluble ICAM-R was used to coat 6 μm fluorescent polystyrene beads (Polysciences, Inc., Warrington, Pa.) overnight according to the manufacturer's instructions and then the beads were blocked with BSA. Replicate wells of a 96-well plate were coated with a diluted aliquot of purified LFA-1 (CD18/CD11a), Mac-1 (CD18/CD11b) or Gp 150,95 (CD18/CD11c). After blocking the wells with BSA, the plates were incubated in buffer alone or buffer including anti-CD 18 antibody (60.3). The ICAM-R-coated beads were aliquoted into the well and incubated for one hour at room temperature followed by inversion in a tank of PBS-D to remove unbound beads from the wells. Fluorescence remaining in the wells was detected using a Cytofluor 2300 (Millipore, Inc., Bedford, Mass.). In parallel experiments, leukointegrin preparations of LFA-1 or Mac-1 were coated on the fluorescent polystyrene beads and ICAM-R was immobilized.

EXAMPLE 12

To rapidly screen for the functional consequences (i.e., counter-receptor binding) of point mutations in ICAM-R extracellular immunoglobulin-like domains, a system was employed from which soluble ICAM-R molecules having point mutations can be expressed and purified. The system relies on the specific binding properties of a poly-histidinyl tract fused to the amino or carboxyl terminus of a given protein [Hochuli et al., *Bio/Technology*, 6: 1321–1325 (1988)]. The utility of the system in the purification of proteins under native conditions has been demonstrated [Janknecht et al., *Proc. Natl. Acad. Sci., USA*, 88: 8972–8976 (1991)].

Plasmids pCS57.1 and pCS65.10 [both are pcDNA1amp (Invitrogen) with the full length human ICAM-R cDNA inserted between EcoRV and XhoI sites, but pCS65.10 includes point mutations that encode Ala$_{37}$ and Ser$_{38}$ rather than the wild type Glu37 and Thr38, respectively] were used for the initial studies. These DNAs were digested with SacI and EcoRI to release the entire extracellular domain of ICAM-R (amino acids −29 to +454) and the fragments were gel isolated.

Two complimentary oligonucleotides were synthesized that encoded wild type residues Ser$_{454}$ and Ser$_{455}$, and introduced a Gly$_{456}$, Pro$_{457}$ and Gly$_{458}$ to encourage an alpha helical turn followed by a stretch of six His residues and a translational terminator codon. The sequences of the oligonucleotides were:

SEQ ID NO: 36

CAGGTCCCGGTCATCATCATCATCATCATTAAT

SEQ ID NO: 37

TAGATTAATGATGATGATGATGATGAC-CGGGACCTGAGCT

The oligonucleotides which contain a SacI site and an XbaI site at the ends were ligated to the extracellular domain of ICAM-R and pcDNA1amp cut with EcoRI and XbaI. One set of ligations contained ½ unit polynucleotide kinase to phosphorylate the 5' ends of the synthetic DNAs thus increasing the efficiency of ligation. A second set of ligation reactions contained pre-phosphorylated oligonucleotides. Colonies were screened by either miniprep restriction enzyme digestion analysis and PCR with ICAM-R specific oligonucleotide primers or PCR alone. DNA sequence was obtained for several clones. The resulting plasmids were designated p57.1wtHis6 and p65.10E37T His6.

COS cells were seeded in 10 cm dishes and grown to about 50% confluency at which time they were transiently transfected by the DEAE-dextran method in serum free DMEM using 10 ug of purified plasmid DNA per dish or mock transfected. After a brief DMSO shock, the cells were incubated in DMEM supplemented with fetal bovine serum. After 24 hours, the medium was replaced and the cells allowed to reach confluency over the course of the next four days. The final medium harvest was removed from the cell monolayer and spun at 1000 rpm to remove cells and stored at 4° C. until ready for column chromatography.

Ni$^{++}$-nitrilotriacetic acid (Ni$^{++}$-NTA) agarose affinity column chromatography was performed essentially as described in Janknecht et al., supra, except that the purification was from medium rather than from lysed cells. To the medium was added an equal volume of buffer A (830 mM NaCl, 34% glycerol, 1.6 mM imidazole) and the mixture was clarified by centrifugation at 10,000×g for 10 minutes at 4° C. One ml of an Ni$^{++}$-NTA agarose bead suspension (50%) (Qiagen) per 16 mls of buffered medium sample was preequilibrated in 3.3 ml of 0.5×buffer A by gentle rocking at 25° C. for 30 minutes. The beads were then spun to a pellet at 600 rpm and most of the supernatant was removed. The beads were resuspended to a total volume of 3 ml in fresh 0.5×buffer A and 1 ml dispensed to each clarified and buffered medium sample. The remainder of the prep was carried out at 4° C. After 60 minutes of constant agitation each medium sample was passed through a disposable 10 ml polypropylene column (Biorad) to pack the beads and the flow through collected. The beads were then washed with 9 column volumes (4.5 mls) of buffer D (10 mM HEPES pH 7.9, 5 mM MgCl$_2$, 0.1 mM EDTA, 50 mM NaCl, 1 mM dithiothreitol, 17% glycerol) supplemented with 0.8 mM imidazole. The beads were then washed twice with 9 column volumes of buffer D supplemented with 8 mM imidazole, twice with 5 column volumes of buffer D supplemented with 40 mM imidazole and twice with 5 column volumes of buffer D supplemented with 80 mM imidazole.

Two hundred ul of each fraction were assayed for ICAM-R immunoreactivity by enzyme linked immunofiltration assay (ELIPA) in a 96-well format as described by the manufacturer (Pierce). Purified monoclonal antibody ICR 4.2 (5 ug/ml) (see Example 13) was used as the primary detection agent and a purified goat anti-mouse horseradish peroxidase conjugate (Boehringer Mannheim Biochemicals) (1:500) was used as the secondary antibody. The assay was developed with the soluble substrate ABTS (Zymed) as recommended by the supplier and read using a Dynatech plate reader with a 410 nm test filter. The results showed that ICAM-R immunoreactivity was predominantly found in the first 40 mM imidazole wash.

Peak fractions from wtHis6, E37His6 and mock transfectants were concentrated about 6.5 fold using Centricon 30 (Amicon) centrifugation units. The resultant concentrates were adjusted to equal vols. (0.34 ml) using PBS-D. Control soluble ICAM-R (15 ug/ml) (Example 11) in carbonate buffer pH 9.6 or in buffer D with 40 mM imidazole were made up. Fifty ul of a protein solution was aliquoted per well of a 96-well plate (Immulon 4, Dynatech) to coat the wells which were then assayed for binding of SKW3 cells as described in Example 11 using untreated, PMA-treated and anti-CD18 monoclonal antibody (60.3) treated cells.

Preliminary results indicate that wild type histidine tagged protein (wtHis6) functions as an adhesive ligand for SKW3 cells.

EXAMPLE 13

Monoclonal antibodies specific for ICAM-R were generated from the fusion of NS-1 myeloma cells with spleen cells of Balb/c mice immunized with human cell lines that express ICAM-R. Monoclonal antibodies were generated from six different fusions designated fusions 26, 42, 43, 46, 56 and 63.

A. Immunization of Mice

For fusion 26, five 6 to 12-week old Balb/c mice (Charles River Biotechnical Services, Inc., Wilmington, Mass., IACUC #901103) were immunized with HL-60 cells to generate anti-ICAM-R monoclonal antibodies. Two Balb/c mice were bled retro-orbitally for the collection of preimmune serum on day 0. On day 2, each animal received a total of $6 \times 10^6$ HL-60 cells in 0.5 ml PBS (0.1 ml s.c. and 0.4 ml i.p.). A second immunization with $9.5 \times 10^6$ HL-60 cells was administered on day 28 in the same manner. Immune serum was collected via retro-orbital bleeding on day 35 and tested by FACS (FACS screening is described in detail in Section C below) to determine its reactivity to ICAM-R transfectants. Based on these results, both animals were immunized a third time on day 51 with $6.5 \times 10^6$ HL-60 cells and a fusion was performed with spleen cells sterilely removed from one animal (#764) on day 54.

For fusion 42, on day 0 each of five mice was prebled and then immunized i.p. with $5 \times 10^6$ SKW3 cells in 0.5 ml PBS containing 50 $\mu$g adjuvant peptide (Sigma). The mice were boosted in the same manner on days 21 and 42. Ten days after the third injection, the mice were bled and immune sera was tested by FACS. Mouse #843 was given a final boost of SKW3 cells on day 64. The spleen was sterilely removed three days later.

For fusion 43, on day 0 each of five mice was prebled and then immunized i.v. with $5 \times 10^6$ cells from the erythroleukemic cell line K562. Each mouse was given a daily i.p. injection of 1.5 mg cyclophosphamide in 150 $\mu$l for the next two days. On day 10, SKW3 cells plus adjuvant peptide were injected as in Fusion 42. On day 30, mice were given another cycle of K562 cells followed by cyclophosphamide. On day 42 mice were boosted with SKW3 cells with adjuvant peptide. Mice were bled on day 56 and immune sera was tested by FACS. Mouse #1021 was given a final boost of SKW3 cells and adjuvant peptide on day 78. The spleen was sterilely removed three days later.

For fusion 46, a mouse (#900) was immunized as described for fusion 42. On day 128, the mouse was given a final boost of approximately $4 \times 10^6$ *Macaca nemestrina* spleen cells. The single cell suspension of monkey spleen was prepared as described below in the following paragraph. The monkey cells were pelleted and resuspended in erythrocyte lysis buffer: 0.15M $NH_4Cl$, 1M $KHCO_3$, 0.1 mM $Na_2$ EDTA, pH 7.2–7.4. After lysing the erythrocytes, the splenocytes were washed twice in RPMI and once in PBS. Finally, the cells were resuspended in 400 $\mu$l PBS containing 50 $\mu$g adjuvant peptide and injected. The mouse spleen was removed sterilely three days later.

For fusions 56 and 63, mice (#845 and #844) were immunized as described for fusion 42, except that no boost of SKW3 cells was given on day 64. Instead, these mice were given additional immunizations of SKW3 cells in PBS with adjuvant peptide on days 158 and 204 and were given i.p. injections of *Macaca nemestrina* spleen cells in 0.5 ml PBS containing 50 $\mu$g adjuvant peptide on days 128 and 177. For fusion 56, mouse #845 was injected with 2.24 $\mu$g soluble ICAM-R (Example 11) in 700 $\mu$l PBS, 100 $\mu$l was given i.v. with the remainder given i.p. The spleen was sterilely removed four days later. For fusion 63, mouse #844 was immunized on day 226 with *Macaca nemestrina* spleen cells as described for fusion 56 and on day 248 with 50 $\mu$g soluble ICAM-R in 100 $\mu$l complete Freuds adjuvant given s.c. The mouse received a final boost i.v. of 66 $\mu$g soluble ICAM-R in 100 $\mu$l PBS. The spleen was removed sterilely four days later.

B. Fusions

Briefly, a single-cell suspension was formed from each mouse spleen by grinding the spleen between the frosted ends of two glass microscope slides submerged in serum free RPMI 1640 (Gibco), supplemented with 2 mM L-glutamine, 1 mM sodium pyruvate, 100 units/ml penicillin, and 100 $\mu$g/ml streptomycin (Gibco). The cell suspension was filtered through sterile 70 mesh Nitex cell strainer (Becton Dickinson, Parsippany, N.J.), and washed twice by centrifuging at 200 g for 5 minutes and resuspending the pellet in 20 ml serum free RPMI. Thymocytes taken from three naive Balb/c mice were prepared in a similar manner.

NS-1 myeloma cells, kept in log phase in RPMI with 11% fetal bovine serum (FBS) or Fetalclone (Hyclone) for three days prior to fusion, were centrifuged at 200 g for 5 minutes, and the pellet was washed twice as described in the foregoing paragraph. After washing, each cell suspension was brought to a final volume of 10 ml in serum free RPMI, and 10 $\mu$l was diluted 1:100. Twenty $\mu$l of each dilution was removed, mixed with 20 $\mu$l 0.4% trypan blue stain in 0.85% saline (Gibco), loaded onto a hemacytometer (Baxter Healthcare Corp. Deerfield, Ill.) and counted.

A sample of $2 \times 10^8$ spleen cells was combined with $4 \times 10^7$ NS-1 cells, centrifuged and the supernatant was aspirated. The cell pellet was dislodged by tapping the tube and 2 ml of 37° C. PEG 1500 (50% in 75 mM Hepes, pH 8.0) (Boehringer) was added with stirring over the course of 1 minute, followed by adding 14 ml of serum free RPMI over 7 minutes. An additional 16 ml RPMI was added and the cells were centrifuged at 200 g for 10 minutes. After discarding the supernatant, the pellet was resuspended in 200 ml RPMI containing 15% FBS or Fetalclone, 100 $\mu$M sodium hypoxanthine, 0.4 $\mu$M aminopterin, 16 $\mu$M thymidine (HAT) (Gibco), 25 units/ml IL-6 (Boehringer) and $1.5 \times 10^6$ thymocytes/ml. The suspension was dispensed into ten 96-well flat bottom tissue culture plates at 200 $\mu$l/well. Cells in plates were fed three times typically on 2, 4, and 6 days post fusion by aspirating approximately 100 $\mu$l from each well with an 18 G needle (Becton Dickinson), and adding 100 $\mu$l/well plating medium described above except containing 10 units/ml IL-6 and lacking thymocytes.

C. Screening

When cell growth reached 60–80% confluency (day 8–10), culture supernatants were taken from each well of Fusions 26 and 42, pooled by column or row and analyzed by. FACS on parental L cells (Fusion 26) or parental CV-1 cells (Fusion 42); (negative control) and on L cells (Fusion 26) or CV-1 cells (Fusion 42) transfected with ICAM-R DNA. Briefly, transfected and nontransfected L cells or CV-1 cells were collected from culture by EDTA (Versene) treatment and gentle scraping in order to remove the cells from the plastic tissue culture vessels. Cells were washed two times in Dulbecco's PBS with $Ca^{2+}$ and $Mg^{2+}$, one time in "FA Buffer" (either D-PBS or RPMI 1640, 1% BSA, 10 mM NaN$_3$), and dispensed into 96-well round bottomed plates at 1.5–2.0×10$^5$ cells/100 µl FA Buffer per well. At this point, the assay was continued at 4° C. Cells were pelleted by centrifugation in a clinical centrifuge at 4° C. The supernatant from each well was carefully suctioned off, the pellets were broken up by gently tapping all sides of the assay plate. One hundred µl of hybridoma supernatant pool was added per well using a 12-channel pipetman. Each monoclonal antibody-containing supernatant pool was incubated for 1 hour on both parental and transfected cells at 4° C. Assay plates were then washed 2 times with FA Buffer as above. The last wash was replaced with a 50 µl/well of a 1:100 dilution of a F(ab')$_2$ fragment of sheep anti-mouse IgG (whole molecule)-FITC conjugate (Sigma) prepared in FA Buffer. Assay plates were incubated at 4° C. protected from light for 45 minutes. The assay plates were then washed 2 times with D-PBS containing NaN$_3$ only (i.e., no BSA) in the same manner as before and the last wash was replaced with 200 µl/well 1% paraformaldehyde in D-PBS. Samples were then transferred to polystyrene tubes with the aid of a multichannel pipet for flow cytometric analysis (FACS) with a Becton Dickinson FACscan analyzer.

Fusions 43 and 46 were screened initially by antibody capture ELISA, testing for the presence of mouse IgG in hybridoma supernatants. Immunlon 4 plates (Dynatech, Cambridge, Mass.) were coated at 4° C. with 50 µl/well goat anti-mouse IgA, IgG or IgM (Organon Teknika Corp., Durham, N.C.) diluted 1:5000 in 50 mM carbonate buffer, pH 9.6. Plates were washed 3 times with PBS with 0.05% Tween 20 (PBST) and 50 µl culture supernatant was added. After incubation at 37° C. for 30 minutes, and washing as above, 50 µl of horseradish peroxidase conjugated goat anti-mouse IgG(fc) (Jackson ImmunoResearch, West Grove, Pa.) diluted 1:3500 in PBST was added. Plates were incubated as above, washed 4 times with PBST and 100 µl substrate, consisting of 1 mg/ml o-phenylene diamine (Sigma) and 0.1 µl/ml 30% H$_2$O$_2$ in 100 mM Citrate, pH 4.5, was added. The color reaction was stopped in 5 minutes with the addition of 50 µl of 15% sulfuric acid. A$_{490}$ was read on an automatic plate reader.

Fusions 56 and 63 were screened initially by antigen capture ELISA. Immulon 4 plates (Dynatech) were coated at 4° C. overnight with 100 ng 26E3D Fab' (see Section F below) per well, diluted in 50 mM carbonate buffer. The plates were blocked with 100 µl/well 2% BSA in PBS for 1 hour at ambient temperature. After the plates were aspirated, culture supernatant containing soluble ICAM-R was diluted 1:8 in PBST and added at 50 µl/well. After 1 hour incubation at ambient temperature, the wells were washed three times with PBST, hybridoma culture supernatant was added at 50 µl/well, and the plates were again incubated as above. The plates were washed 3 times and 50 µl/well peroxidase conjugated goat anti-mouse IgG diluted 1:3500 in PBST was added. The remainder of the assay was performed as described in the foregoing paragraph.

D. Subcloning

Supernatants from individual wells representing the intersection points of positive columns and rows (Fusions 26 and 42), individual wells producing IgG (Fusions 43 and 46), or wells reactive with soluble ICAM-R (Fusions 56 and 63) were rescreened by FACS the following day. L cells or L cells transfected with ICAM-R DNA were used for screening Fusion 26 antibodies and CV-1 cells or CV-1 cells transfected with ICAM-R DNA were used for screening antibodies from Fusions 42, 43, 46, 56 and 63. Twenty-nine wells (designated 26E3D-1, 26E3E, 26H3G, 26H11C-2, 26I8F-2, 26I10E-2, 26I10F, 42C5H, 42D9B, 43H7C, 46D7E, 56D3E, 56I4E, 63A10E, 63C3F, 63C11A, 63E9G, 63E12C, 63G3G, 63H6H, 63H9H, 63I1C, 63I6G, 63I12F, 63G4D, 63E11D, 63H4C, showed preferential staining of the ICAM-R transfectants versus the control cells. These wells were subcloned two to three times, successively, by doubling dilution in RPMI, 15% FBS, 100 µM sodium hypoxanthine, 16 µM thymidine, and 10 units/ml IL-6 (Boehringer). Wells of subclone plates were scored visually after 4 days and the number of colonies in the least dense wells were recorded. Selected wells of the each cloning were tested by FACS after 7–10 days. Activity was retained in fifteen cell lines which were deposited with the ATCC [26E3D-1 (ATCC HB 11053), 26H11C-2 (HB 11056), 26I8F-2 (HB 11054), 26I10E-2 (ATCC HB 11055), 42C5H (ATCC HB 11235), 42D9B (ATCC HB 11236), 43H7C (ATCC HB 11221), 46D7E (ATCC HB 11232) and 46I12H (ATCC HB 11231), 63E11D (ATCC HB 11405), 63G4D (ATCC HB 11409), 63H4C (ATCC HB 11408), 63H6H (ATCC HB 11407), 63I1C (ATCC HB 11406) and 63I6G (ATCC HB 11404). In the final cloning, positive wells containing single colonies were expanded in RPMI with 11% FBS. Names assigned to the monoclonal antibodies produced by the hybridomas are presented in Table 4 in Example 14.

E. Characterization

The monoclonal antibodies produced by above hybridomas were isotyped in an ELISA assay. Immulon 4 plates (Dynatech) were coated at 4° C. with 50 µl/well goat anti-mouse IgA, IgG or IgM (Organon Teknika) diluted 1:5000 in 50 mM carbonate buffer, pH 9.6. Plates were blocked for 30 minutes at 37° C. with 1% BSA in PBS, washed 3 times with PBS with 0.05% Tween 20 (PBST) and 50 µl culture supernatant (diluted 1:10 in PBST) was added. After incubation and washing as above, 50 µl of horseradish peroxidase conjugated rabbit anti-mouse IgG$_1$, G$_{2a}$, G$_{2b}$ or G$_3$ (Zymed) diluted 1:1000 in PBST with 1% normal goat serum was added. Plates were incubated as above, washed 4 times with PBST and 100 µl substrate, consisting of 1 mg/ml o-phenylene diamine (Sigma) and 0.1 µl/ml 30% hydrogen peroxide in 100 mM Citrate, pH 4.5, was added. The color reaction was stopped in 5 minutes with the addition of 50 µl of 15% sulfuric acid. A$_{490}$ was read on a plate reader. The isotypes of the monoclonal antibodies are give in Table 11 in Example 21.

Figure 5:
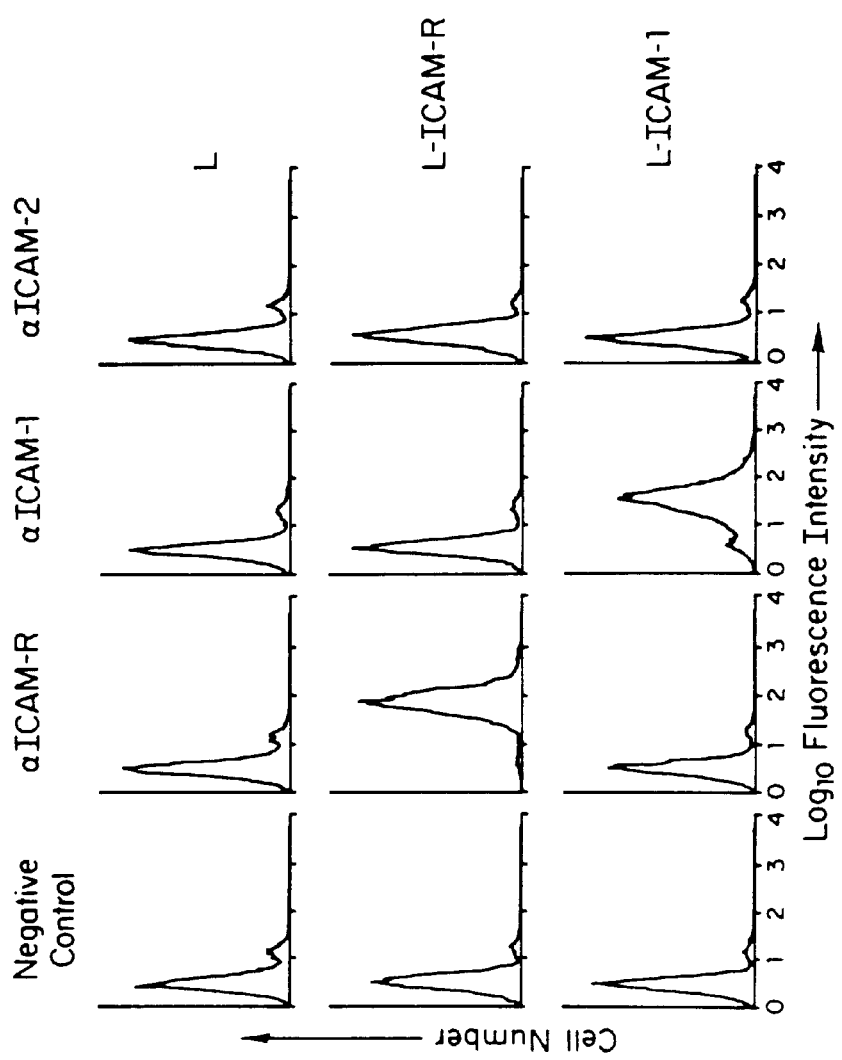
FIG. 5 illustrates in histogram format the results of FACS analyses of indirect immunofluorescence staining of transfected L cells using monoclonal antibodies specific for ICAM-R, ICAM-1 or ICAM-2.

FACS analyses of indirect immunofluorescence staining of control cells and cells transfected with ICAM-R or ICAM-1 DNA using monoclonal antibodies against ICAM-R, ICAM-1 and ICAM-2 were performed. Staining was carried out as described for FACS analyses in Example 13C using either 0.1 ml hybridoma culture supernatant (anti-ICAM-R) or 1 µg pure monoclonal antibody (anti-ICAM-1 or ICAM-2) per 5×10$^5$ cells. Results of the analyses are presented as histograms (representing 10$^4$ cells analyzed) in FIG. 5. Anti-ICAM-R antibodies specifically bound to L cells transfected with ICAM-R cDNA, but not to parental or ICAM-1 transfected L cells. ICAM-R transfectants did not react with antibodies against ICAM-1 (Mab LB2 from Edward Clark, University of Washington) or ICAM-2 (IC2/2, Biosource Genetics Corp., Vacaville, Calif.).

FACS analysis of indirect immunofluorescence of *Macaca fascicularis*, porcine or canine peripheral blood leukocytes was performed using the anti-ICAM-R monoclonal antibodies. Twenty ml of heparinized *Macaca fascicularis* blood or porcine blood was diluted with 280 ml of erythrocyte lysis buffer, incubated 3–5 minutes at room temperature, and centrifuged at 200 g for 5 minutes. The supernatant was discarded. The pellet was washed once in cold D-PBS containing 2% fetal bovine serum and the cells were counted by hemacytometer. Twenty ml of heparinized canine blood was diluted in two volumes of Waymouth's medium (Gibco) plus 2% nonessential amino acids (NEAA). Each 5 ml of blood solution was layered over 4 ml of Histopaque (Sigma) and centrifuged at 1000 g for 20 minutes at room temperature. Cells were collected from the interface, washed once in Waymouth's medium plus 2% NEAA, and counted as above. Each cell population was stained as described previously in Example 13C and analyzed by FACS. Anti-ICAM-R antibodies produced by hybridoma cell lines 26I10E, 46I12H, 63H4C, 56I14E and 63I12F specifically stained monkey PBL while the other antibodies did not. None of the antibodies specifically stained canine or porcine PBL. The monoclonal antibodies produced by the hybridoma cell lines 63A10E, 63E9G, 63E12C, 63G3G and 63H9H were not tested.

F. Purification

Hybridoma culture supernatants containing the anti-ICAM-R monoclonal antibodies listed in Table 11 in Example 21 were adjusted to 1.5M glycine, 3.0M NaCl, pH 8.9, and put over a 2 ml bed volume protein A column (Sigma). After washing with 1.5M glycine, 3M NaCl, pH 8.9, the column was eluted with 100 mM sodium citrate, pH 4.0. One ml fractions were collected into 100 µl of 1.5M Tris, pH 8.8. Fractions containing antibody as determined by $A_{280}$ were pooled and dialyzed against PBS.

G. Affinity

Nine of the purified anti-ICAM-R monoclonal antibodies were diluted serially and assayed in an ELISA format for binding to a fixed amount of soluble ICAM-R (Example 11) coated onto plastic. The results of the assay are presented in Table 3 below wherein high affinity binding was defined as 50% maximal binding at a monoclonal antibody concentration of less than 1 µg/ml and low affinity binding was defined as 50% maximal binding at a monoclonal antibody concentration of greater than 1 µg/ml.

TABLE 3

| Monoclonal Antibody Produced By | Affinity |
| --- | --- |
| 26E3D | Low |
| 26H11C | High |
| 26I8F | High |
| 26I10E | Low |
| 42C5H | Low |
| 42D9B | Low |
| 43H7C | Low |
| 46D7E | High |
| 46I12H | Low |

F. Fab' Fragments Production

Fab' fragments were generated from the monoclonal antibodies produced by hybridomas 26E3D, 26I10E, 42D9B, 43H7C and 46D7E by the method described in Johnstone et al., p. 52 in Blackwell, *Immunochemistry in Practice*, Oxford Press (1982).

EXAMPLE 14

The ICAM-R specific monoclonal antibodies listed in Table 11 in Example 21 were tested for their ability to inhibit binding of JY cells (CD18$^+$) to recombinant soluble human ICAM-R. Adhesion assays were performed as described in Example 12. Cells were treated with PMA and antibodies were then added at a final concentration of 10 µg/ml. Data was collected from triplicate wells during three independent experiments. Total CD18-dependent binding was determined as the amount of adhesion blocked by a control anti-CD18 monoclonal antibody 60.3. The percentage of total CD18-dependent binding that was inhibited by each monoclonal antibody is shown below in Table 4 wherein the names assigned to monoclonal antibodies produced by each hybridoma are given. The monoclonal antibody names are used throughout the following examples instead of hybridoma designations.

TABLE 4

| Hybridoma | Monoclonal Antibody | Inhibition (%) | Standard Error |
| --- | --- | --- | --- |
| — | 60.3 | 100 | 20 |
| 26E3D | ICR-1.1 | 45 | 10 |
| 26H11C | ICR-2.1 | 5 | 7 |
| 26I8F | ICR-3.1 | 40 | 9 |
| 26I10E | ICR-4.2 | 3 | 12 |
| 42C5H | ICR-5.1 | 25 | 10 |
| 42D9B | ICR-6.2 | 2 | 5 |
| 43H7C | ICR-7.1 | 10 | 15 |
| 46D7E | ICR-8.1 | 75 | 10 |
| 46I12H | ICR-9.2 | 2 | 10 |
| 63E11D | ICR-12.1 | 20 | 8 |
| 63G4D | ICR-13.1 | 15 | 20 |
| 63H4C | ICR-14.1 | 70 | 13 |
| 63H6H | ICR-15.1 | 43 | 15 |
| 63I1C | ICR-16.1 | 46 | 13 |
| 63I6G | ICR-17.1 | 68 | 15 |

EXAMPLE 15

FACS-based competition assays utilizing human peripheral blood leukocytes or SKW3 cells (both ICAM-R expressing cells) indicate that monoclonal antibodies ICR-4.2 and ICR-1.1 are immunologically reactive with distinct epitopes of ICAM-R.

In the assays, human peripheral blood leukocytes (PBL) obtained by Ficoll Hypaque centrifugation of normal peripheral blood were washed twice in ice cold FACS buffer (PBS containing 0.1% sodium azide and 1% bovine serum albumin) and $2 \times 10^5$ cells were incubated in triplicate polypropylene tubes with 5 µg of each of the following antibodies ICR-1.1, ICR-4.2, and control isotype IgG (Sigma). Al tubes containing the first stage antibodies were then incubated for 30 minutes at 4° C. and washed twice in cold FACS buffer. To each triplicate tube, 5 µg of each of the following second stage antibodies were added: biotinylated-ICR-1.1, biotinylated-ICR-4.2, biotinylated-anti-rat CD4 (negative control). AU second stage antibodies were biotinylated according to standard procedures as described in Example 13 and all tubes were then incubated for an additional 30 minutes at 4° C. before washing twice in FACS buffer. Five ul of a 1:10 dilution of Strepavidin-phycoerythrin (Southern Biotechnology, Birmingham, Ala.) was then added to each tube containing 50 ul FACS buffer and all tubes were incubated for 30 minutes at 4° C. Finally, all tubes were washed twice in FACS buffer and analyzed by flow cytometry (FACScan, Becton-Dickinson).

While monoclonal antibody ICR-4.2 blocked binding of biotinylated-ICR-4.2 to ICAM-R on PBL, it did not block binding of monoclonal antibody ICR-1.1. Similarly, monoclonal antibody ICR-1.1 did block binding of biotinylated-ICR-1.1 but did not block binding of monoclonal antibody ICR-4.2. These results indicate that the two antibodies recognize distinct epitopes on ICAM-R. Equivalent results were obtained when using the human cell line SKW3 as follows. SKW3 cells were labelled with either 1 µg of antibody ICR-1.1 or ICR-4.2, washed in FACS buffer and incubated with 1 μg biotinylated-ICR-1.1 or biotinylated ICR-4.2. All tubes were then washed in FACS buffer, incubated with Strepavidin-phycoerythrin for an additional 30 minutes at 4° C. and analyzed by FACScan.

In the assays, if an unlabelled antibody (the "blocking" antibody) prevented the labelled antibody from binding to ICAM-R, it indicates that the unlabelled antibody "competes" with the labelled antibody for binding to ICAM-R and that the two antibodies recognize the same, sequential or sterically overlapping epitopes on ICAM-R. A variation of the competition assay in which unlabelled antibody is used to "compete away" binding of a labelled antibody may also be utilized to determine if two antibodies recognize the same, sequential or sterically overlapping epitopes.

The specific ICAM-R epitopes recognized by the various monoclonal antibodies of the invention can be mapped by four different methods.

A. Epitope Mapping Using the Multipin Peptide Synthesis System

The first method for mapping linear epitopes recognized by the ICAM-R specific antibodies of the invention utilized the Multipin Peptide Synthesis System (Chiron Mimotopes Pty. Ltd., Victoria, Australia) which places ten amino acid peptides representing overlapping segments of the protein of interest on the surface of a series of plastic pins. A modified ELISA test is performed to determine binding of a monoclonal antibody to each peptide.

The ELISA to determine binding of the monoclonal antibodies to ICAM-R peptides was run as follows. The pins were placed in five 96-well plates containing 200 μl per well blocking buffer (2% weight/volume BSA, 0.1% volume/volume Tween 20, 0.01M PBS, pH 7.2) and incubated for one hour at 20° C. with agitation. The pins were transferred to plates with 175 μl per well of undiluted anti-ICAM-R monoclonal antibody supernatant and incubated overnight at 4° C. with agitation. The pins were then washed four times with 0.01M PBS, pH 7.2 (10 minutes/wash at 20° C. with agitation) and placed in plates containing 175 μl per well HRP-Goat anti-mouse IgG (H+L) (Kirkegaard and Perry Laboratory Inc., Gaithersburg, Md.) diluted to an appropriate concentration in conjugate diluent (1% volume/volume sheep serum, 0.1% volume/volume Tween 20, 0.1% weight/volume sodium caseinate and 0.01M PBS). The plates were agitated for one hour at 20° C., and washed four times with 0.01M PBS. The pins were transferred to plates containing ABTS substrate solution [0.5 mg/ml ABTS, 0.01% weight/volume $H_2O_2$ in substrate buffer (17.9 g/L $Na_2HPO_4$ $H_2O$, 16.8 g/L citric acid monohydrate, pH 4.0)] for 45 minutes at 20° C. with agitation and then the plates were read at 410/495 nm.

Relative reactivity with individual pins was determined after normalizing results for differences in immunoglobulin concentrations in anti-ICAM-R and control hybridoma supernatants and reactivities of positive controls between assays. Mouse IgG levels for each supernatant had been determined by antibody capture ELISA as follows. Immulon 4 plates were coated and washed as described in Example 13C. Fifty μl/well of culture supernatant diluted in PBST [or known concentrations in doubling dilutions in PBST of mouse $IgG_1$ and $IgG_{2a}$ (MOPC-21, and UPC-10) (Sigma)] was added to the plate. After incubating for 1 hour at room temperature and washing 3 times with PBST, horseradish peroxidase conjugated goat anti-mouse IgG(fc) (Jackson ImmunoResearch, West Grove, Pa.) was diluted 1:2000 for mouse $IgG_1$ and 1:1000 for $IgG_{2a}$, and added 50 μl/well. After the plate was incubated for 1 hour at room temperature and washed 4 times in PBST, the remainder of the assay was conducted as described in Example 13C. Antibody concentrations of culture supernatant were determined by fitting measured optical densities to the standard curve of the isotype matched control.

Strong reactivity of monoclonal antibody ICR-1.1 was noted with two overlapping peptides spanning amino acids 13–23, as illustrated below:

SEQ ID NO: 38
VLSAGGSLFV
SEQ ID NO: 39
LSAGGSLFVN

Regions reactive with anti-ICAM-R antibodies can also be defined and/or verified using the following methodologies.

B. Epitope Mapping Using a Library of Bacterial Clones

Epitope mapping with the anti-ICAM-R antibodies was also performed using the Novatope Library Construction and Screening System (Novagen, Madison, Wis.). Using this method, a library of bacterial clones is generated wherein each clone expresses a polypeptide including a small peptide derived from the protein being examined. The library is then screened by standard colony lift methods using monoclonal antibodies as probes.

Double-stranded DNA encoding the external domain of ICAM-R (amino acids 1 to 487) from pVZ147 (See Example 4) was cut with different amounts of DNAseI in the presence of 10 mM manganese for 10 minutes at 21° C. The reaction was stopped with EDTA and 1/10 of the reaction was electrophoresed on a 2% agarose gel with ethidium bromide and appropriate markers. Those reactions containing fragments in the 50–150 bp range were pooled and electrophoresed on another 2% gel. The area of the gel between 50–150 bp was excised, the fragments contained therein were electroeluted into dialysis tubing (SP Brand Spectra/Por 2, MWCO 12–14,000), and then phenol/chloroform extracted and ethanol precipitated.

One μg DNA was blunted according to the manufacturer's protocol, using T4 DNA polymerase and all four dNTPs. The reaction was stopped by heating to 75° C. for 10 minutes, then a single 3' dA residue was added by using Tth DNA polymerase (Novagen). The reaction was stopped by heating to 70° C. for 15 minutes and extracted with chloroform. When starting with 1 μg of DNA, the final concentration was 11.8 ng/μl in 85 μl. The dA tailed fragments are ligated into the pTOPE T-vector (Novagen) which is designed for the expression of inserts as stable fusion proteins driven by T7 RNA polymerase (the structural gene for which is carried on a replicon in the host cell). Using 6 ng of 100 bp DNA (0.2 pmol), the ligation reaction was run at 16° C. for 5 hours. NovaBlue(DE3) (Novagen) cells were transformed with 1 μl (1/10) of the reaction mix, and spread on LB agar (carbenicillin/tetracycline) plates to obtain an initial count of transformants. The remainder of the ligation reaction was put at 16° C. for an additional 16 hours. Based on the initial plating, 2 μl of the ligation reaction was used to transform 40 μl of competent NovaBlue(DE3) cells, then 8 plates were spread at a density of approximately 1250 colonies/plate for screening with antibody.

Colonies were screened using standard colony lift methods onto nitrocellulose membranes, lysed in a chloroform vapor chamber and denatured. Using anti-ICAM-R monoclonal antibody ICR-1.1 at a 1:10 dilution in TBST (Tris-buffered saline/Tween) as a primary antibody, the assay was developed using an alkaline phosphatase-coupled secondary reagent. The substrate mix was incubated for 30 minutes. One isolated colony gave a strong positive reaction. Three others areas (not isolated colonies) gave weak positive reactions. Streaks were made from a stab of the isolated colony or colony areas for re-screening. Upon re-probing with ICR-1.1, the streak from the isolated colony had positive reactive areas after a 20 minute incubation with substrate. The other three colony area samples were negative. A stab from the ICAM-R reactive area was re-streaked, incubated overnight at 37° C. and re-probed incubating with substrate for 10 minutes. Many ICR-1.1 reactive colonies resulted. Plasmid DNA recovered from these colonies can be sequenced and the amino acid sequence corresponding to the ICR-1.1 reactive epitope can be determined.

C(1). Epitope Mapping by Domain Substitution—Construction of Chimeric ICAM-R Molecules and Deletion Mutants Conformational epitopes of ICAM-R recognized by the monoclonal antibodies of the invention may be mapped by domain substitution experiments. In these experiments, chimeric variants of ICAM-R are generated in which selected immunoglobulin-like domains of ICAM-R are fused to portions of ICAM-1 and assayed for binding to the monoclonal antibodies of the invention by FACS.

Figure 7A:
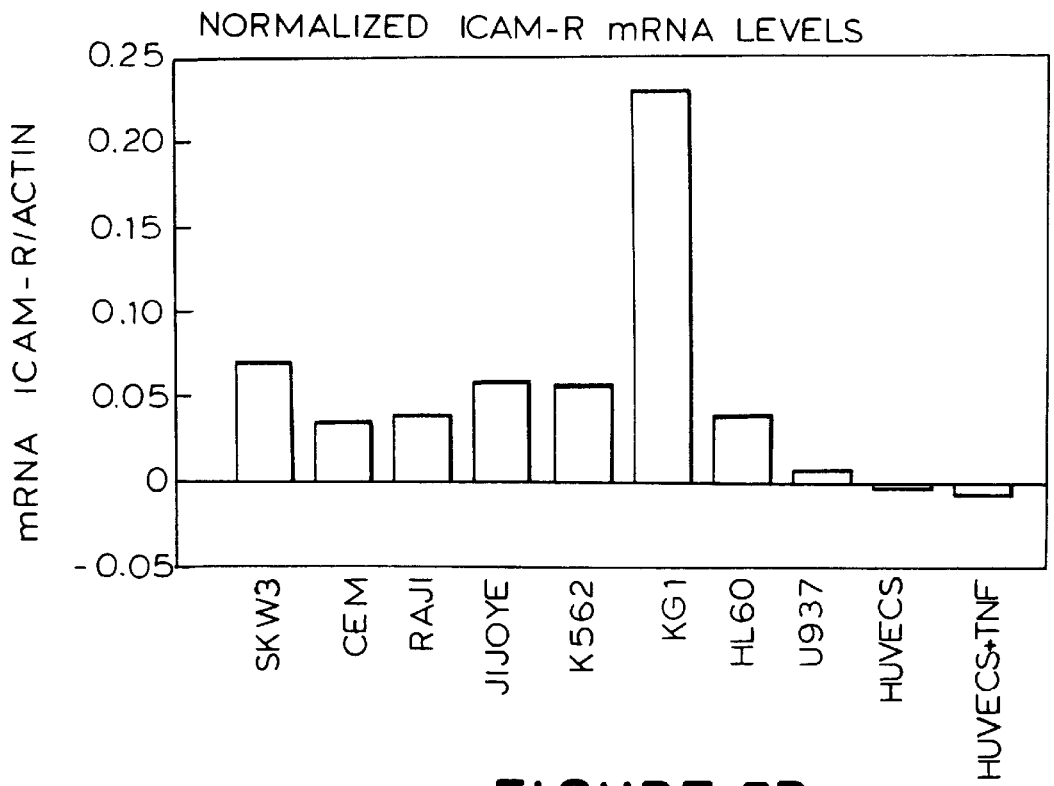
FIG. 7(A through B) presents bar graphs depicting the results of actin-normalized Northern blot hybridization of human leukocyte cell lines and umbilical cord endothelial cells using ICAM-R or ICAM-1 DNA probes.
Figure 7B:
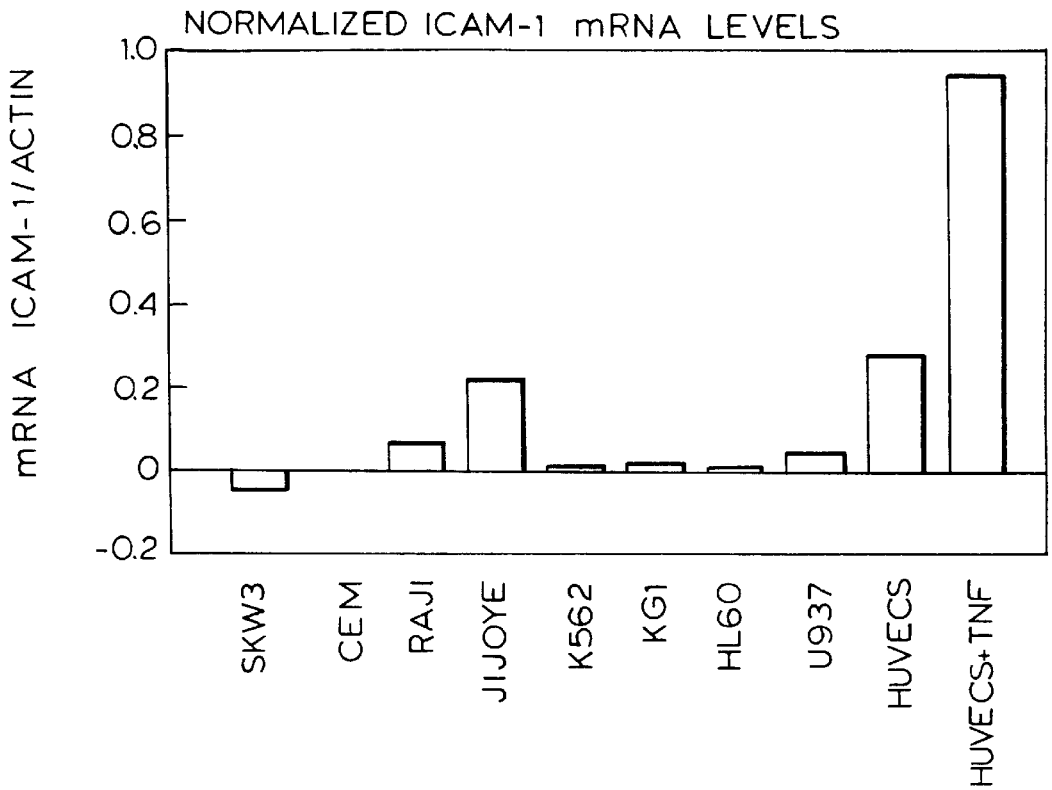

FIG. 7 is a diagram of the chimeric proteins whose construction is outlined below. Protein number 1 contains the amino-terminal immunoglobulin-like domain of ICAM-R (residues 1 to 93) fused to ICAM-1 (residue 117 to 532). Protein number 2 contains the first two amino terminal immunoglobulin-like domains of ICAM-R (residues 1 to 190) fused to ICAM-1 (residues 216 to 532). Protein number 3 contains the first three immunoglobulin-like domains of ICAM-R (residues 1 to 291) fused to ICAM-1 (residues 317 to 532).

Protein number 1 was made by engineering a unique Nhe I site into the coding sequences of ICAM-R and ICAM-1 at the junction of immunoglobulin-like domains 1 and 2 of each. The DNA sequence of ICAM-R was subcloned into the M13 BM21 vector (Boehringer) as described in Example 12 resulting in a molecule called M13 BM21ICAM-R. The entire coding sequence of ICAM-1 [Simmons et al., *Nature*, 331: 624–627 (1988)] was subcloned into the plasmid pBSSK(+) (Stratagene). The resulting plasmid, pBSSK(+)ICAM-1 was cut with SalI and KpnI to release the ICAM-1 coding sequence along with a short segment of the multiple cloning sites and ligated to M13 BM21 cut with restriction enzymes SalI and KpnI resulting in a molecule called M13 BM21ICAM-1. M13 phage isolates were verified by DNA sequence analysis.

Mutagenizing oligonucleotides ICAM1.D1.Nhe 1 (corresponding to nucleotides 426 to 393 of ICAM-1) and ICAMR.D1Nhe 1 (corresponding to nucleotides 367 to 393 of ICAM-R) having the following sequences were synthesized by routine laboratory methods:

ICAM1.D1.NheI (SEQ ID NO: 40)
AGAGGGGAGGGGTGCTAGCTCCACCCGTTCTGG
ICAMR.D1.NheI (SEQ ID NO: 41)
GAGCGTGTGGAGCTAGCACCCCTGCCT Nucleotides 16 and 19 of ICAM1.D1.NheI and nucleotide 15 of ICAMR.D1.NheI form mismatch base pairs when the oligos are annealed to their respective complementary DNA sequences. Both oligonucleotides introduce a recognition site for endonuclease Nhe I. Site-directed mutagenesis with the oligonucleotides was employed to introduce the sequences of these oligos into the respective ICAM-1 and ICAM-R target DNA sequences M13 BM21ICAM-1 and M13 BM21ICAM-R. Several phage isolates from each mutagenesis reaction were sequenced to verify that the correct DNA sequence was present. These isolates were designated M13 BM21ICAM-R.NheI and M13 BM21ICAM-1.NheI.

The coding region for the ICAM-R signal peptide and immunoglobulin-like domain 1 was isolated from M13 BM21ICAM-R.NheI by the following method. Ten μg of purified single strand M13 BM21ICAM-R.NheI phage DNA was annealed to 50 ng Lac Z universal −20 primer (SEQ ID NO: 35 in 1×Klenow DNA polymerase buffer (10 mM Tris-Cl pH 7.5, 5 mM MgCl$_2$, 7.5 mM dithiothreitol) by incubating the mix at 65° C. for 5 minutes and then 25° C. for 5 minutes. The following mixture was then added to the annealing reaction: 33 μM final concentration dATP, dGTP, dCTP, dTTP; 4 units of Klenow DNA polymerase (Boehringer), and 1×Klenow buffer. The primer extension reaction was allowed to incubate at 37° C. for 45 minutes prior to being stopped by a single phenol/chloroform (1:1) extraction and ethanol precipitation. The dried pellet was resuspended in 1×EcoRI buffer and 20 units each of EcoRI and NheI endonucleases were added prior to a 60 minute incubation at 37° C. A 412 bp fragment containing the coding sequence for ICAM-R signal peptide and immunoglobulin-like domain 1 was agarose gel purified.

The DNA sequence of ICAM-1 containing the coding region for immunoglobulin-like domains 2 through 5, the transmembrane and cytoplasmic domains was isolated by restriction enzyme digest. Ten μg of primer extended M13.BM21ICAM-1.NheI were cut with NheI and NotI. This resulted in the release of a DNA fragment of 1476 bp which was agarose gel purified.

Five μg of the mammalian expression plasmid pcDNAI/Amp (Invitrogen) was digested with EcoRI and NotI and purified by spin column chromatography. A 20 μl ligation mix was assembled containing the following components: 50 ng linear pCDNA1Amp with EcoRI and NotI termini, 100 ng of the 412 bp ICAM-R fragment, 100 ng of the 1476 bp ICAM-1 fragment, 1×ligase buffer and 1 unit of T4 DNA ligase (Boehringer). The reaction was incubated at 25° C. for 16 hours and used to transform competent XL-1 cells (Biorad). Transformants were selected on LB plates supplemented with carbenicillin at a final concentration of 100 μg/ml. Transformants were analyzed using a standard mini DNA prep procedure and digestion with diagnostic endonucleases. Isolates designated pCDNA1Amp.RD1.ID2-5 were chosen for expression studies.

A chimeric gene encoding protein number 1 was also generated by an alternative method as follows. An appoximately 375 bp EcoRI-NheI fragment of ICAM-R containing domain 1 and an approximately 1500 bp NheI-NotI fragment of ICAM-1 containing the extracellular domains 2–5, the transmembrane domain and the cytoplasmic tail were gel purified after restriction enzyme digestion of the double stranded RF (replicative form) DNA from the M13BM21ICAM-R and M13 BM21ICAM-1 clones and agarose gel electrophoresis of the corresponding double stranded plasmid DNAs. The resulting two DNA fragments were cloned by a three way ligation into an EcoRI and NotI digested and calf intestinal phosphatase-treated expression vector pcDNAI/Amp (Invitrogen). *E. coli* XL1 blue (Stratagene) strain was transformed with the ligation mixture and the transformants were selected on carbenicillin containing plate. Clones with the desired inserts were identified by restriction enzyme digestion of the plasmid DNA minipreps.

To construct coding sequences for proteins 2 and 3, engineered versions of M13 BM21ICAM-1 and M13 BM21ICAM-R in which a unique NheI site was created between immunoglobulin-like domains 2 and 3 or a unique AflII site was created between immunoglobulin-like domains 3 and 4 were generated by methods similar to those described in the foregoing paragraphs. Four oligonucleotides (ICAM-1.D2.NheI corresponding to nucleotides 686 to 713 of ICAM-1, ICAM-R.D2.NheI corresponding to nucleotides 655 to 690 of ICAM-R, ICAM-1.D3.AflII corresponding to nucleotides 987 to 1026 of ICAM-1, and ICAM-R.D3.AflII corresponding to nucleotides 962 to 993 of ICAM-R) with the sequences set out below were synthesized for this purpose.

ICAM-1.D2.NheI (SEQ ID NO: 42)
GGGGGAGTCGCTAGCAGGACAAAGGTC
ICAM-R.D2.NheI (SEQ ID NO: 43)
CGAACCTTTGTCCTGCTAGCGAC-CCCCCCGCGCCTC
ICAM-1.D3.AflII (SEQ ID NO: 44)
TGAGACCTCTGGCTTCCTTAAGAT-CACGTTGGGCGCCGG
ICAM-R.D3.AflII (SEQ ID NO: 45)
GACCCATTGTGAACTTAAGCGAGCCCACC

Nucleotide 13 of ICAM-1.D2NheI; nucleotides 17, 18 and 20 of ICAMR.D2.NheI; nucleotides 17, 18, 20 and 22 of ICAM-1.D3. AflII; and nucleotides 15 and 17 of ICAM-R.D3.AflII form mismatch base pairs when the oligonucleotides are annealed to their respective complementary DNA sequences. The appropriate coding sequences of ICAM-R and ICAM-1 (sequences encoding the first two amino terminal immunoglobulin-like domains of ICAM-R fused to sequences encoding ICAM-1 residues 118 to 532 for protein 2 and sequences encoding the first three immunoglobulin-like domains of ICAM-R fused to sequences encoding ICAM-1 residues 317 to 532 for protein 3) were then subcloned into expression plasmid pCDNA1Amp (Invitrogen) to generate isolates pCDNA1Amp.RD1-2.1D3-5 and pCDNAAmp.RD1-3.1D4-5 respectively encoding ICAM-R variant proteins 2 and 3.

Gene fusions encoding protein numbers 2 and 3 were also constructed by alternative methods as follows.

For the generation of protein 2 encoding sequences, an NheI was introduced by oligonucleotide directed in vitro mutagenesis in between domains 2 and 3 in both ICAM-R and ICAM-1. An approximately 700 bp EcoRI-NheI fragment of ICAM-R containing the domains 1 and 2, and an approximately 1100 bp NheI-NotI fragment of ICAM-I containing the domains 3–5, the transmembrane domain and the cytoplasmic tail were subcloned by a three-way ligation into the EcoRI and NotI digested and calf intestinal phosphatase-treated pCDNAI/Amp plasmid DNA. For the generation of protein 3 encoding sequences an approximately 1000 bp NotI-AflII fragment of ICAM-R containing domains 1 through 3, and an approximately 850 bp AflII-NotI fragment of ICAM-1 containing domains 4–5, the transmembrane domain and the cytoplasmic tail were purified by restriction enzyme digestion of the plasmid DNAs and agarose gel electrophoresis. These two fragments were cloned by a three way ligation into the NotI digested and phosphatase treated pCDNAI/Amp plasmid DNA. Clones containing the insert with the desired orientation were identified by restriction enzyme digestion of plasmid DNA mini preparations.

ICAM-R domain deletion mutants were generated by similar oligonucleotide directed mutagenesis protocols as described above for chimeric protein numbers 1, 2 and 3. A domain 1 deletion mutant which lacks amino acids 2–90 of ICAM-R (SEQ ID NO: 1), a domain 1 and 2 deletion mutant which lacks amino acids 2–203, and a domain 3 deletion mutant lacking amino acids 188–285 were constructed.

Control plasmids containing the full length ICAM-R or ICAM-1 cDNA sequences were generated by ligating gel-purified cDNA fragments to plasmid pCDNA1Amp. The two plasmids pCDNA1AmpICAM-1 and pCDNA1AmpICAM-R express the full length ICAM-1 and ICAM-R proteins, respectively, so that monoclonal antibody binding to native protein in equivalent cellular contexts can be assessed.

COS cells were transfected with the plasmid DNA encoding the ICAM-R chimeric or deletion mutant proteins or with the plasmid DNA pCDNA1AmpICAM-1, pCDNA1AmpICAM-R or pCDNA1Amp by the DEAE-dextran method. Typically, the COS cells were seeded at a density of about $7.0 \times 10^5$ cells on a 10 cm diameter plate and grown overnight in Dulbecco's modified Eagles medium (DMEM) containing 10% fetal bovine serum (FBS). The next day the cell monolayer was rinsed with DMEM and exposed to 10 ml of transfection mixture containing 10 ug of the desired plasmid DNA, 0.1M chloroquine and 5.0 mg DEAE-dextran in DMEM for 2.5 hours at 37° C. After the incubation, the transfection mixture was aspirated and the monolayer was treated with 10% DMSO in PBS for one minute. The cells were washed once with DMEM and incubated with DMEM containing 10% FBS. The next day the medium was replaced with fresh medium and the incubation was continued for two more days.

Expression of all the chimeric and deletion mutant ICAM-R proteins except the domain 1 and 2 deletion mutant was obtained. The domain 1 and domain 3 deletion mutants expressed at a level of 50–60% compared to the wild type ICAM-R protein.

C(2). Epitope Mapping by Domain Substitution—Monoclonal Antibody Binding Assay

For the anti-ICAM-R monoclonal antibody binding assay, COS cells transfected with constructs encoding the ICAM-R chimeric proteins or control constructs were removed from the plates by EDTA treatment and aliquoted at $2.5 \times 10^5$ cells per well in a 96-well round bottom plate. Cells were washed 3 times with ice cold washing buffer (PBS containing 1% BSA and 0.05% sodium azide). Anti-ICAM-R monoclonal antibody was applied at 5.0 ug/ml in 50 ul final volume and incubated on ice for 30 minutes. Cells were then washed three times with cold washing buffer and incubated with the FITC labeled secondary antibody (sheep anti-mouse IgG F(ab')$_2$ at a 1:100 dilution on ice for 30 minutes in dark in 50 ul final volume. After the incubation, cells were washed again for three times in the ice cold washing buffer and resuspended in 200 ul of 1% paraformaldehyde. The samples were analyzed on a Becton-Dickinson FACScan instrument. Results of the assay are given below in Table 5 as percent positive COS cell transfectants, wherein MOPC 21 (IgG1) and UPC 10 (IgG2a) are isotype matched controls, 18E3D is an ICAM-1 specific monoclonal antibody and ICR-1.1 to ICR-9.2 are ICAM-R specific monoclonal antibodies. The reactivities of monoclonal antibodies ICR-1.1 through ICR-9.2 were assayed in a different experiment than monoclonal antibodies ICR-12.1 through ICR-17.1.

TABLE 5

| Antibody | Protein 1 | Protein 2 | Molecule Protein 3 | ICAM-R | ICAM-1 |
|---|---|---|---|---|---|
| MOPC 21 | 1.16 | 1.90 | 1.86 | 1.41 | 1.45 |
| UPC 10 | 2.00 | 1.41 | 1.69 | 1.67 | 1.04 |
| 18E3D | 1.24 | 1.23 | 1.14 | 1.60 | 39.99 |
| ICR-1.1 | 60.27 | 68.32 | 52.71 | 54.33 | 2.43 |
| ICR-2.1 | 50.77 | 60.06 | 43.97 | 49.50 | 1.94 |
| ICR-3.1 | 56.73 | 63.09 | 47.78 | 50.13 | 1.90 |

TABLE 5-continued

| Antibody | Protein 1 | Protein 2 | Molecule Protein 3 | ICAM-R | ICAM-1 |
|---|---|---|---|---|---|
| ICR-4.2 | 1.80 | 55.38 | 42.05 | 44.40 | 1.47 |
| ICR-5.1 | 58.30 | 62.38 | 48.43 | 48.42 | 1.85 |
| ICR-6.2 | 2.36 | 52.55 | 42.48 | 41.28 | 1.19 |
| ICR-7.1 | 47.54 | 41.76 | 37.78 | 38.33 | 1.43 |
| ICR-8.1 | 57.34 | 64.25 | 44.93 | 48.85 | 1.08 |
| ICR-9.2 | 2.12 | 66.84 | 46.64 | 50.69 | 2.39 |
| ICR-12.1 | 70.73 | 71.73 | 55.14 | 58.92 | ND |
| ICR-13.1 | 72.22 | 71.43 | 58.66 | 56.92 | ND |
| ICR-14.1 | 72.40 | 70.45 | 54.51 | 56.60 | ND |
| ICR-15.1 | 72.64 | 73.91 | 58.83 | 55.69 | ND |
| ICR-16.1 | 72.59 | 74.09 | 55.01 | 59.06 | ND |
| ICR-17.1 | 72.00 | 74.87 | 57.81 | 54.10 | ND |

The results presented above show that the antibodies ICR-1.1, 2.1, 3.1, 5.1, 7.1, 8.1, 12.1, 13.1, 14.1, 15.1, 16.1 and 17.1 recognize the hybrid molecule in which only the ICAM-1 domain 1 has been replaced with the ICAM-R domain 1. The antibodies ICR-4.2, 6.2 and 9.2 recognize the molecule in which a minimum of 2 domains (domain 1 and 2) of ICAM-1 was replaced with the corresponding domains of ICAM-R. Based on these results the antibodies have been categorized as either domain 1 or domain 2 specific.

The ICAM-R chimeric and deletion mutant protein constructs can also be used to transfect rat L cells by a calcium phosphate coprecipitate protocol using 10 μg of 2×CsCl-banded plasmid DNA. In this protocol, forty-eight hours post-transfection the cells are released from the dishes by mild trypsinization. The cells are divided and incubated on ice with anti-ICAM-R monoclonal antibodies or a control isotype matched monoclonal antibody at a concentration of 10 μg/ml or no monoclonal antibody for 1 hour. The cells are then processed for FACS analysis as previously described in Example 13C.

D. Epitope Mapping by Amino Acid Substitution

Differential reactivity of an anti-ICAM-R antibody of the invention with the ICAM-R variant proteins as described above thus is indicative of reactivity with a specific domain of ICAM-R. Once particular domains are identified that reacted with specific anti-ICAM-R monoclonal antibodies, individual residues within those domains are changed by olgo-directed site specific mutagenesis to determine their relative effects on monoclonal antibody binding. Based on computer algorithms that predict protein hydropathy and secondary structure (Kyte et al., supra), particular residues that have the potential for antibody interactions are targeted for mutagenesis.

Mutagenesis of ICAM-R was carried out according to the procedure of Kunkel et al., supra. E. coli strain Cj236 (dut ung) was transformed with the plasmid pCDNA1/AmpICAM-R (see Section C above) by electroporation. The transformants were selected on carbenicillin containing plate. One of the transformants was infected with the helper phage M13K07 and grown overnight. Uracil-containing single stranded DNA was prepared from the culture supernatant and used for mutagenesis. Mutagenic oligonucleotides were hybridized to the uracil containing single stranded DNA of pCDNA1/Amp-ICAM-R. Using the mutagenic oligonucleotides as primers, DNA synthesis and ligation reactions were carried out using T7 DNA polymerase and T4 DNA ligase, respectively. An aliquote of the synthesis reaction was used to transform E. coli XL1 blue (Stratagene) strain and transformants were selected on carbenicillin containing plates. Growth of the uracil containing plasmid DNA in this strain markedly reduces the propagation of the uracil containing DNA (wild type) strand. Mutants were selected by plasmid DNA minipreps and diagnostic restriction enzyme digestion. Sequences were further verified by DNA sequence analysis. The mutations made were: F21V/AS, E32K/AS, K33I/AL, E37T/AS, T38/A, L40/A, K42E/AS, E43/A, L44V/AL, W51A/AS, R64/Q, S68/A, Y70/A, N72/Q, Q75I/AS, N81/Q. Mutation "F21V/AS" indicates, for example, that the phenylalanine at position 21 of ICAM-R (SEQ ID NO: 1) and the valine at position 22 were respectively changed to an alanine and a serine, while mutation "T38/A" indicates that the threonine at position 38 of ICAM-R (SEQ ID NO: 1) was changed to an alanine. Effects of each mutation on anti-ICAM-R monoclonal antibody binding were tested according to the procedure described in Section C above. Table 6 below summarizes the results obtained, wherein a mutation with a "critical" effect was defined as 0–20% binding of an antibody in comparison to binding to wild type ICAM-R, an "important" effect was defined as about 50% binding in comparison binding to wild type ICAM-R, and a minor effect was defined as about 75% binding in comparison to binding to wild type ICAM-R. Mutations that did not effect binding of an antibody are not listed in Table 6.

TABLE 6

| Effect of Mutating Amino Acid Position(s) on Binding | Monoclonal Antibody | | | | | | | | |
|---|---|---|---|---|---|---|---|---|---|
| | ICR1.1 | ICR2.1 | ICR3.1 | ICR4.2 | ICR5.1 | ICR6.2 | ICR7.1 | ICR8.1 | ICR9.2 |
| Critical | F21V | F21V | F21V | F21V | F21V | F21V | F21V | F21V | F21V |
| Critical | E32K | E32K | E32K | — | — | — | — | E32K | — |
| Critical | — | K33I | — | — | — | — | — | — | — |
| Critical | E37T | — | — | — | E37T | — | E37T | — | — |
| Critical | — | — | — | — | — | — | W51A | — | — |
| Critical | — | — | — | — | — | — | Y70 | — | — |
| Critical | — | — | — | — | — | — | Q75I | — | — |
| Important | — | — | — | — | — | — | E32K | — | — |
| Important | K33I | — | — | — | — | — | — | — | — |
| Important | — | — | E37T | — | — | — | — | — | — |
| Important | — | — | — | — | — | — | K42E | — | — |
| Important | — | — | — | — | — | — | L44V | — | — |
| Important | W51A | W51A | — | — | W51A | W51A | — | W51A | — |
| Important | Y70 | Y70 | Y70 | — | — | — | — | — | — |

TABLE 6-continued

| Effect of Mutating Amino Acid Position(s) on Binding | Monoclonal Antibody | | | | | | | | |
|---|---|---|---|---|---|---|---|---|---|
| | ICR1.1 | ICR2.1 | ICR3.1 | ICR4.2 | ICR5.1 | ICR6.2 | ICR7.1 | ICR8.1 | ICR9.2 |
| Important | — | — | — | — | Q75I | — | — | — | — |
| Minor | K42E | L44V | K33I | — | K42E | — | L40A | — | — |
| Minor | — | — | — | — | E32K | — | — | — | — |
| Minor | — | — | W51A | — | — | — | — | — | — |

The mutations T38/A, S68/A and R64/Q had no effect on binding to any of the nine antibodies tested, while mutation E43/A resulted in 50% increase in binding of the above nine monoclonal antibodies in comparison to binding to wild type ICAM-R. Mutation F21V/AS abolished binding of all antibodies and appears to grossly affect the conformation of ICAM-R.

EXAMPLE 16

The distribution of ICAM-R protein and the expression of ICAM-R RNA in various cells and cell lines were respectively assayed by FACS analysis and Northern blot hybridization.

A. FACS Analyses of ICAM-R Protein Distribution In Leukocytic Cell Lines and Normal Leukocytes FACS analyses carried out as described in Example 13C on leukocyte cell lines using anti-ICAM-R monoclonal antibody ICR-2.1, anti-ICAM-1 antibody (LB2) and anti-CD18 antibody (TS/18, ATCC HB203) illustrated that ICAM-R is expressed on a wide variety of in vitro propagated cells lines representative of the major leukocyte lineages: T lymphocytes, B lymphocytes, and myeloid cells. Surface expression of ICAM-R was not detected on the primitive erythroleukemic line, K562. Further, ICAM-R was not expressed detectably by cultured human umbilical vein endothelial cells (HUVECS) either before or after stimulation with tumor necrosis factor which did upregulate expression of ICAM-1. This pattern of expression is also distinct from that observed for ICAM-2 which is expressed on endothelium. Table 7 below provides the mean fluorescence of each cell sample and the percent positive cells relative to a control in each cell sample (e.g., mean fluorescence of 13/11% positive cells).

TABLE 7

| Cell Type | Cell Line | ICAM1 | ICAMR | CD18 |
|---|---|---|---|---|
| T cell | CEM | 13/11 | 212/99 | 160/99 |
| T cell | MOLT4 | ND | ND | 15/77 |
| T cell | HUT78 | 41/97 | ND | 110/99 |
| T cell | SKW3 | 9/36 | 293/99 | 82/99 |
| B cell | JY | ND | ND | 60/99 |
| B cell | JUOYE | 300/99 | 153/99 | 28/9 |
| B cell | RAJI | 229/99 | 98/96 | 51/98 |
| Mono | HL-60 | 53/89 | 146/100 | 159/100 |
| Mono | HL60-PMA | 88/99 | ND | 251/100 |
| Mono | U937 | 83/99 | 148/100 | 61/100 |
| Mono | U937-PMA | 68/100 | ND | 170/100 |
| Myelo | KG-1 | 32/84 | 587/99 | 239/99 |
| Myelo | KG-1a | 32/90 | 238/97 | 83/93 |
| Erythro | K562 | 37/0.84 | 31/0.27 | ND |
| Endo | Huvec | 51/18 | 57/1 | ND |
| Endo | Huvec-TNF | 278/99 | 36/1 | ND |
| Human | Lymphocytes | 31/19 | 388/99 | 305/99 |

TABLE 7-continued

| Cell Type | Cell Line | ICAM1 | ICAMR | CD18 |
|---|---|---|---|---|
| Human | Monocytes | 74/96 | 862/99 | 1603/99 |
| Human | Granulocytes | 12/40 | 323/99 | 376/99 |
| Monkey | Lymphocytes | 79/2 | 55/81 | 722/99 |
| Monkey | Monocytes | 98/1.7 | 162/95 | 1698/99 |
| Monkey | Granulocytes | 20/2 | 80/96 | 623/99 |

B. FACS Analyses of ICAM-R Distribution On Human and Macaque Leukocytes

FACS analyses performed as described in Example 13C on normal human and macaque peripheral blood leukocytes showed that the anti-ICAM-R monoclonal antibody ICR-2.1 reacted with the three major human leukocyte lineages: lymphoid, monocytoid and granulocytoid. See the final six entries of Table 7. In addition, monoclonal antibodies ICR-4.2 and ICR-9.2 cross-reacted with macaque leukocytes (Table 2 and Example 13E) indicating that these monoclonal antibodies may be useful in monitoring the expression of ICAM-R in disease models executed in this animal.

Human bronchiolar aveolar lavage cells (primarily macrophages) were stained with five anti-ICAM-R antibodies (ICR-2.1, ICR-3.1, ICR-4.2, ICR-6.2 and ICR-7.1) as described in Example 13 and analyzed by FACS. None of the antibodies specifically stained these cells. Other data obtained via immunohistological tests suggests that ICAM-R can be expressed on macrophages on interstitial spaces in the lung. (See Example 18, where the expression of ICAM-R in lung tissue is described.)

C. Northern Blot Analyses of ICAM-R RNA Expression in Leukocytic Cell Lines and HUVECS RNA was extracted from human leukocyte cell lines and from HUVECS as described in Example 7, and was analyzed by Northern blot hybridization (also as described in Example 7) by probing with either ICAM-R or ICAM-1 cDNA. After phosphorimaging of the initial hybridization, blots were stripped and reanalyzed using a human actin probe. The results of the actin normalized Northerns of ICAM-R and ICAM-1 probed blots are presented in FIG. 7(A through B) as bar graphs. At the RNA level, ICAM-R was expressed in a variety of leukocytic cell types. ICAM-R RNA expression was not necessarily concomitant with the expression of ICAM-1 RNA. For example, unstimulated HUVECS express low levels of ICAM-1 and expression is upregulated following TNF stimulation (FIG. 7B). In contrast, detectable levels of ICAM-R message were not observed in unstimulated or stimulated HUVECS (FIG. 7A).

EXAMPLE 17

Immunoprecipitations of detergent solubilized lysates of surface biotinylated human cell lines KG1a, K562 and CEM were performed using the four anti-ICAM-R monoclonal antibodies: ICR-2.1, ICR-1.1, ICR-4.2, and ICR-3.1.

Cell surface proteins on human leukocyte cell lines KG1, K562, and CEM were labelled by reaction with sulfo-NHS-biotin (Pierce Chemical Company, Rockford, Ill.) as follows. For each reaction 0.5–1×10$^7$ cells were washed twice in phosphate buffered saline (PBS), resuspended in 1 ml PBS and 10 µl of 100 mM sulfo-NHS-biotin diluted in PBS was added. Following incubation for 10 minutes at 37° C. the cells were washed once with PBS, and 4 ml of 10 mM Tris pH 8.4, 0.25M sucrose was added and the cells were then incubated for 30 minutes at 4° C. with gentle mixing. The cells were pelleted by centrifugation, the supernatant was aspirated and the pellet was solubilized with 300 µl of 10 mM Tris pH 8, 50 mM NaCl, 1% Triton X-100, 1 mM phenylmethylsulfonyl fluoride, 1 mM EDTA by incubating on ice for 15 minutes. The lysate was clarified by centrifugation and the supernatant was precleared by addition of 25 µl normal mouse serum and incubation for 1 hour at 4° C. This step was followed by the addition of 20 µl of a 50/50 (v/v) solution of protein-A sepharose beads (Sigma) that had been preincubated with 20 µg of affinity purified rabbit anti-mouse Immunoglobulin (Zymed). After incubation for 30 minutes at 4° C., the sepharose beads were removed by centrifugation.

Specific immunoprecipitations were then performed by addition of 20 µl of sepharose beads that had been prearmed by sequential incubation with rabbit anti-mouse immunoglobulin and either anti-ICAM-R or control IgG$_1$ or IgG$_{2a}$ monoclonal antibodies. Following overnight incubation at 4° C. with agitation, sepharose beads were pelleted in a microcentrifuge and washed sequentially 2 times with 1 ml 10 mM Hepes pH 7.3, 150 mM NaCl, 1% Triton X-100; 1× with 0.1M Tris pH 8, 0.5M LiCl, 1% beta mercaptoethanol; and 1× with 20 mM Tris pH 7.5, 50 mM NaCl, 0.5% NP40. Beads were then eluted with 50 µl 150 mM Tris pH 6.8, bromphenol blue, 20% beta mercaptoethanol, 4% SDS and 20% glycerol; boiled for 5 minutes; and pelleted by centrifugation. Thirty-five µl of the resulting eluate was then analyzed by SDS-PAGE (10% acrylamide). After electrophoresis, proteins were electroblotted onto Immobilon-P membranes (Millipore, Bedford, Mass.) and incubated in 2% bovine serum albumin diluted in Tris-buffered saline containing 0.2% Tween-20 for 20 minutes at 4° C. Blots were then incubated with horseradish peroxidase coupled to streptavidin (Vector) in TBS-Tween at room temperature for 20 minutes. Following 3 rinses in TBS-Tween, ECL western blotting detection reagents (Amersham) were added and chemiluminescent bands were visualized on Kodak X-OMAT-AR film.

Figure 8A:
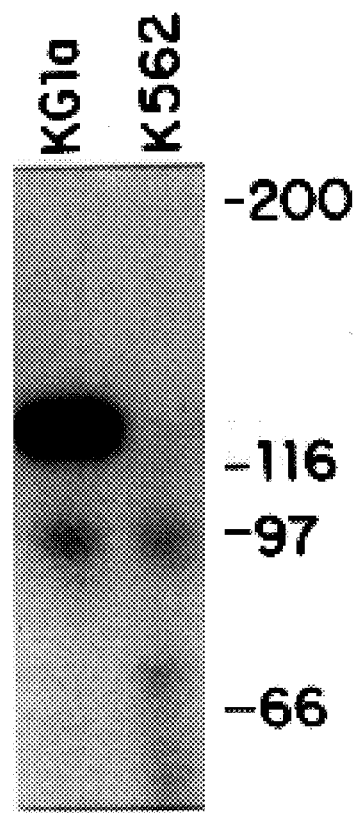
FIG. 8(A through B) comprises photographs of Western blots of immunoprecipitations of lysates from human cells lines using ICAM-R specific monoclonal antibodies.

FIG. 8(A through B) shows the resulting Western blots. A single specifically precipitated species of 120 kD was observed in immunoprecipitates with monoclonal antibody ICR-2.1 from KG1 cells, but not from K562 cells (See FIG. 8A).

Figure 8B:
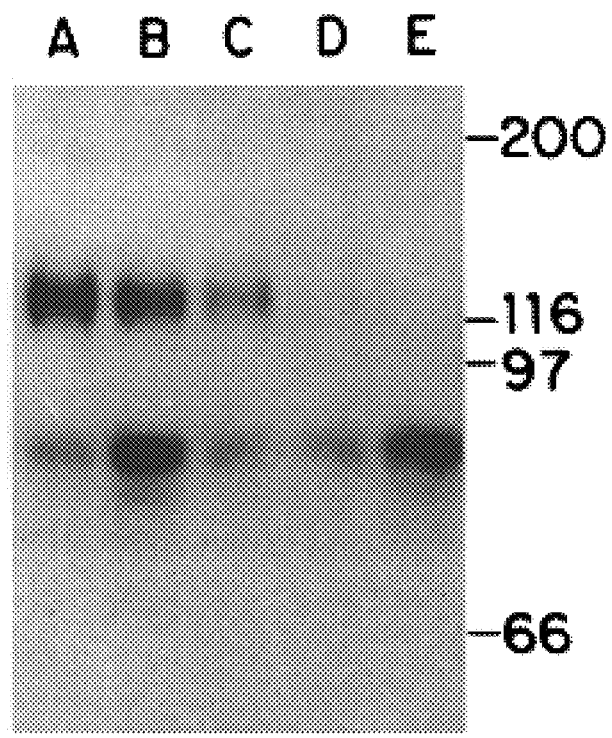
Figure 9A:
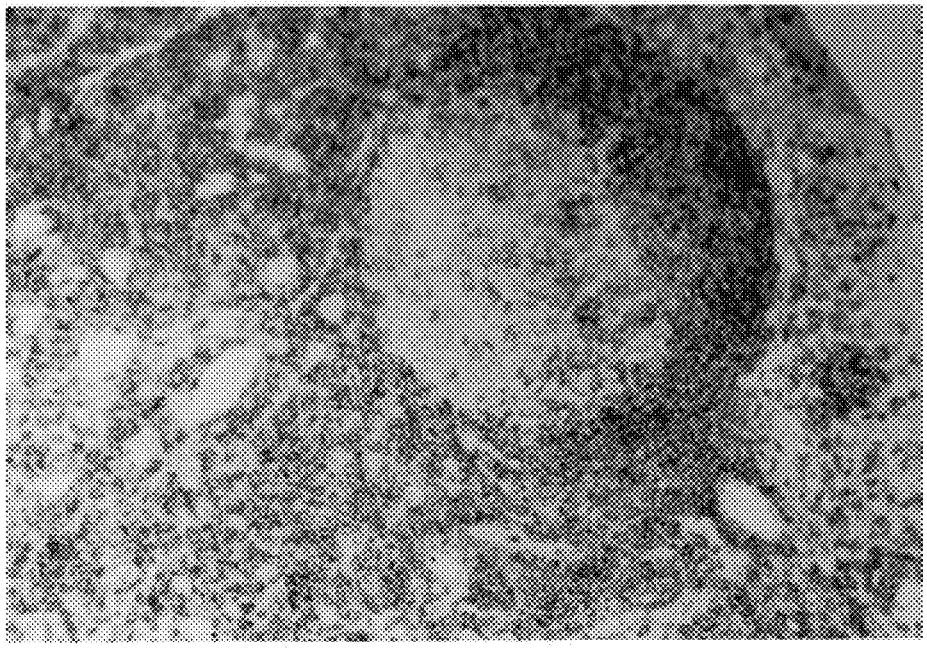
FIG. 9(A through G) presents photomicrographs of immunohistologic staining of various human tissues with an anti-ICAM-R monoclonal antibody.
Figure 9B:
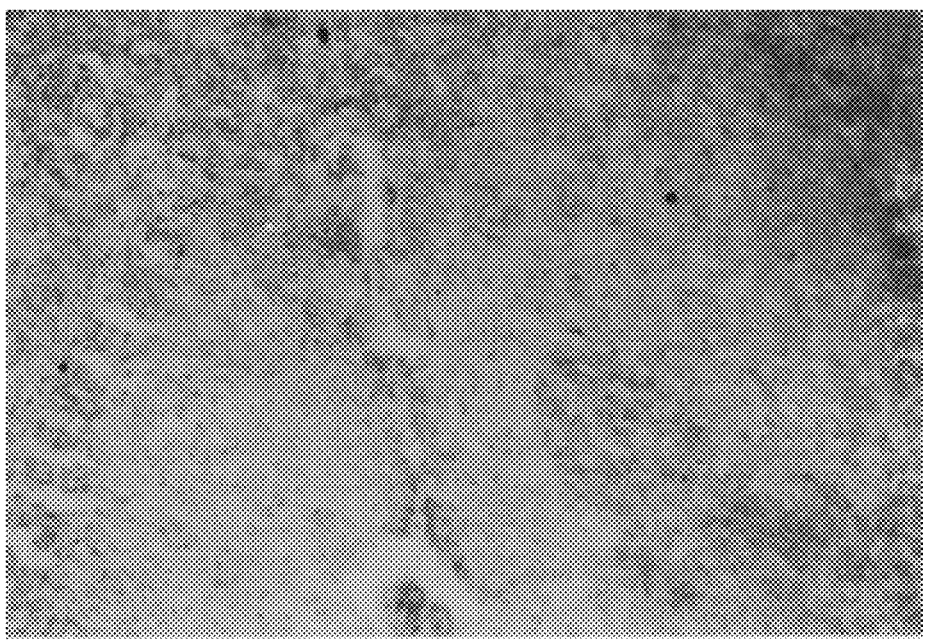
Figure 9C:
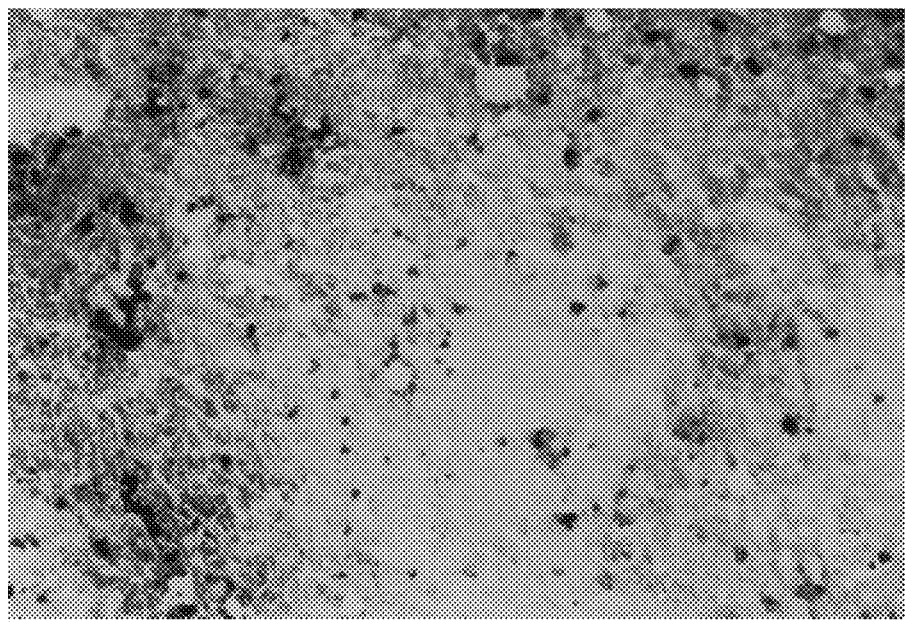
Figure 9D:
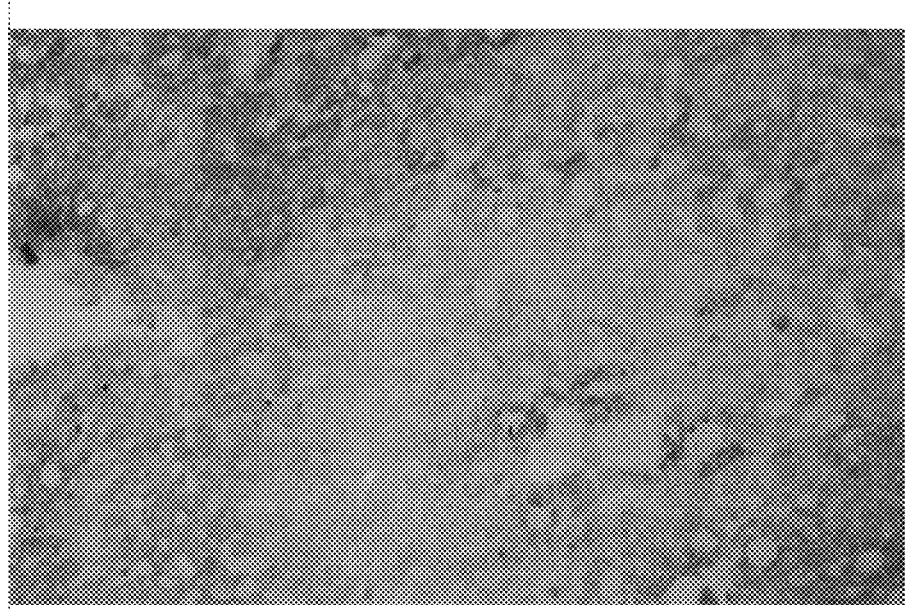
Figure 9E:
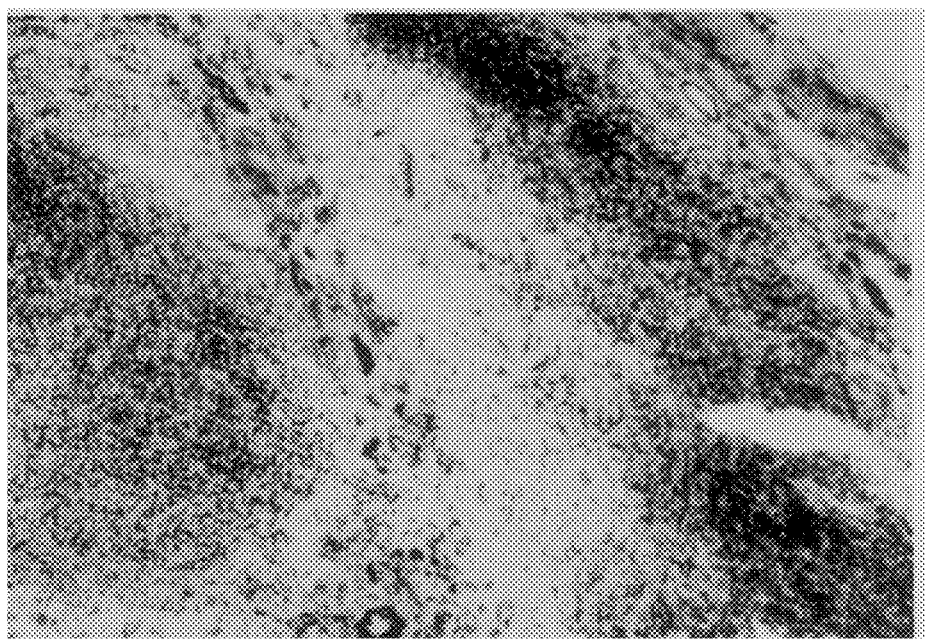
Figure 9F:
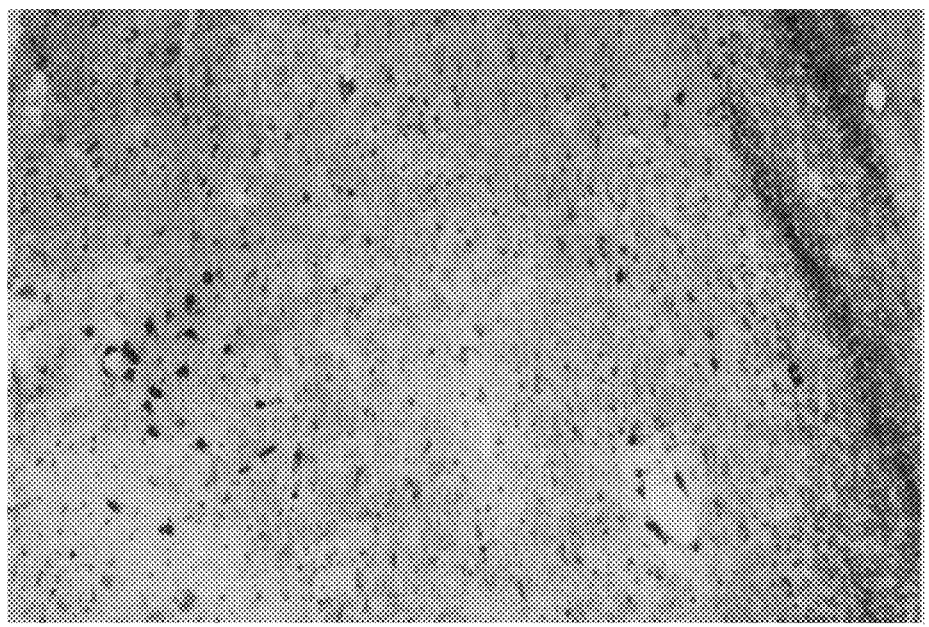
Figure 9G:
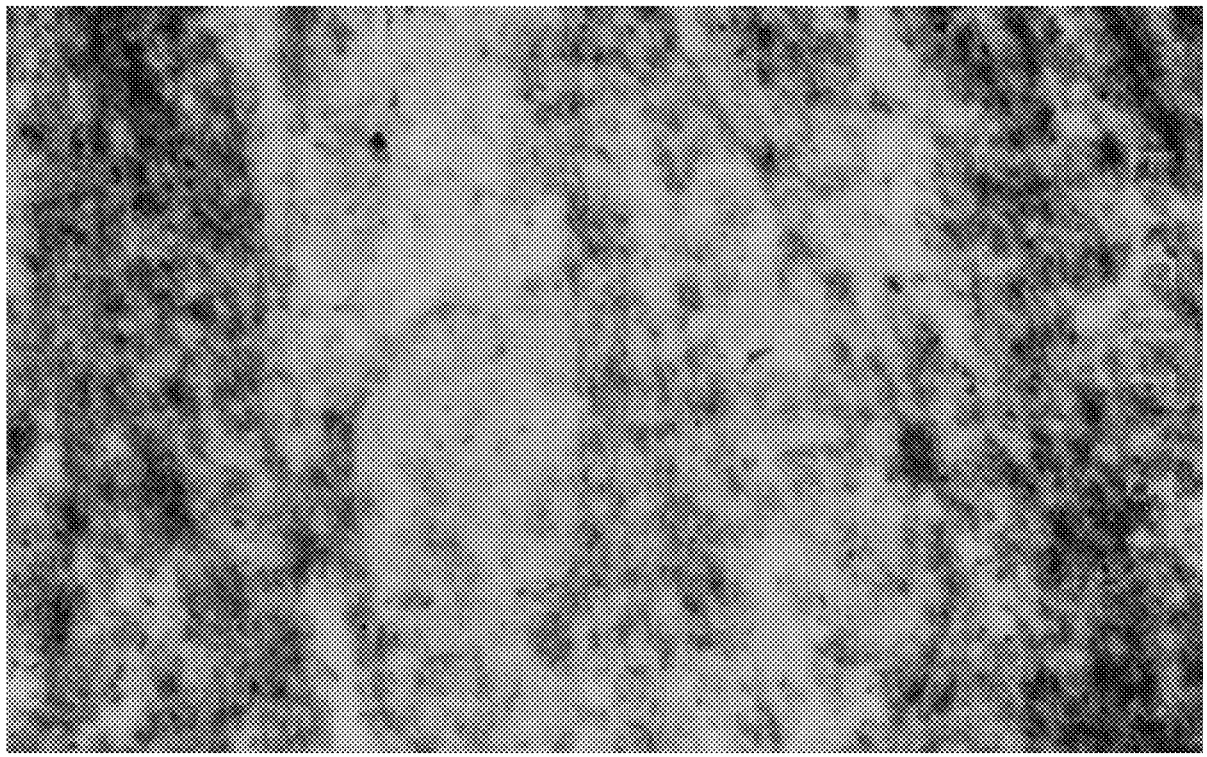

A 120 kD band was also resolved in immunoprecipitates of the T cell line CEM (FIG. 8B, wherein Lane A was reacted with monoclonal antibody ICR-2.1; Lane B, monoclonal antibody ICR-4.2; Lane C, monoclonal antibody ICR-3.1; Lane D, monoclonal antibody ICR-1.1; and Lane E, a negative control antibody). The size of the ICAM-R species resolved in other immunoprecipitations varied slightly depending on the cellular source. Species ranging from ~116 kD on some lymphoid cells to ~140 kD on some myeloid cells were observed. Given the predicted size (about 52 kD) of the core peptide based on the nucleotide sequence of the ICAM-R gene, these results imply that ICAM-R is heavily modified post-translationally to yield the mature cell surface form of the protein.

EXAMPLE 18

Immunohistologic staining with anti-ICAM-R monoclonal antibodies ICR-4.2, ICR-1.1, and ICR-2.1 and control antibodies was carried out on various human tissues including tonsil, spleen, liver, lung, kidney, heart, digestive tract, skin, synovium, and brain (both normal and multiple sclerosis-afflicted brain tissue). Similar staining patterns were obtained using the different anti-ICAM-R antibodies as well as when using purified anti-ICAM-R monoclonal antibody ICR-1.1 or hybridoma supernatant.

Sections (6 µm) of various tissues were layered onto Vectabond (Vector) coated slides and stored at −70° C. (some sections were stored at −20° C.). Prior to use, slides were removed from −70° C. and placed at 55° C. for 5 minutes. Sections were then fixed in cold acetone for 10 minutes and air dried. Sections were blocked in a solution containing 1% BSA, 60% normal human sera, and 6% normal horse sera for 30 minutes at room temperature. Primary antibody directed against ICAM-R, a negative control antibody, anti-ICAM-1 monoclonal antibody or anti-ICAM-2 monoclonal antibody was applied to each section for 1 hour at room temperature. Unbound antibody was washed off by immersing the slides 3 times in 1×PBST for 5 minutes each time. Biotinylated anti-mouse immunoglobulin (Vector) was then applied to each section in the same fashion. ABC-HPO (Avidin-Biotin Complex-HPO) was used to detect the second antibody. A solution of reagent A (9 µl) (Vector) combined with reagent B (9 µl) (Vector) in 1 ml of 1% BSA/PBST was applied to each section for 30 minutes at room temperature. Slides were then washed 3 times in 1×PBST. DAB substrate (3'3 diaminobenzidine-tetrahydrochloride, Sigma) (stock: 600 mg/ml DAB diluted 1:10 in 0.05M Tris Buffer, pH 7.6, with 3% H$_2$O$_2$ added to a final concentration of 1%) was applied to each slide for 8 minutes at room temperature. Slides were washed in water for 5–10 minutes at room temperature and then 1% osmic acid was added (to enhance color development) for one minute at room temperature. Slides were then washed in tap water for 5–10 minutes and counterstained in 1% Nuclear Fast Red (NFR) for 30 seconds at room temperature. Lastly, slides were alcohol dehydrated, treated with Histroclear and mounted with coverslips using histomount.

A selection of results of staining with the monoclonal antibodies is presented in FIG. 9(A through G) as photomicrographs wherein the tissue in 9A, 9B and 9E is human tonsil; in 9C and 9D is human liver; in 9F is brain from a human patient afflicted with multiple sclerosis; and in 9G is normal human brain. Sections shown in 9A, 9C, 9F and 9G were stained with anti-ICAM-R monoclonal antibody ICR-4.2. Sections shown in 9B and 9D were stained with the negative control antibody, while the section shown in 9E was stained with the anti-ICAM-1 antibody. Staining revealed high level expression of ICAM-R in lymphoid tissues such as tonsil (9A). Expression was also detected on tissue leukocytes in other nonlymphoid organs such as the liver wherein Kupfer cells (liver macrophages) were positively stained (9C). Evidence that ICAM-1 and ICAM-R expression are regulated distinctly in vivo is given by the staining pattern observed in tonsil and lymph node: ICAM-1 is strongly expressed on B cells in the germinal centers of secondary follicles and not expressed in primary follicles, whereas ICAM-R is expressed strongly in the primary follicles and weakly in the germinal centers (10A and 10E). Significantly, ICAM-R expression was also detected on leukocytes infiltrating sites of inflammation. For example, ICAM-R expression was observed on perivascular infiltrating leukocytes in the brain tissue of individuals afflicted with multiple sclerosis (9F). Similar staining was not observed in anatomically equivalent locations of brain tissue from normal individuals (9G). ICAM-R expression was also detected on leukocytes infiltrating synovia of arthritic joints. Also, whereas expression of ICAM-1 and ICAM-2 was detected on endothelia lining vessels, ICAM-R was not typically observed on vascular endothelium. Expression of ICAM-R was detected on cells in the aveoli of the lung.

More generally, cells expressing ICAM-R were detected in all normal and pathological tissues. These ICAM-R expressing cells could be identified morphologically and by comparison of serial immunological staining as leucocytes and antigen-presenting cells. All CD3$^+$ T cells present in various tissues expressed high levels of ICAM-R. In contrast, only a subset of B cells (IgD+) present in primary follicles and in the mantle zone of germinal centers expressed high levels of ICAM-R. Amongst antigen-presenting cells, Langerhans cells in the epithelium expressed high levels of ICAM-R while only a subset of other tissue macrophages expressed ICAM-R.

ICAM-R monoclonal antibodies ICR-1.1 and ICR-4.2 were also used in procedures similar to those described above to stain biopsy tissue sections of both human mammary carcinoma (ductal and lobular) and melanomas. In both tumor types some sections exhibited specific patchy staining of the endothelia in a range of blood vessels (venular, arterioles and capillaries). Corresponding normal tissue showed no expression of ICAM-R on endothelium.

Thus, while ICAM-R is typically not expressed on endothelium of the general vasculature, it is apparently expressed on a subset of vessels associated with two types of solid tumors. Given this distribution, reagents (e.g., monoclonal antibodies) directed against ICAM-R may provide therapeutic vehicles which selectively target tumor versus normal vasculature.

In summary, the contrasts in the patterns of expression of ICAM-R versus ICAM-1 and ICAM-2 are significant. Constitutive expression of ICAM-2 was observed on both leukocytes and endothelium. Basal expression of ICAM-1 on leukocytes, endothelia and epithelia was low or absent but was induced in pathologic tissues or in vitro. ICAM-R was expressed at high levels on most leukocytes and, notwithstanding rare expression on tumor associated endothelia, was generally not expressed on vascular endothelia.

EXAMPLE 19

In order to determine whether ICAM-R is involved in homotypic cell adhesion, aggregation assays were performed with a panel of cell lines which express ICAM-R including T lymphoblastoid cell lines (SupT1, CEM, Molt 4, Hut 78, Jurkat, SKW3), B lymphoblastoid cells lines (Jijoye, Raji), monocytic cell lines (U937, HL60), a myelogenous cell line (KG-1) and the erythroleukemia cell line K562. To determine the function of the ICAM-R molecule, the cells were incubated with various antibodies before aggregation was assayed. Anti-ICAM-R supernatants produced by hybridomas ICR-2.1, ICR-1.1, ICR-4.2, and ICR-3.1 were used as well as antibody preparations known to block aggregation through a β2 integrin pathway: TS1/18 (ATCC HB203) specific for the CD18 molecule, the β-subunit of LFA-1; TS 1/22 (ATCC HB202) specific for the CD11a molecule, the α-chain of LFA-1; and LM2/1 (ATCC HB204) specific for the CD11b molecule, the α-subunit of MAC-1. Purified anti-ICAM-1 antibody and hybridoma supernatant directed against the α-chain of the VLA-4 molecule (hybridoma clone 163H, Michael Longenecker, Alberta, Canada) were used as controls.

Aggregation assays were done in duplicate, with and without addition of PMA (50 ng/ml). 3×10$^5$ cells in RPMI 1640 medium with 10% fetal calf serum were added in a flat-bottomed 96well microtest plate. When one antibody was tested in an experiment, 50 μl of purified antibody or hybridoma supernatant were added to the wells (PMA was added at the same time to selected wells). When two antibodies were tested in the same experiment, the antibodies were added sequentially to the cells at room temperature and incubated for 30 minutes each (incubation for 15 minutes at 37° C. produced the same results), and then the cells were incubated at 37° C. Incubating the antibodies with the cells before addition of PMA or at the same time as the PMA did not cause any significant change in the aggregation results. After incubation with the antibody or antibodies, cells were uniformly resuspended and then incubated at 37° C. for 4 to 24 hours. Aggregation scoring was done with an inverted microscope. In each experiment, the efficacy of the PMA stimulation was checked in parallel by stimulating Raji cells with an equal amount of PMA and determining the amount of aggregation blockable by monoclonal antibodies to CD18, CD11a, and ICAM-1 molecules.

Table 8, below, sets out the results of one representative aggregation experiment wherein PMA was added. Aggregation scores are reported on a range from 0 to 5, wherein 0 indicates that no cells were in clusters; 1 indicates that less than 10% of the cells were in clusters; 2 indicates that 10 to 50% cells were aggregated; 3 indicates that 50 to 100% cells were in loose clusters; and 4 indicates that almost 100% of the cells were in compact aggregates.

TABLE 8

| Antibody Treatment | | | | | | | | | |
|---|---|---|---|---|---|---|---|---|---|
| Antibody 1 | — | — | — | — | — | — | αCD18 | αCD11a | αCD11b |
| Antibody 2 | — | αCD18 | αCD11a | αCD11b | 26H11C | 26I10E | 26H11C | 26H11C | 26H11C |
| Aggregation | | | | | | | | | |
| SUPT1 cells (after 4 hours) | 2 | 1 | 1 | 2 | 4 | 2 | 2 | 2 | 4 |
| SUPT1 cells (after 24 hours) | 2 | 1 | 1 | 2 | 4 | 2 | 2 | 2 | 4 |

Interestingly, treatment with three of the antibodies specific for ICAM-R (ICR-2.1, ICR-1.1, and ICR-3.1) stimulated homotypic cell-cell aggregation (data for ICR-1.1 and ICR-3.1 not shown). Stimulation occurred in both the presence and absence of co-stimulatory agents such as a phorbol ester (PMA). The fourth anti-ICAM-R monoclonal antibody (ICR-4.2) did not stimulate cell aggregation but blocked the aggregation stimulated by the other anti-ICAM-R antibodies. At least a portion of the aggregation stimulated by anti-ICAM-R antibodies in PMA treated cells was blocked by pretreatment with monoclonal antibodies against CD18 or CD11a indicating that one or more leukointegrins may participate in this type of adhesion.

To confirm that aggregation was induced by the anti-ICAM-R antibodies ICR-2.1, ICR-1.1, and ICR-3.1 the aggregation assays were performed using both the whole immunoglobulin (ICR-1.1-Ig) and Fab' fragments (ICR-1.1-Fab') purified from the same anti-ICAM-R monoclonal antibody (ICR-1.1). The assays were performed with SKW3 T cells as described above using ICR-1.1-Ig and ICR-1.1-Fab' at a concentration of 1 µg/ml. Supernatants of anti-CD18 and anti-ICAM-R (CIR-1.1-sup and ICR-4.2-sup) hybridomas were used as controls. After four hours, the same increase in cell aggregation was found for whole immunoglobulin as for the Fab' fragments or the ICR-1.1 supernatant (See Table 9 below).

TABLE 9

| Antibody Treatment | 0 | αCD18 | 26E3D-Ig | 26E3D-Fab' | 26E3d-sup | 26I10E-sup |
|---|---|---|---|---|---|---|
| Aggregation | 2 | 2 | 3 | 3 | 3 | 2 |

No increase in aggregation was found with anti-CD 18 supernatant or anti-ICAM-R ICR-4.2 supernatant. These results rule out the trivial explanation that enhanced aggregation was due to antibody mediated cross-linking of the cells. The engagement of ICAM-R protein, in this case by selected antibodies, may transduce a signal which alters the adhesive potential of the bound cells.

EXAMPLE 20

The process of activation and proliferation of cells of the immune system is marked by a continuum of cellular events. The upregulation of certain cell surface molecules (e.g., CD69 and the transferrin receptor) is an early marker of cell activation. Similarly, cell agglutination occurs early in the process of activation. The upregulation of the IL-2 receptor occurs at an intermediate to late stage and cell proliferation is a late event. Three types of experiments were performed to determine the extent to which ICAM-R is involved in immune cell activation/proliferation. In the first type, the capacity of ICAM-R presented on the surface of a transfected cell to stimulate proliferation of lymphocytes was examined. In the second type, antibodies of the invention recognizing distinct epitopes on ICAM-R were used as probes to engage the external domain of ICAM-R to determine the effects of antibody binding either alone or in combination with other stimuli on lymphocyte activation and proliferation. In the third type of experiment, the effects of soluble ICAM-R protein on T cell proliferation were determined.

A. Stimulation of PBMC Proliferation by ICAM-R Transfectants

Mouse L cells transfected with either ICAM-R cDNA or ICAM-1 cDNA (Example 7) were assayed for their ability to stimulate human peripheral blood mononuclear cell (PBMC) proliferation as measured by $^3$H-thymidine incorporation assays which indicate changes in the rate of DNA replication. Nontransfected mouse L cells or transfected L cells were obtained by trypsinization from tissue culture flasks and washed in RPMI-1640 containing 10% fetal bovine serum. Five×$10^4$ L cells in 120 µl tissue culture media (RPMI-1640 with 10% fetal bovine serum) were added to individual wells of a sterile 96-well flat bottom tissue culture plate and the plates were incubated for 24–36 hours at 37° C. in a 5% $CO_2$ incubator. The media was then removed in a sterile manner and 2×$10^5$ freshly isolated PBMC in a total volume of 200 µl tissue culture media were added to individual wells containing either transfected or non-transfected mouse L cells. PBMC were also added to control wells containing no L cells. The PBMC were previously isolated from healthy donors by centrifugation on Histopaque gradients (Sigma). Fresh peripheral blood was mixed with an equal volume of PBS, layered onto Histopaque and centrifuged at 450 g for 20 minutes with no brake applied. PBMC-containing fractions were collected, washed in PBS and adjusted to 1×$10^6$ viable cells/ml prior to addition into wells. The tissue culture plates were then incubated for a total of 4 days either in the presence or absence of PMA at a final concentration of 5 ng/ml. Lymphocyte proliferation was then assessed after the addition of 1 uCi $^3$H-thymidine (NEN, Boston, Mass.) to individual wells for the last 18–24 hours of culture. All cultures were then terminated by harvesting the contents of each well onto glass fiber filter strips using a PHD model plate harvester (Costar, Cambridge, Mass.). Individual filter mats were then placed in 3 ml Ecolume scintillation cocktail (ICN Biomedicals, Costa Mesa, Calif.) and counted using a beta-scintillation counter. LTK cells expressing ICAM-R stimulated proliferation of PBMC (as indicated by increased DNA replication) in comparison to nontransfected control LTK cells or in the absence of any stimulus. LTK cells expressing ICAM-1 induced the proliferation of PBMC to approximately an equal extent. By binding to its receptor(s) on PBMC, ICAM-R transmits an intercellular signal to the PBMC which in this cellular context results in cell proliferation.

B. PMBC Activation by ICAM-R Specific Monoclonal Antibodies

Anti-ICAM-R antibodies of the invention were also tested to determine their effect on immune cell activation and proliferation.

Anti-ICAM-R monoclonal antibodies were preliminarily tested for the ability to affect early events in cell activation including upregulation of the cell surface molecules CD69, the transferrin receptor and the IL-2 receptor on the target cells as measured by flow cytometry analysis. Unstimulated lymphocytes express low levels of the transferrin and IL-2 receptors. Expression of the receptors increases dramatically when lymphocytes are activated.

Anti-ICAM-R monoclonal antibodies ICR-1. 1 and ICR-4.2 were each tested for the ability to induce PMBC activation in the absence of other inducing stimuli. Monoclonal antibodies ICR-1.1 or ICR-42. (or control monoclonal antibodies) were added (10 µg/well in PBS) to individual wells of a 96-well flat bottom tissue culture plate and incubated for 3 hours at 37° C. in a 5% $CO_2$ incubator. The plates were washed 3 times with sterile PBS to remove unbound antibody and freshly isolated PBMC were immediately added to a final concentration of 2×$10^5$ cells/well in a volume of 200 µl media. The plates were then incubated for either 1 or 3 days at which time the cells cultured in the presence of different antibodies were removed, washed as described above in PBS containing 0.01% sodium azide and 1% BSA (FACS buffer) and stained with either FITC (Becton Dickinson)-conjugated negative control antibodies or a panel of FITC-conjugated anti-CD69, anti-transferrin receptor and anti-IL-2 receptor antibodies. Results were obtained by FACScan analysis. Expression of CD69 and the transferrin receptor but not the IL-2 receptor increased after 1 day when PBMC were cultured on immobilized (i.e., cross-linked) antibody ICR-1.1 but not when cultured on immobilized antibody ICR-4.2 PBMC incubated for 3 days on immobilized ICR-1.1 or ICR-4.2 had increased levels of cell surface expression of both the transferrin receptor and IL-2 receptor but not CD69. However, while increased expression of these lymphocyte activation markers was observed after 1 and 3 days this increased expression was unaccompanied by increased cell size. These results suggest that the anti-ICAM-R monoclonals ICR-1.1 and ICR-4.2 are able to directly induce early events in PMBC activation in the absence of additional exogenous stimuli but this activation does not result in blast transformation and associated increases in cell size.

C. Effect of ICAM-R Specific Monoclonal Antibodies on Stimulation of PMBC Activation by Anti-CD3 Antibody Anti-ICAM-R monoclonal antibodies were also tested for their ability to alter early events in PMBC activation stimulated by immobilized anti-CD3 monoclonal antibody G19 [Ledbetter et al., *J. Immunol.*, 135(4): 2331–2336 (1985)]. Monoclonal antibody G19 binds to the CD3 complex on T cells (the T cell receptor) and activates T cells. When PBMC were cultured in wells precoated with anti-CD3 antibody (0.05 $\mu$g/well) alone, only CD69 expression was elevated after one day. After three days, cell surface expression of CD69, the transferrin receptor and the IL-2 receptor was dramatically elevated. Upregulation of these activation markers was correlated with increases in cell size.

Ten $\mu$g of anti-ICAM-R monoclonal antibodies ICR-1.1 or ICR-4.2 (or control monoclonal antibodies to HLA Class I; Serotec, Oxford, England) were added per well of 96-well flat bottom tissue culture plates either in the presence or absence of anti-CD3 antibody initially added at 0.025 $\mu$g/well and washed to remove unbound antibody. Freshly obtained PBMC were immediately added ($2\times10^5$ cells/well). The cells were then incubated for a total of either 16 hours or 3 days at which time the cells were removed and washed 2 times in ice cold FACS buffer. Two$\times10^5$ cells were then resuspended in 50 $\mu$l ice cold FACS buffer, and 5 $\mu$l of FITC-conjugated anti-CD69, anti-transferrin receptor, anti-IL-2 receptor antibody or anti-FITC conjugated control Ig was added. The cells were incubated at 4° C. for 30 minutes and then washed 2 times in 0.5 ml ice cold FACS buffer. After the final wash the cells were resuspended in 0.5 ml FACS buffer and fluorescence determined by FACScan analysis. When PBMC were cultured for 3 days on 0.025 $\mu$g/well immobilized anti-CD3 either alone or in the presence of immobilized antibody to HLA Class I, expression of the transferrin and IL-2 receptors is not upregulated at this low does of immobilized anti-CD3. In contrast, culturing of PBMC in the presence of 0.025 $\mu$g/well immunobilized anti-CD3 and either immobilized anti-ICAM-R antibodies ICR-1.1 or ICR-4.2 antibodies resulted in significant upregulation of both the transferrin and IL-2 receptors. The effect was more pronounced with antibody ICR-1.1. Similar results were also obtained after 16 hours in culture. Low dose anti-CD3 in the presence of immobilized ICR-1.1 or ICR-4.2 antibody induced expression of CD69, but not the transferrin receptor, while low dose anti-CD3 (0.025 $\mu$g/well) in the presence of immobilized anti-HLA-I did not induce increased expression of either CD69 or the transferrin receptor. These results indicate that these anti-ICAM-R antibodies may serve as costimulatory molecules in early immune cell activation events.

D. Stimulation of PMBC Proliferation in the Presence of IL-2

Preliminary experiments were performed to determine if anti-ICAM-R monoclonal antibodies could affect the late event of cell proliferation again as measured by $^3$H-thymidine incorporation assays.

Monoclonal antibodies to ICAM-R were tested for their ability to directly stimulate PMBC proliferation in either the presence or absence of human recombinant IL-2 which potentiates but does not induce cell proliferation. Ten $\mu$g of ICAM-R monoclonal antibodies ICR-1.1 or ICR-4.2 (or control IgG$_1$ and IgG$_2$) antibodies) in PBS were added per well of 96-well flat bottom tissue culture plates and the plates were incubated for 34 hours at 37° C. in a 5% CO$_2$ incubator. After incubation, each well was rinsed 3 times with PBS and freshly obtained PBL were added to a final concentration of $2\times10^5$ cells/well in a volume of 200 $\mu$l. Ten units/ml human recombinant IL-2 (Genzyme, Boston, Mass.) was then added to selected wells. The plates were incubated for a total of 3 days at 37° C. in a 5% CO$_2$ incubator. $^3$H-thymidine incorporation by the PMBC was determined as described earlier in this example. The anti-ICAM-R antibodies ICR-1.1 and ICR-4.2 did not induce PMBC proliferation even in the presence of rIL2. Positive controls for lymphocyte proliferation included immobilized anti-CD3 and anti-LFA-1 (60.3) monclonal antibodies. These results indicate that while the immobilized anti-ICAM-R antibodies stimulate expression of activation markers such as CD69, etc., by themselves they do not directly stimulate the entry of large numbers of PBMC into S phase of the cell cycle.

E. Costimulation of Lymphocyte Proliferation by ICAM-R Specific Antibodies

Figure 10:
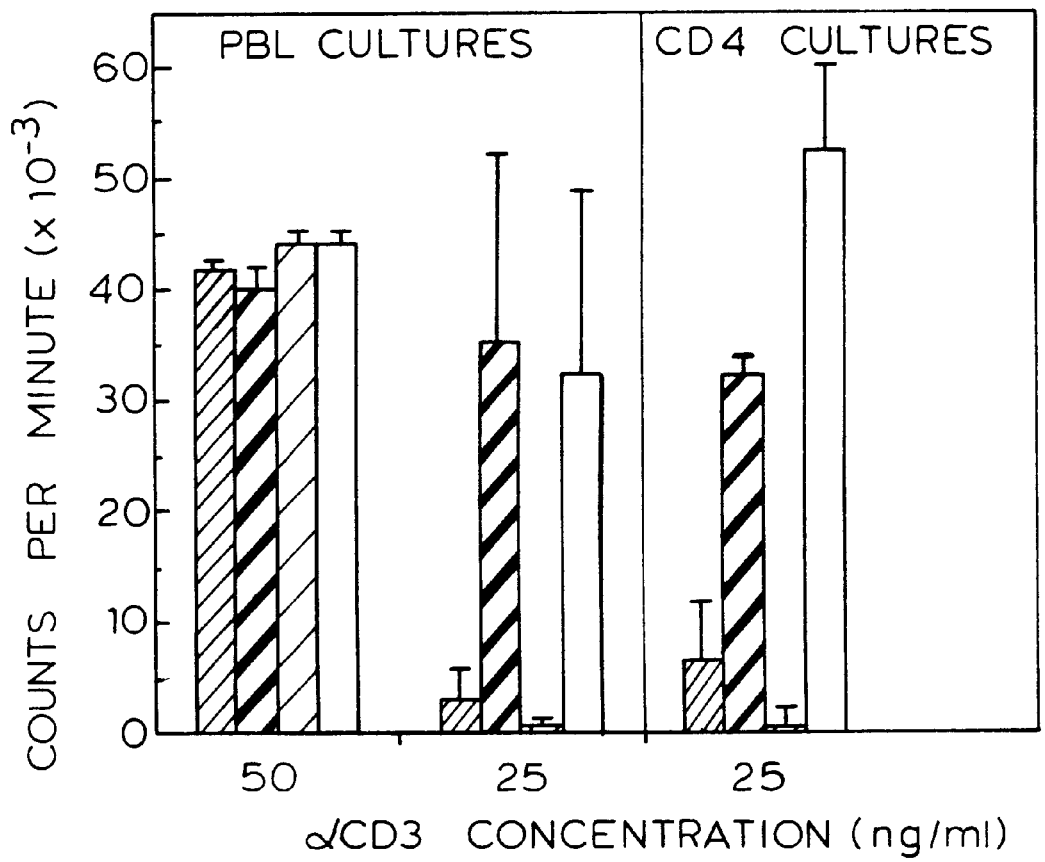
FIG. 10 is a bar graph depicting the effects of anti-ICAM-R monoclonal antibodies on the stimulation of lymphocyte proliferation by anti-CD3 antibodies.

Because anti-ICAM-R antibodies with anti-CD3 antibodies costimulated early PBMC activation events, anti-ICAM-R antibodies were tested for the ability to costimulate lymphocyte proliferation induced by immobilized anti-CD3 antibody. In addition, to determine whether anti-ICAM-R antibodies costimulate T-lymphocytes in the absence of accessory cells, anti-ICAM-R antibodies were tested for their ability to costimulate proliferation of pure CD4$^+$ T-lymphocytes, isolated using negative selection. To isolate CD4$^+$ cells PBMC were suspended in tissue culture medium, added to 75 ml tissue culture flasks (Corning) and incubated for 1 hour at 37° C., 5% CO$_2$. Plastic nonadherent cells were then removed from the flask by gently rinsing once with PBS. The nonadherent cell fraction was suspended ($10^7$ cells/ml) in an antibody cocktail containing 1 $\mu$g/ml anti-CD8 antibody (Pharmingen, San Diego, Calif.), 1 $\mu$g/ml anti-CD 19 (Becton Dickinson), 1 $\mu$g/ml anti-CD11b (Becton Dickinson) in 10% FBS-PBS (coating medium), and incubated for 1 hour at 4° C. Unbound antibody was removed by washing twice in coating medium. Cells were then resuspended ($10^7$ cells/ml) in coating medium containing Goat-anti-mouse Ig coated magnetic beads (45 $\mu$l/$10^6$ cells)(Advanced Magnetics, Cambridge, Mass.) and incubated for 1 hour at 4° C. Cells bound to magnetic beads were then removed from suspension using a strong magnet. CD4$^+$ populations obtained using this method were found to be >90% pure by flow cytometric analysis. PBMC or CD4$^+$ cells were adjusted to a concentration of $1\times10^6$ viable cells/ml in tissue culture medium. Individual wells of a 96-well flat bottom tissue culture plate were precoated with 0.001 μg anti-CD3 monoclonal antibody G19 per well. The plates were incubated for 3 hours at 37° C. in a 5% $CO_2$ incubator and unbound antibody was removed by rinsing the wells 3 times in PBS. After the final PBS wash, monoclonal antibodies to ICAM-R (ICR-4.2 or ICR-1.1) or control antibodies were immediately added to a final concentration of 10 μg/well. The plates were then reincubated for an additional 3 hours at 37° C. The wells were again washed three times with PBS to remove unbound antibody and freshly isolated PBMC were immediately added to the wells ($2\times10^5$ cells in a volume of 200 μl/well). The plates were then incubated for 3 days. Lymphocyte proliferation was measured by $^3$H-thymidine incorporation by the PMBC or $CD4^+$ cells. As shown in FIG. 10 immobilized anti-ICAM-R monoclonal antibodies ICR-1.1 and ICR-4.2 increased the PBMC and purified $CD4^+$ cell response to anti-CD3. Effects of the immobilized anti-ICAM-R antibodies on PBMC aggregation (an earlier event than PBMC proliferation) induced by anti-CD3 monoclonal antibody were also examined in this experiment. Anti-CD3 stimulated aggregation was inhibited almost 100% by antibody ICR-1.1 but was unaffected by immobilized ICR-4.2 and minimally inhibited by antibodies ICR-2.1 and ICR-4.1.

The results of the assays for the ability of anti-ICAM-R antibodies to affect the proliferation of cells on which ICAM-R is expressed indicate that binding of the antibodies of the invention to ICAM-R transmits a direct intracellular signal to T lymphocytes which modulates cell proliferation.

F. Co-Stimulation of PBL by Soluble ICAM-R

Soluble ICAM-R was assayed for the ability to costimulate human lymphocyte activation. Human peripheral blood lymphocytes (PBL) were obtained by Ficoll-Hypaque centrifugation and $2\times10^5$ cells per well were incubated in the presence of either media, plate bound soluble ICAM-R, plate bound anti-CD3 (OKT3) or a combination of plate bound anti-CD3 and soluble ICAM-R. At 17 hours and 4 days after initiation of culture cells were removed, stained with monoclonal antibodies to human lymphocyte activation antigens and analyzed by flow cytometry.

Human lymphocytes cultured for 4 days in the presence of plate bound anti-CD3 (0.5 ug/well) and soluble ICAM-R (100 ng/well) express elevated levels of the activation antigens ICAM-1, IL-2 receptor and transferrin receptor compared to lymphocytes cultured in the presence of anti-CD3 alone. In contrast, lymphocytes cultured in the presence of soluble ICAM-R (100 ng/well) alone expressed no increased levels of these activation antigens compared to cells cultured in media alone.

Experiments were also performed to determine if ICAM-R is involved in early events of qualitatively distinct types of cell-cell contact dependent T-lymphocyte activation (e.g., responses to staph enterotoxin A and alloantigen).

G. Effect of ICAM-R Specific Antibodies on Superantigen-induced Proliferation of PBL Superantigen-induced proliferation and aggregation of human peripheral blood lymphocytes (PBL) were assessed in the presence of the ICAM-R specific antibodies of the invention. The effect of soluble and plate-bound anti-ICAM-R antibodies and anti-HLA class I control B-H9 (Serotec) antibodies on proliferation and cell aggregation was measured three days after stimulation of human PBL with Staphylococcus Enterotoxin A (SEA) (Toxin Technology, Sarasota, Fla.). Plate-bound antibodies were prepared on the day of culture as follows. Purified antibody (10 μg in 0.1 ml PBS) was added to individual wells of 96-well flat bottom plates. Plates were then incubated for 4 hours at 37° C. Following incubation, unbound antibody was removed by aspirating each well and rinsing 4 times with fresh PBS. Human PBL were isolated from healthy donors on Histopaque (Sigma) gradients. Fresh peripheral blood was mixed with an equal volume of phosphate buffered saline (PBS), layered onto Histopaque and centrifuged at 450×g for 20 minutes with no brake applied. Lymphocyte fractions were collected and washed twice by adding a fresh volume of RPMI supplemented with 10% fetal bovine serum and centrifuging at 200×g for 8 minutes. PBL were suspended in a final volume of 10 ml of RPMI-FBS. Viable PBL were counted using the method of vital dye exclusion. Twenty μl of a dilution of cell suspension in 0.4% trypan blue stain (Gibco) was added to a hemacytometer chamber and dye-excluding cells were then counted using an inverted microscope. Two-hundred thousand viable PBL were then added to 96-well flat-bottom tissue culture plates containing 100, 10 or 1 μg soluble or plate-bound ICR-1.1, ICR-2.1, ICR-3.1, ICR-4.2, ICR-5.1, ICR-6.2, ICR-7.1, ICR-8.1, ICR-9.2, ICR-12.1, ICR-13.1, ICR-14.1, ICR-15.1, ICR-16.1, ICR-17.1, B-H9 or IOT2 (AMAC, Inc., Westbrooke, Me.) antibodies. Finally, each culture was stimulated with SEA (1000 or 10 pg/ml in triplicate) and cultured at 37° C. in 5% $CO_2$. After 3 days, proliferation was measured as $^3$H-thymidine incorporation.

Figure 11A:
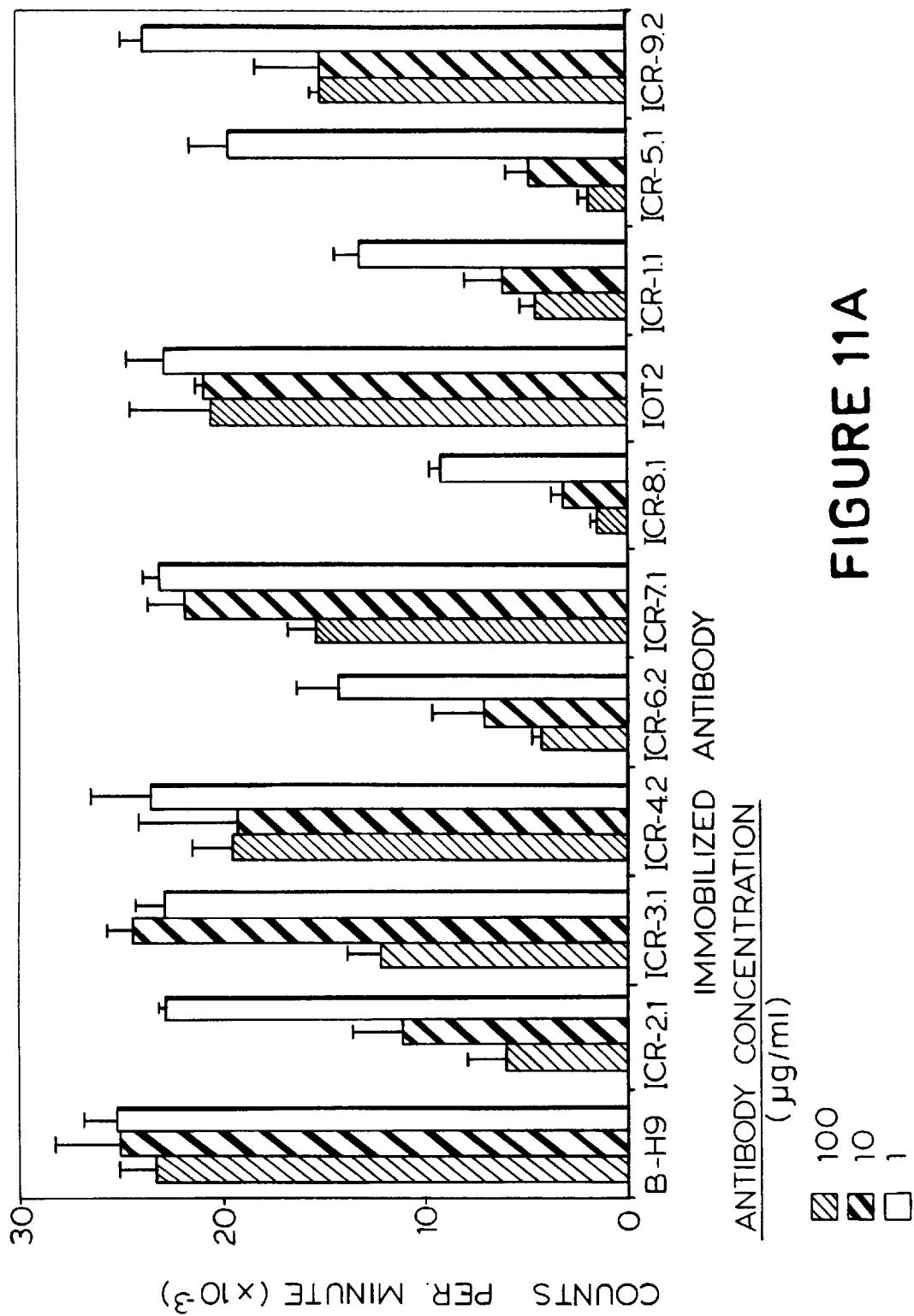
Figure 11B:
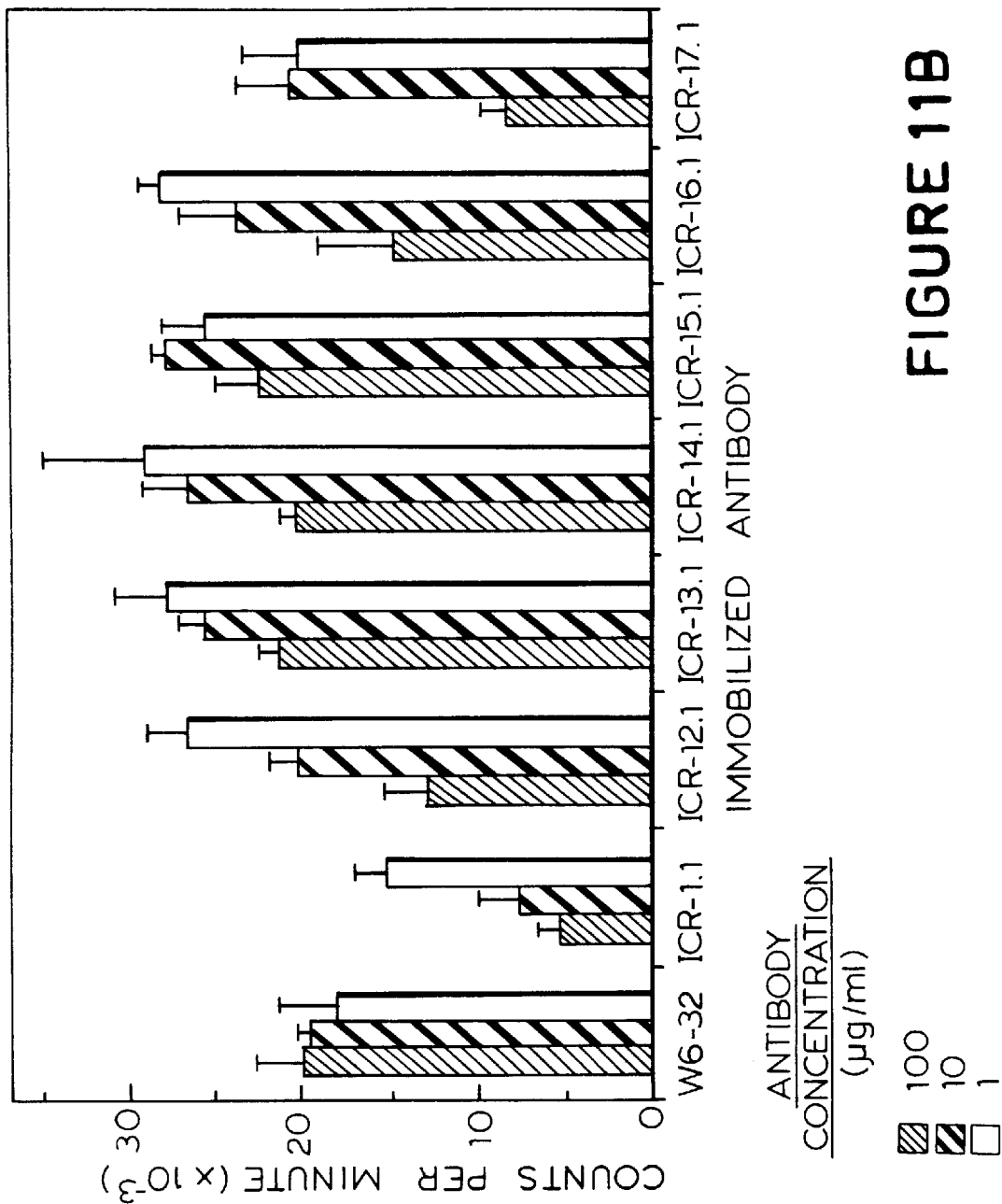
Figure 11C:
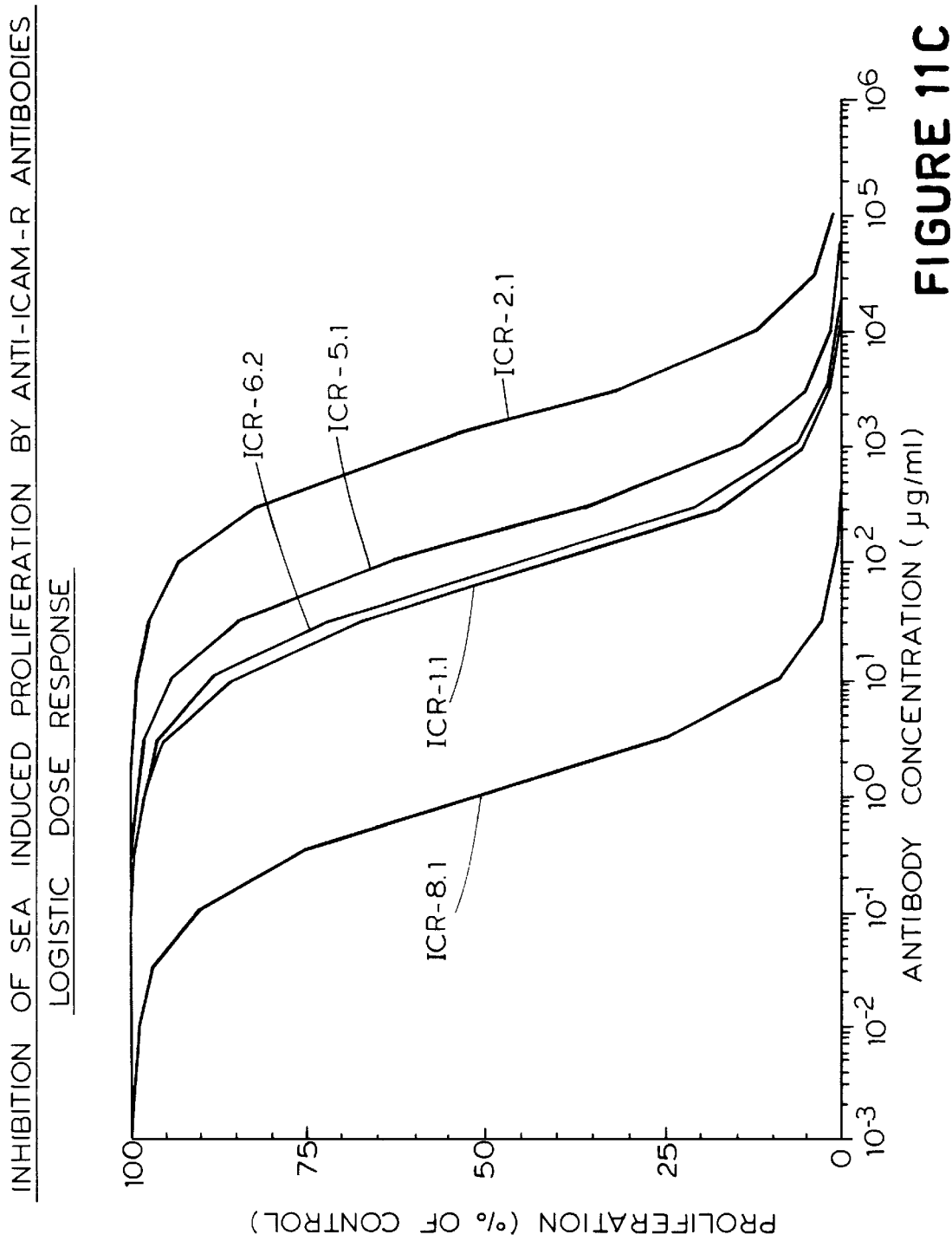
FIG. 11C is a graph comprising logistic dose response curves of the effects of anti-ICAM-R monoclonal antibodies on superantigen-induced proliferation of human peripheral blood lymphocytes.

Treatment with soluble anti-ICAM-R antibodies failed to alter proliferation in comparison to soluble control antibodies. Plate-bound (i.e., cross-linked) antibodies ICR-1.1, ICR-2.1, ICR-5.1, ICR-6.2 ICR-8.1 and ICR-17.1 however, significantly inhibited proliferation in response to SEA ($p<0.05$) while antibodies ICR-3.1, ICR-4.2, ICR-7.1, ICR-9.2, ICR-13.1, ICR-14.1 and ICR-15.1 did not (FIG. 11A and FIG. 11B). Antibodies ICR-12.1 and ICR-16.1 inhibited proliferation slightly, while antibodies ICR-12.1, ICR-13.1, ICR-14.1, ICR-15.1 and ICR-16.1 exhibited enhancing effects at the lowest concentration. Antibodies ICR-1.1 and ICR-8.1 were the most effective at inhibiting proliferation. FIG. 11C presents logistic dose response curves for monoclonal antibodies ICR-1.1, ICR-2.1, ICR-5.1, ICR-6.2 and ICR-8.1 in terms of the percentage of proliferation observed compared to proliferation in the presence of control antibodies and Table 10 below sets out the $IC_{50}$ values obtained from the curves.

TABLE 10

| Monoclonal Antibody | $IC_{50}$ (μg/ml) |
|---|---|
| ICR-1.1 | 63 |
| ICR-2.1 | 1434 |
| ICR-5.1 | 170 |
| ICR-6.2 | 80 |
| ICR-8.1 | 1 |

Concomitant to inducing entry into the cell cycle, SEA induces cell aggregation. Effects of the monoclonal antibodies ICR-1.1 and ICR-4.2 on cell aggregation were measured using an inverted microscope. Plate-bound ICR-1.1 also significantly inhibited cell aggregation at both SEA concentrations in comparison to plate-bound B-H9 and ICR-4.2 antibodies. Inhibition of aggregation by plate-bound ICR-1.1 was almost complete. In contrast, plate-bound ICR-4.2 antibody only slightly inhibited aggregation in comparison to plate-bound B-H9. Aggregation of PBL induced by SEA was not affected by soluble anti-ICAM-R antibodies ICR-1.1 or ICR-4.2 in comparison to soluble B-H9 antibody.

The minimum time required for plate-bound anti-ICAM-R to inhibit SEA-induced proliferation was also determined. PBL were pre-incubated on plate-bound ICR- 4.2, ICR-1.1 or isotype-matched anti-HLA-I control antibodies B-H9 (IgG$_1$) and I0T2 (IgG$_2$) with or without SEA (10 pg/ml) for 3, 5 and 7 hours. PBL were then transferred to clean wells and cultured in the presence of SEA (10 pg/ml) for 3 days. The results of $^3$H-thymidine incorporation (proliferation) assays are summarized in FIG. 12. Immobilized ICR-1.1 antibody and, to a lesser extent ICR-4.2 antibody, significantly reduced proliferation in comparison to isotype-matched controls after only 3 hours of incubation. This result indicates that binding of plate-bound ICR-1.1 or ICR-4.2 to ICAM-R transmits an intracellular signal capable of inhibiting proliferation even after cells have been removed from the immobilized antibodies. These results suggest that therapeutically efficacious engagement of ICAM-R may be achieved without maintaining saturating levels of an ICAM-R specific agent (e.g., a monoclonal antibody) over long periods of time.

Figure 13:
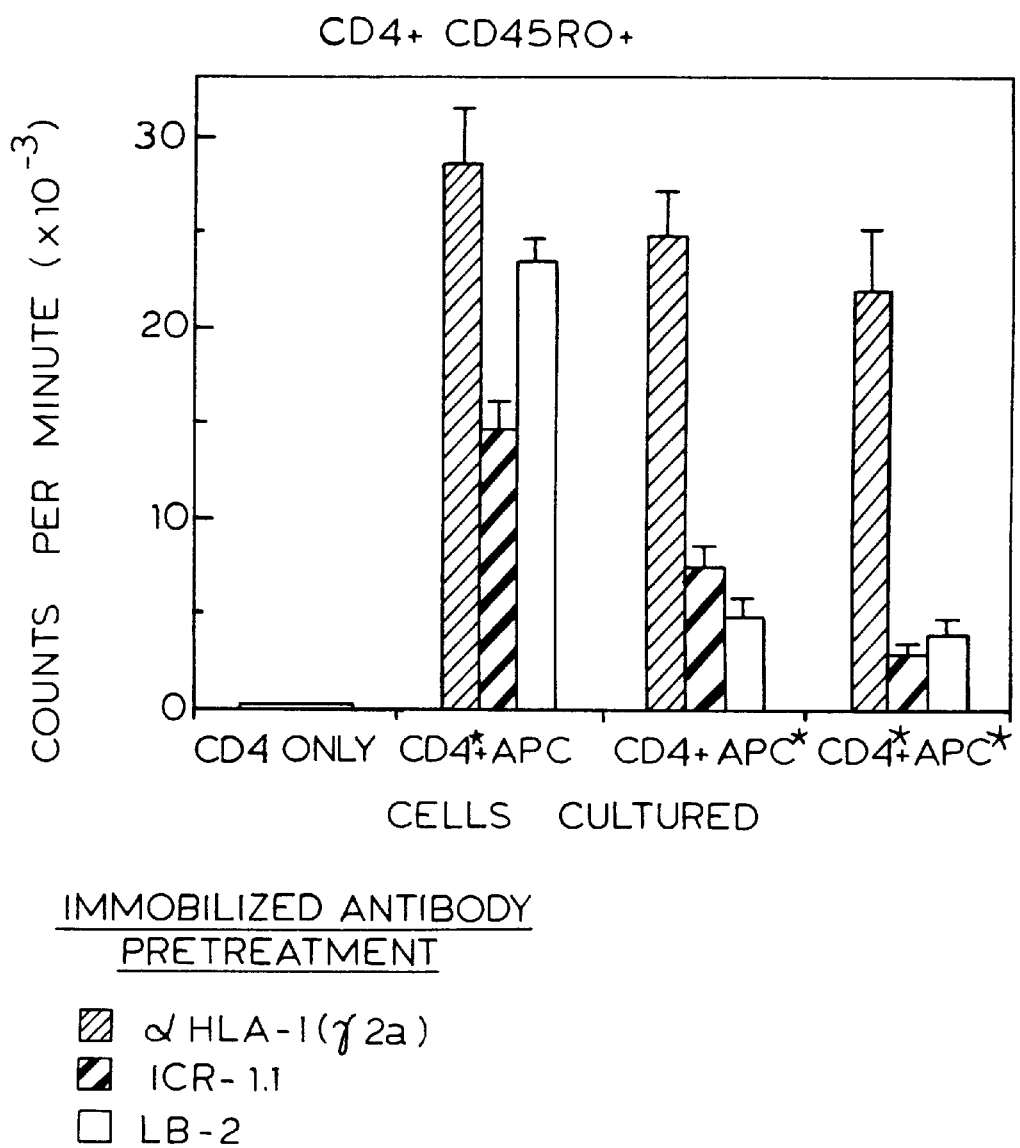
FIG. 13 is a bar graph illustrating the effect of anti-ICAM-R monoclonal antibodies on superantigen-induced proliferation of "memory" T cells.
Figure 14:
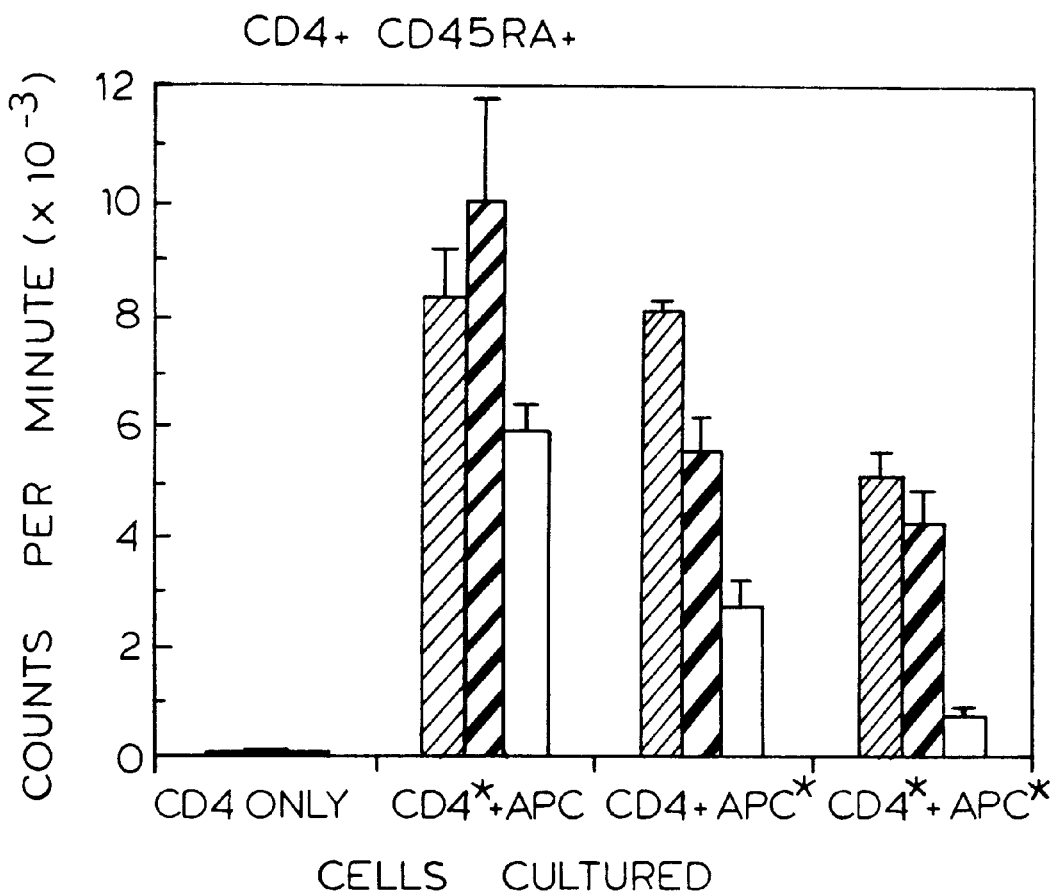
FIG. 14 comprises a bar graph depicting the effect of anti-ICAM-R monoclonal antibodies on superantigen-induced proliferation of "resting" T cells.

Because both T cells and accessory cells express high levels of ICAM-R, the inhibition of cell-cell contact dependent T cell activation during the response to SEA by ICR-1.1 could be mediated by ICR-1.1 binding to T cells, accessory cells or both. Additionally, because ICAM-R and ICAM-1 differ markedly in their expression on nonactivated T cells, it is possible that anti-ICAM-1 and anti-ICAM-R may inhibit the SEA response by targeting T cell subsets in different states of activation. Because the role of ICAM-R may differ in naive and memory cells, the ability of anti-ICAM-R antibodies to inhibit SEA induced proliferation of CD4$^+$ CD45RO$^+$ ("memory") cells, or CD4$^+$ CD45RA$^+$ ("resting") cells was tested. Plasmatic nonadherent PBMC (10$^7$ cells/ml) were incubated for 1 hour at 4° C. with a cocktail of antibodies (1 μg/ml each) containing anti-CD8, anti-CD19, anti-CD11b, anti-HLA-DR (Becton Dickinson) and either anti-CD45RO (Amac)(to obtain CD45RA$^+$ CD4$^+$ cells), or anti-CD45RA (Amac) (to obtain CD45RO$^+$ CD4$^+$ cells) in coating medium. The cell suspension was washed twice with coating medium to remove unbound antibody and incubated with goat anti-mouse IgG coated magnetic beads. Cells bound to magnetic beads were then removed from the suspension using a strong magnet. CD45RO$^+$ and CD45RA$^+$ populations obtained using this method were found to be >95% pure as determined by flow cytometric analysis. Two hundred thousand purified memory T cells, resting T cells or plastic adherent cells were incubated on immobilized ICR-1.1, anti-ICAM-1 antibody LB-2 or anti-HLA-I antibody p10.1 (10 μg/ml) (Gerald Nepom, Virginia Mason Research Center, Seattle, Wash.) for 3 hours. The antibody treated memory or resting T cells were removed to clean wells and admixed with 2×10$^4$ plastic adherent cells. Antibody treated accessory cells were admixed with either untreated memory T cells or untreated resting T-cells. Each reconstituted culture was then stimulated with SEA (10 pg/ml). The results of $^3$H-thymidine incorporation (proliferation) assays are summarized in FIG. 13 wherein the abbreviation "APC" stands for "antigen presenting cells," which are the accessory cells in this assay, and wherein the asterisks indicate the population of cells pretreated with antibody. Pretreatment of CD45RO$^+$ T cells or accessory cells (APC???) with ICR-1.1 blocked proliferative responses to SEA in comparison to p10.1 control antibody. When both cell populations were treated with ICR-1.1, the inhibitory effect was additive. Inhibition of proliferation by the anti-ICAM-1 antibody LB-2, occurred only when adherent cells were pretreated and was not further enhanced when the admixed cells were also pretreated. As shown in FIG. 14 pretreatment of CD45RA$^+$T cells with ICR-1.1 did not affect SEA responses. ICR1.1 or LB2 pretreatment of adherent cells resulted in modest inhibition of CD45RA$^+$ cell proliferation.

H. Inhibition of Lymphocyte Proliferation in Response to Allogenic Irradiated Stimulator Cells Monoclonal antibodies to ICAM-R were also tested for the ability to alter lymphocyte proliferation (as measured by $^3$H-thymidine incorporation) in response to alloantigenic irradiated stimulator cells. Responder cells were prepared by obtaining PBMC from a normal donor using Histopaque centrifugation as described above. To prepare stimulator cells, PBMC from a second, unrelated donor were concurrently isolated and irradiated at 1500R by exposure to a gamma emitting cesium source. Two hundred thousand responder cells and 2×10$^5$ irradiated stimulator cells (suspended in culture medium) were then added to wells containing soluble or immobilized ICR-1.1, ICR-2.1, ICR-3.1, ICR-4.2, ICR-5.1, ICR-6.2, ICR-7.1, ICR-8.1, ICR-9.2, immobilized B-H9, immobilized p10.1, or soluble 515F (anti-rat CD 18) antibody and incubated for 6 days at 37° C., 5% CO$_2$. Lymphocyte proliferation (3H-thymidine incorporation) was assessed in the last 18–24 hours of culture.

Immobilized monoclonal antibodies ICR-1.1, 2.1, 6.2 and 8.1 consistently reduced proliferation in comparison to control antibodies. ICR-8.1 also inhibited alloantigen-stimulated proliferation when administered in soluble form.

EXAMPLE 21

Table 11 below is a summary of various characteristics of ICAM-R specific monoclonal antibodies of the invention which have been specifically described in the foregoing examples. In Table 11, the abbreviation "NC" stands for "not conclusive" and the abbreviation "ND" stands for "not determined." The antibodies marked with an asterisk in Table 11 enhanced activation at low concentrations.

TABLE 11

| Antibody | Produced by Hybridoma | Isotype | Reactive Domain | Residues Critical/Important to Binding | Blockade of Adhesion of JY Cells to Soluble ICAM-R | Blockade of Lymphocyte Activation | |
|---|---|---|---|---|---|---|---|
| | | | | | | SEA | Alloantigen |
| ICR-I.1 | 26E3D | IgG$_{2a}$ | 1 | F21V, E32K, E37T, K33I, W51A, Y70 | YES | YES | YES |
| ICR-2.1 | 26H11C | IgG$_1$ | 1 | F21V, E32K, K33I, W51A, Y70 | NO | YES | YES |
| ICR-3.1 | 2618F | IgG$_1$ | 1 | F21V, E32K, E37T, Y70 | YES | NO | NC |
| ICR-4.2 | 26I10E | IgG$_1$ | 2 | F21V | NO | NO | NC |
| ICR-5.1 | 42C5H | IgG$_{2a}$ | 1 | F21V, E37T, W51A, Q75I | YES | YES | NC |
| ICR-6.2 | 42D9B | IgG$_1$ | 2 | F21V, W51A | NO | YES | YES |

TABLE 11-continued

| Antibody | Produced by Hybridoma | Isotype | Reactive Domain | Residues Critical/Important to Binding | Blockade of Adhesion of JY Cells to Soluble ICAM-R | Blockade of Lymphocyte Activation SEA | Blockade of Lymphocyte Activation Alloantigen |
|---|---|---|---|---|---|---|---|
| ICR-7.1 | 43H7C | IgG$_1$ | 1 | F21V, E37T, W51A, Y70, Q751, E32K, K42E, L44V | NO | NO | NO |
| ICR-8.1 | 46D7E | IgG$_1$ | 1 | F21V, E32K, W51A | YES | YES | YES |
| ICR-9.2 | 46I12H | IgG$_{2a}$ | 2 | F21V | NO | NO | NO |
| ICR-12.1 | 63E11D | IgG$_1$ | 1 | ND | YES | YES* | ND |
| ICR-13.1 | 63G4D | IgG$_1$ | 1 | ND | YES | NO* | ND |
| ICR-14.1 | 63H4C | IgG$_1$ | 1 | ND | YES | NO* | ND |
| ICR-15.1 | 63H6H | IgG$_1$ | 1 | ND | YES | NO* | ND |
| ICR-16.1 | 63I1C | IgG$_1$ | 1 | ND | YES | YES* | ND |
| ICR-17.1 | 6316G | IgG$_1$ | 1 | ND | YES | YES | ND |

EXAMPLE 22

One inference from the aforementioned examples that antibodies specific for ICAM-R modulate the response of lymphocytes to a variety of stimuli (e.g., SEA and allogeneic cells) is that engagement of ICAM-R by either its natural counter-receptors or by antibodies of the invention transduces a signal to the ICAM-R expressing cell. ICAM-R specific signalling events are likely to involve the interaction of the cytoplasmic domain of ICAM-R with cellular enzymatic components (e.g., kinases, phosphatases) of one or more second messenger pathways and/or with cytoskeletal components in a pattern unique to ICAM-R.

Preliminary experiments are consistent with this concept and with the idea that ICAM-R is distinct from ICAM-1 in its linkages with second messenger systems. Extracts from unstimulated Raji cells were prepared, fractionated and assayed for kinase activity as follows. Seven×10$^7$ cells were washed once in PBS and lysed in buffer containing 20 mM Tris pH 7.5, 0.5 mM EDTA, 1% Triton X-100 (Pierce), 10 ug/ml pepstatin and leupeptin (Boehringer), 2 mM PMSF for 1 hour on ice. Lysates were pelleted in a refrigerated microfuge at 14,000 rpm for 15 minutes and the resulting supernatant was applied to a DEAE sephacel column (Pharmacia) equilibrated in 20 mM Tris pH 7.5, 0.5 mM EDTA (Buffer A). The column was run at a rate of 0.25 ml/minute and developed with a gradient of 0 to 0.35M NaCl in buffer A over 60 minutes. In these initial experiments, only those fractions enriched in protein kinase C (PKC) activity (as determined using an Amersham assay kit and following manufacturers instructions) were examined. Fractions enriched in PKC activity were pooled and used as a source of kinase(s) to test for differential phosphorylation of synthetic peptides of the complete cytoplasmic domains of ICAM-1, ICAM-2 and ICAM-R (amino acids 481 to 518 of SEQ ID NO: 1). Assays were performed according to manufacture's instructions with peptides at 75 uM final concentration. Ten ul of the reaction mixture was boiled in 30 ul Laemmli sample buffer and resolved on a 12.5% SDS-PAGE gel. Following a 1.5 hour exposure of the gel on X-ray film phosphorylation of ICAM-R and ICAM-2 but not ICAM-1 was detected. Whether the phosphorylation was due to PKC or another co-fractionated kinase was not determined.

Further assays involved reacting fractions derived either from a column chromatography step or from solubilized cell fractions in the presence of Ca$^{++}$, Mg$^{++}$, cAMP, phosphatidylserine, cytoplasmic tail peptide and [$^{32}$P]ATP. Phosphorylation of specific peptides was assessed following resolution by gel electrophoresis. Jurkat cells were separated into subcellular fractions and each fraction was assayed for kinase activity on the cytoplasmic tail peptides. In these experiments, phosphorylation of ICAM-1 and ICAM-R was detected. However, kinases which phosphorylated ICAM-1 associated with cell membrane fractions, whereas kinases which phosphorylated ICAM-R were primarily cytosolic although also present in membranes. Additional support for different kinases acting on these two ICAM's comes from preliminary purification studies of these kinases. Jurkat cytosol fractionated on a MonoQ column (Pharmacia) equilibrated in 50 mM Tris pH 8, 5 mM EDTA and developed with a gradient to 0.6M NaCl over 30 minutes gives a very broad activity profile for kinases acting on ICAM-R. Only a subset of these fractions also have activity towards ICAM-1. This provides additional evidence that cellular kinases exist which differentially phosphorylate ICAM-R but not ICAM-1. Two dimensional phosphoamino acid analysis on these phosphorylated peptides shows only serine phosphorylation on ICAM-R and threonine phosphorylation on ICAM-1.

Preliminary experiments also indicate that the cytoplasmic domain of ICAM-R differentially associates with cytoskeletal components. Binding of the non-competing monoclonal antibodies ICR-1.1 and ICR-4.2 to ICAM-R was examined to assess the potential influence of each antibody on the association of lymphocyte ICAM-R with the cytoskeleton. The antibodies may mimic distinct natural ICAM-R ligands which employ ICAM-R as a cell surface receptor through which regulated cellular responses may be elicited.

Other investigators have previously observed that numerous human T lymphocyte surface antigens which occur as cell surface transmembrane glycoproteins can be induced to associate with the cytoskeleton if cell surface-bound antibody specific for these antigens is crosslinked with secondary antibodies [Geppert et al., *J. Immunol.*, 146: 3298 (1990)]. Many of these cell surface molecules are defined components of lymphocyte adhesion and/or activation pathways. The phenomenon of inducible association with the cytoskeleton is operationally defined as the resistance of cell-surface immune complexes to detergent extraction under defined conditions. Inducible detergent resistance does not require metabolic energy and can be observed in cells maintained at 0–4° C. throughout the experiment.

Experiments were conducted using freshly prepared human PBL or the human T lymphoblastoid cell line CEM-CCRF (ATCC CCL119). Briefly, freshly drawn human blood from healthy volunteer donors was diluted 1:1 with PBS and layered onto Sigma HistoPaque density separation medium. The gradients were centrifuged for 30 minutes at 1500 rpm (600×g) and the mononuclear cell fraction at the interphase was collected and washed three times with PBS. The cell pellet was resuspended in complete RPMI-1640 medium (Gibco, supplemented with L-glutamine, penicillin/ streptomycin, sodium pyruvate, 2-mercaptoethanol, and 10% FBS) and plated onto tissue culture-treated petri dishes for adherent cell depletion. Plates were incubated 1–2 hours at 37° C., 5% $CO_2$ after which nonadherent PBL were harvested and washed twice with ice-cold PBS. Conjugation of monoclonal antibodies to fluorescein using fluorescein isothiocyanate (FITC) was performed according to published procedures [see, e.g., Goding, *J. Immunol. Meth.*, 13: 215 (1976)] and, in brief, involves incubation of purified antibody with an excess of FITC (Sigma) in 0.1M bicarbonate buffer pH 8.1 for 90 minutes at 37° C. followed by exhaustive dialysis against PBS to remove unreacted FITC.

PBL or washed CEM cell suspensions ($1 \times 10^6$ cells) were dispensed into Falcon 12×75 mm tubes in ice-cold PBS-5% FBS, pelleted, and resuspended in 50 μl of FITC-conjugated anti-ICAM-R monoclonal antibody 26E3D-1 or 26I10E-2 adjusted to saturating concentration in the same buffer. Antibody binding was permitted to proceed for 30 minutes on ice, afterwhich unbound antibody was removed by pelleting cells which had first been resuspended in 1 ml of PBS-5% FBS through an underlaid cushion (0.7 ml) of neat (undiluted) FBS.

For groups stained with FITC-conjugated monoclonal antibody only, the 1 ml suspension was divided into two equal parts, each of which was separately underlaid with FBS, centrifuged, and the supernatant removed by aspiration. Cell pellets were then resuspended in 200 ul of control buffer (13 mM Tris pH 8.0, 150 mM NaCl, 2 mM $MgCl_2$, 2 mM EGTA, 2% FBS, 2.5 ug/ml aprotinin, 1 mM PMSF, 10 mM iodoacetamide) or detergent buffer [0.5% NP-40 (v/v) (US Biochemical, Cleveland, Ohio) in control buffer] and held for 20 minutes at room temperature, or overnight at 4° C., prior to FACS analysis. For groups in which cell surface-bound monoclonal antibody was crosslinked with secondary antibodies, following the first antibody staining step, washed cell pellets were resuspended in 50 ul of FITC-goat anti-mouse IgG (Sigma) diluted 1:100 in PBS-5% FCS and incubated for 30 minutes on ice. The cells were then resuspended, divided into two tubes as described above, pelleted, and buffer-treated in the presence or absence of detergent. FACS analysis was then performed on the cells.

Figure 15:
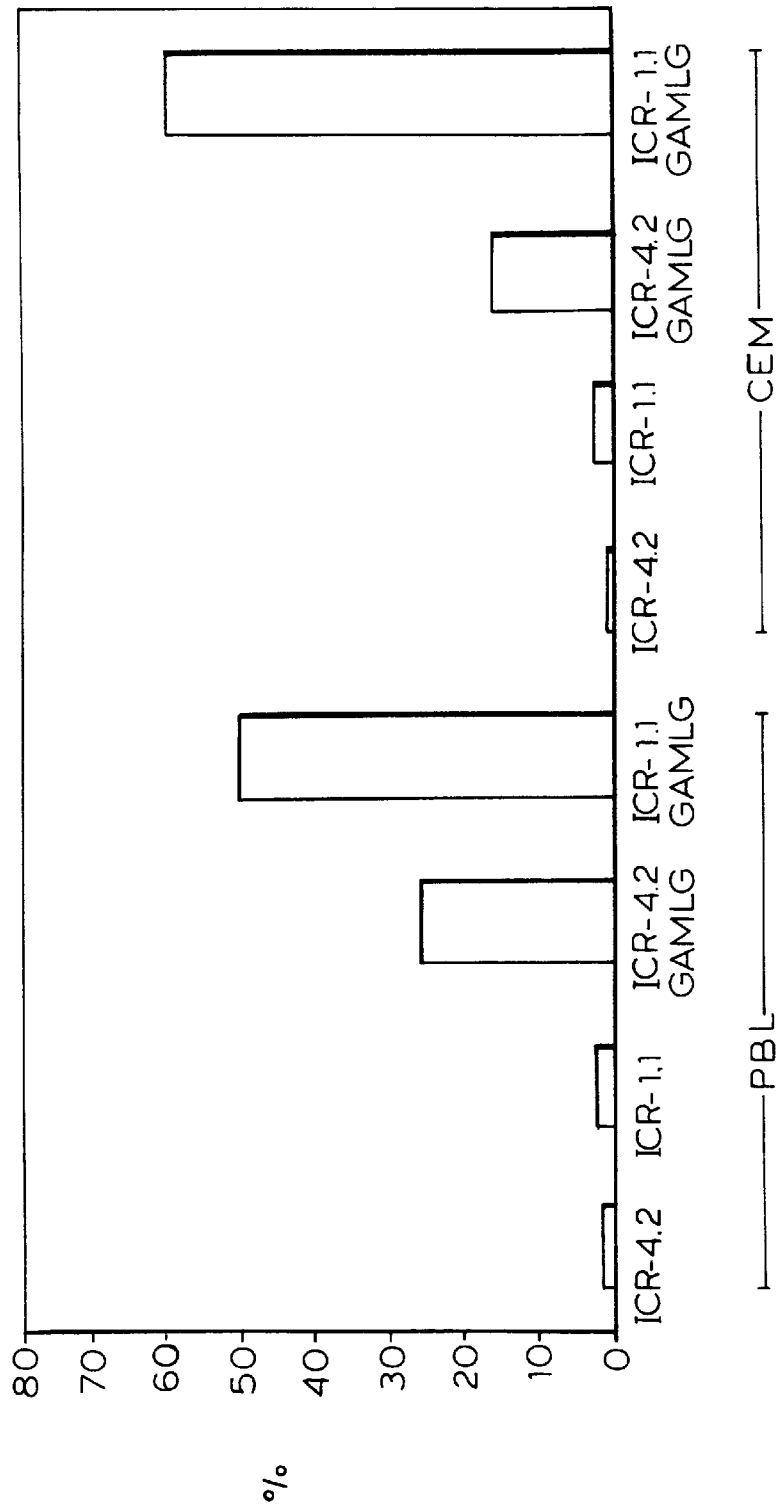
FIG. 15 comprises a bar graph illustrating that crosslinking distinct ICAM-R epitopes differentially affects ICAM-R association with the cytoskeleton.

Results (see FIG. 15) obtained for CEM cells were similar to those seen with PBL. ICAM-R association with the cytoskeleton as assessed by the detergent resistance assay was negligible when FITC-conjugated ICR-4.2 or ICR-1.1 antibodies alone were permitted to bind to cell surface ICAM-R. However, when cell surface-bound ICR-4.2 antibody was crosslinked with secondary antibodies, a modest increase in detergent resistance was detected. If secondary antibodies were used to crosslink cell surface-bound ICR-1.1, which recognizes a distinct ICAM-R epitope from that seen by ICR-4.2, a much greater (approximately 2-fold in PBL and 2–3 fold in CEM) increase in detergent resistance was reproducibly observed. Interaction of ICAM-R ligands with different structural regions of ICAM-R thus appears to differentially influence association of ICAM-R with the cytoskeleton.

The foregoing illustrative examples relate to presently preferred embodiments of the invention and numerous modifications and variations thereof will be expected to occur to those skilled in the art.

Clearly, polynucleotides (e.g., DNA and RNA) encoding ICAM-R are useful not only in securing expression of ICAM-R and variant polypeptides; they may readily be employed to identify cells (especially cells involved in immunological processes) which express ICAM-R in a normal or activated state. Typical detection assays involving ICAM-R DNA include Northern blot hybridization, RNAse protection, and in situ hybridization cytological assays wherein the DNA or RNA (in suitably labelled, detectable form) hybridizes to RNA in the sample. ICAM-R encoding DNA (especially DNA encoding the first, fourth and fifth domains which have less homology to DNAs encoding ICAM-1 and ICAM-2 than the DNAs encoding domains 2 and 3) is expected to be useful in isolating genomic DNA encoding ICAM-R including genomic DNA specifying endogenous expression control DNA sequences for ICAM-R DNA. As previously noted, knowledge of polynucleotide sequences encoding ICAM-R and/or controlling expression of ICAM-R makes available a variety of antisense polynucleotides useful in regulating expression of ICAM-R.

The present invention makes available the production of ICAM-R polypeptides and variants thereof, especially including soluble fragments thereof, such as fragments comprising one or more of the five immunoglobulin-like domains of ICAM-R in glycosylated, non-glycosylated, or de-glycosylated forms. Pharmaceutical compositions including the protein products of the invention have therapeutic potential in the modulation of immune cell activation/proliferation, e.g., as competitive inhibitors or stimulatory agents of intercellular and intracellular ligand/receptor binding reactions involving ICAM-R. Such therapeutic potential is especially projected for "immunoadhesin" type recombinant hybrid fusion proteins containing, at their amino terminal, one or more domains of ICAM-R and, at their carboxy terminal, at least one constant domain of an immunoglobulin. Such hybrid fusion proteins are likely to be available in the form of homodimers wherein the Ig portion provides for longer serum half life and the ICAM-R portion has greater affinity for the ICAM-R binding partner than ICAM-R itself. Other multimeric forms of ICAM-R which may have enhanced avidity are also projected to have therapeutic potential.

Antibody substances and binding proteins, especially monospecific antibodies including monoclonal and polyclonal antibodies, are made readily available by the present invention through the use of immunogens comprising cells naturally expressing ICAM-R, recombinant host cells producing polypeptide products of the invention, the ICAM-R polypeptide products themselves, and polypeptide products of the invention bound to an ICAM-R specific antibody that stimulates cell-cell aggregation (i.e., polypeptide products that may be in a "high affinity" binding conformation). Such antibodies and other ICAM-R specific binding proteins can be employed for immunopurification of ICAM-R and variants and in pharmaceutical compositions for therapies premised on blocking and/or stimulating the ligand/receptor binding of ICAM-R and soluble fragments thereof. For use in pharmaceutical compositions, ICAM-R specific antibody and anti-idiotypic antibody substances may be humanized (e.g., CDR-grafted) by recombinant techniques well-known in the art. Antibodies specific for distinct regions of ICAM-R may be employed in ELISA systems involving immunological "sandwiches" for monitoring inflammatory processes characterized by increases in amounts of soluble ICAM-R polypeptides in body fluids such as serum.

Inflammatory conditions which may be treated or monitored with ICAM-R related products include conditions resulting from a response of the non-specific immune system in a mammal (e.g., adult respiratory distress syndrome, multiple organ injury syndrome secondary to septicemia, multiple organ injury syndrome secondary to trauma, reperfusion injury of tissue, acute glomerulonephritis, reactive arthritis, dermatosis with acute inflammatory components, stroke, thermal injury, hemodialysis, leukapheresis, ulcerative colitis, Crohn's disease, necrotizing enterocolitis, granulocyte transfusion associated syndrome, and cytokine-induced toxicity) and conditions resulting from a response of the specific immune system in a mammal (e.g., psoriasis, organ/tissue transplant rejection and autoimmune diseases including Raynaud's syndrome, autoimmune thyroiditis, EAE, multiple sclerosis, rheumatoid arthritis and lupus erythematosus). ICAM-R products of the invention may also be useful in monitoring and treating asthma, tumor growth and/or metastasis, and viral infection (e.g., HIV infection).

Thus only such limitations as appear in the appended claims should be placed upon the scope of the present invention.

What is claimed is:

1. A method for identifying a compound that inhibits binding of ICAM-R to Mac-1, said method comprising the steps of:

(a) immobilizing ICAM-R having the amino acid sequence set forth in SEQ ID NO.: 1;

(b) detectably labelling Mac-1;

(c) incubating the labelled Mac-1 of step (b) with the immobilized ICAM-R of step (a) in the absence of the compound and determining the extent of binding of ICAM-R to Mac-1 on the basis of label bound to the immobilized ICAM-R;

(d) incubating the labelled Mac-1 of step (b) with the immobilized ICAM-R of step (a) in the presence of the compound and determining the extent of binding of ICAM-R to Mac-1 on the basis of label bound to the immobilized ICAM-R; and (e) comparing the amount of label bound in step (c) with the amount of label bound in step (d), wherein a reduction in the amount of label bound in step (d) compared to step (c) indicates that the compound inhibits binding of ICAM-R to Mac-1.

2. A method for identifying a compound that inhibits binding of ICAM-R to Mac-1, said method comprising the steps of:

(a) detectably labelling ICAM-R having the amino acid sequence set forth in SEQ ID NO.: 1;

(b) immobilizing Mac-1;

(c) incubating the labelled ICAM-R of step (a) with the immobilized Mac-1 of step (b) in the absence of the compound and determining the extent of binding of ICAM-R to Mac-1 on the basis of label bound to the immobilized Mac-1;

(d) incubating the labelled ICAM-R of step (a) with the immobilized Mac-1 of step (b) in the presence of the compound and determining the extent of binding of ICAM-R to Mac-1 on the basis of label bound to the immobilized Mac-1; and (e) comparing the amount of label bound in step (c) with the amount of label bound in step (d), wherein a reduction in the amount of label bound in step (d) compared to step (c) indicates that the compound inhibits binding of ICAM-R to Mac-1.

3. A method for identifying a compound that inhibits binding of ICAM-R to Gp 150,95, said method comprising the steps of:

(a) immobilizing ICAM-R having the amino sequence set forth in SEQ ID NO.: 1;

(b) detectably labelling Gp 150,95;

(c) incubating the labelled Gp 150,95 of step (b) with the immobilized ICAM-R of step (a) in the absence of the compound and determining the extent of binding of ICAM-R to Gp 150,95 on the basis of label bound to the immobilized ICAM-R;

(d) incubating the labelled Gp 150,95 of step (b) with the immobilized ICAM-R of step (a) in the presence of the compound and determining the extent of binding of ICAM-R to Gp 150,95 on the basis of label bound to the immobilized ICAM-R; and (e) comparing the amount of label bound in step (c) with the amount of label bound in step (d), wherein a reduction in the amount of label bound in step (d) compared to step (c) indicates that the compound inhibits binding of ICAM-R to Gp 150,95.

4. A method for identifying a compound that inhibits binding of ICAM-R to Gp 150,95, said method comprising the steps of:

(a) detectably labelling ICAM-R having the amino acid sequence set forth in SEQ ID NO.: 1;

(b) immobilizing Gp 150,95;

(c) incubating the labelled ICAM-R of step (a) with the immobilized Gp 150,95 of step (b) in the absence of the compound and determining the extent of binding of ICAM-R to Gp 150,95 on the basis of label bound to the immobilized Gp 150,95;

(d) incubating the labelled ICAM-R of step (a) with the immobilized Gp 150,95 of step (b) in the presence of the compound and determining the extent of binding of ICAM-R to Gp 150,95 on the basis of label bound to the immobilized Gp 150,95; and (e) comparing the amount of label bound in step (c) with the amount of label bound in step (d), wherein a reduction in the amount of label bound in step (d) compared to step (c) indicates that the compound inhibits binding of ICAM-R to Gp 150,95.

* * * * *

UNITED STATES PATENT AND TRADEMARK OFFICE
CERTIFICATE OF CORRECTION

PATENT NO. : 6,153,395
DATED : November 28, 2000
INVENTOR(S) : Gallatin et al.

It is certified that error appears in the above-identified patent and that said Letters Patent is hereby corrected as shown below:

Column 8,
Line 36, replace "N-X-G-X-Y-X-C-X-V or A)" with -- N-X-G-X-Y-X-C-X-(V or A) --.

Column 10,
Line 46, replace "9-well plate" with -- 96-well plate --.

Column 18,
Line 65, replace "laboratories" with -- Laboratories --.

Column 19,
Line 41, replace "βN-strand" with -- β-strand --.

Column 20,
Line 14, replace "ceUs" with -- cells --.

Column 22,
Line 8, replace "6°C" with -- 65°C --.
Line 49, replace "pBBIII-CAM-Rtl" with -- pBBIII-ICAM-Rtl --.

Column 24,
Line 61, replace "In wtro" with -- *In vitro* --.

Column 26,
Line 50, replace "ELIPA" with -- ELIFA --.

Column 28,
Line 60, replace "by.FACS" with -- by FACS --.

Column 30,
Line 44, replace "are give in" with -- are given in --.

UNITED STATES PATENT AND TRADEMARK OFFICE
CERTIFICATE OF CORRECTION

PATENT NO. : 6,153,395
DATED : November 28, 2000
INVENTOR(S) : Gallatin et al.

It is certified that error appears in the above-identified patent and that said Letters Patent is hereby corrected as shown below:

Column 32,
Line 48, replace "AU" with -- All --.

Column 35,
Line 32, replace "thejunction" with -- the junction --.

Column 46,
Line 20, replace "96well microtest" with -- 96-well microtest --.

Column 48,
Line 59, replace "ICR-42" with -- ICR-4.2 --.

Column 50,
Line 19, replace "34 hours" with -- 3-4 hours --.

Column 52,
Line 40, replace "antibodies" with -- antibodies --.

Column 54,
Line 35, replace "3H-thymidine" with -- $^{3}$H-thymidine --.

Signed and Sealed this

Fifth Day of March, 2002

*Attest:*

*Attesting Officer*

JAMES E. ROGAN
*Director of the United States Patent and Trademark Office*

SEQUENCE LISTING (1) GENERAL INFORMATION:

(iii) NUMBER OF SEQUENCES: 45

(2) INFORMATION FOR SEQ ID NO:1:

(i) SEQUENCE CHARACTERISTICS:
      (A) LENGTH: 547 amino acids
      (B) TYPE: amino acid
      (D) TOPOLOGY: linear (ii) MOLECULE TYPE: protein (ix) FEATURE:
      (A) NAME/KEY: Protein
      (B) LOCATION: 30..547

(xi) SEQUENCE DESCRIPTION: SEQ ID NO:1:

```
Met Ala Thr Met Val Pro Ser Val Leu Trp Pro Arg Ala Cys Trp Thr
            -25                 -20                 -15

Leu Leu Val Cys Cys Leu Leu Thr Pro Gly Val Gln Gly Gln Glu Phe
        -10                  -5                   1

Leu Leu Arg Val Glu Pro Gln Asn Pro Val Leu Ser Ala Gly Gly Ser
     5                  10                  15

Leu Phe Val Asn Cys Ser Thr Asp Cys Pro Ser Ser Glu Lys Ile Ala
 20                 25                  30                  35

Leu Glu Thr Ser Leu Ser Lys Glu Leu Val Ala Ser Gly Met Gly Trp
                40                  45                  50

Ala Ala Phe Asn Leu Ser Asn Val Thr Gly Asn Ser Arg Ile Leu Cys
             55                  60                  65

Ser Val Tyr Cys Asn Gly Ser Gln Ile Thr Gly Ser Ser Asn Ile Thr
         70                  75                  80

Val Tyr Gly Leu Pro Glu Arg Val Glu Leu Ala Pro Leu Pro Pro Trp
     85                  90                  95

Gln Pro Val Gly Gln Asn Phe Thr Leu Arg Cys Gln Val Glu Gly Gly
100                 105                 110                 115

Ser Pro Arg Thr Ser Leu Thr Val Val Leu Leu Arg Trp Glu Glu Glu
                120                 125                 130

Leu Ser Arg Gln Pro Ala Val Glu Glu Pro Ala Glu Val Thr Ala Thr
             135                 140                 145

Val Leu Ala Ser Arg Asp Asp His Gly Ala Pro Phe Ser Cys Arg Thr
         150                 155                 160

Glu Leu Asp Met Gln Pro Gln Gly Leu Gly Leu Phe Val Asn Thr Ser
     165                 170                 175

Ala Pro Arg Gln Leu Arg Thr Phe Val Leu Pro Val Thr Pro Pro Arg
180                 185                 190                 195
```

```
Leu Val Ala Pro Arg Phe Leu Glu Val Glu Thr Ser Trp Pro Val Asp
            200                 205                 210
Cys Thr Leu Asp Gly Leu Phe Pro Ala Ser Glu Ala Gln Val Tyr Leu
            215                 220                 225
Ala Leu Gly Asp Gln Met Leu Asn Ala Thr Val Met Asn His Gly Asp
            230                 235                 240
Thr Leu Thr Ala Thr Ala Thr Ala Thr Ala Arg Ala Asp Gln Glu Gly
            245                 250                 255
Ala Arg Glu Ile Val Cys Asn Val Thr Leu Gly Gly Glu Arg Arg Glu
260                 265                 270                 275
Ala Arg Glu Asn Leu Thr Val Phe Ser Phe Leu Gly Pro Ile Val Asn
                280                 285                 290
Leu Ser Glu Pro Thr Ala His Glu Gly Ser Thr Val Thr Val Ser Cys
            295                 300                 305
Met Ala Gly Ala Arg Val Gln Val Thr Leu Asp Gly Val Pro Ala Ala
            310                 315                 320
Ala Pro Gly Gln Thr Ala Gln Leu Gln Leu Asn Ala Thr Glu Ser Asp
            325                 330                 335
Asp Gly Arg Ser Phe Phe Cys Ser Ala Thr Leu Glu Val Asp Gly Glu
340                 345                 350                 355
Phe Leu His Arg Asn Ser Ser Val Gln Leu Arg Val Leu Tyr Gly Pro
            360                 365                 370
Lys Ile Asp Arg Ala Thr Cys Pro Gln His Leu Lys Trp Lys Asp Lys
            375                 380                 385
Thr Arg His Val Leu Gln Cys Gln Ala Arg Gly Asn Pro Tyr Pro Glu
            390                 395                 400
Leu Arg Cys Leu Lys Glu Gly Ser Ser Arg Glu Val Pro Val Gly Ile
            405                 410                 415
Pro Phe Phe Val Asn Val Thr His Asn Gly Thr Tyr Gln Cys Gln Ala
420                 425                 430                 435
Ser Ser Ser Arg Gly Lys Tyr Thr Leu Val Val Val Met Asp Ile Glu
                440                 445                 450
Ala Phe Ser Ser His Phe Val Pro Val Phe Ala Val Leu Leu Thr
            455                 460                 465
Leu Gly Val Val Thr Ile Val Leu Ala Leu Met Tyr Val Phe Arg Glu
            470                 475                 480
His Gln Arg Ser Gly Ser Tyr His Val Arg Glu Glu Ser Thr Tyr Leu
            485                 490                 495
Pro Leu Thr Ser Met Gln Pro Thr Glu Ala Met Gly Glu Glu Pro Ser
500                 505                 510                 515
Arg Ala Glu (2) INFORMATION FOR SEQ ID NO:2:

(i) SEQUENCE CHARACTERISTICS:
        (A) LENGTH: 1781 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:2:

CAGCTCTCTG TCAGAATGGC CACCATGGTA CCATCCGTGT TGTGGCCCAG GGCCTGCTGG      60

ACTCTGCTGG TCTGCTGTCT GCTGACCCCA GGTGTCCAGG GGCAGGAGTT CCTTTTGCGG     120
```

-continued

```
GTGGAGCCCC AGAACCCTGT GCTCTCTGCT GGAGGGTCCC TGTTTGTGAA CTGCAGTACT        180

GATTGTCCCA GCTCTGAGAA ATCGCCTTG GAGACGTCCC TATCAAAGGA GCTGGTGGCC         240

AGTGGCATGG GCTGGGCAGC CTTCAATCTC AGCAACGTGA CTGCAACAG TCGGATCCTC         300

TGCTCAGTGT ACTGCAATGG CTCCCAGATA ACAGGCTCCT CTAACATCAC CGTGTACGGG        360

CTCCCGGAGC GTGTGGAGCT GGCACCCCTG CCTCCTTGGC AGCCGGTGGG CCAGAACTTC        420

ACCCTGCGCT GCCAAGTGGA GGGTGGGTCG CCCCGGACCA GCCTCACGGT GGTGCTGCTT        480

CGCTGGGAGG AGGAGCTGAG CCGGCAGCCC GCAGTGGAGG AGCCAGCGGA GGTCACTGCC        540

ACTGTGCTGG CCAGCAGAGA CGACCACGGA GCCCCTTTCT CATGCCGCAC AGAACTGGAC        600

ATGCAGCCCC AGGGGCTGGG ACTGTTCGTG AACACCTCAG CCCCCCGCCA GCTCCGAACC        660

TTTGTCCTGC CCGTGACCCC CCCGCGCCTC GTGGCCCCCC GGTTCTTGGA GGTGGAAACG        720

TCGTGGCCGG TGGACTGCAC CCTAGACGGG CTTTTTCCAG CCTCAGAGGC CCAGGTCTAC        780

CTGGCGCTGG GGGACCAGAT GCTGAATGCG ACAGTCATGA ACCACGGGGA CACGCTAACG        840

GCCACAGCCA CAGCCACGGC GCGCGCGGAT CAGGAGGGTG CCCGGGAGAT CGTCTGCAAC        900

GTGACCCTAG GGGGCGAGAG ACGGGAGGCC CGGGAGAACT TGACGGTCTT TAGCTTCCTA        960

GGACCCATTG TGAACCTCAG CGAGCCCACC GCCCATGAGG GGTCCACAGT GACCGTGAGT       1020

TGCATGGCTG GGGCTCGAGT CCAGGTCACG CTGGACGGAG TTCCGGCCGC GGCCCCGGGG       1080

CAGACAGCTC AACTTCAGCT AAATGCTACC GAGAGTGACG ACGGACGCAG CTTCTTCTGC       1140

AGTGCCACTC TCGAGGTGGA CGGCGAGTTC TTGCACAGGA ACAGTAGCGT CCAGCTGCGA       1200

GTCCTGTATG GTCCCAAAAT TGACCGAGCC ACATGCCCCC AGCACTTGAA ATGGAAAGAT       1260

AAAACGAGAC ACGTCCTGCA GTGCCAAGCC AGGGGCAACC CGTACCCCGA GCTGCGGTGT       1320

TTGAAGGAAG GCTCCAGCCG GGAGGTGCCG GTGGGGATCC CGTTCTTCGT CAACGTAACA       1380

CATAATGGTA CTTATCAGTG CCAAGCGTCC AGCTCACGAG GCAAATACAC CCTGGTCGTG       1440

GTGATGGACA TTGAGGCTGG GAGCTCCCAC TTTGTCCCCG TCTTCGTGGC GGTGTTACTG       1500

ACCCTGGGCG TGGTGACTAT CGTACTGGCC TTAATGTACG TCTTCAGGGA GCACCAACGG       1560

AGCGGCAGTT ACCATGTTAG GGAGGAGAGC ACCTATCTGC CCCTCACGTC TATGCAGCCG       1620

ACAGAAGCAA TGGGGAAGA ACCGTCCAGA GCTGAGTGAC GCTGGGATCC GGGATCAAAG        1680

TTGGCGGGGG CTTGGCTGTG CCCTCAGATT CCGCACCAAT AAAGCCTTCA AACTCCCAAA       1740

AAAAAAAAAA AAAAAAAAAA AAAAAAAAAA AAAAAAAAA A                           1781
```

(2) INFORMATION FOR SEQ ID NO:3:

(i) SEQUENCE CHARACTERISTICS:
        (A) LENGTH: 8 amino acids
        (B) TYPE: amino acid
        (D) TOPOLOGY: linear (ii) MOLECULE TYPE: peptide (ix) FEATURE:
        (A) NAME/KEY: Modified-site
        (B) LOCATION: 4
        (D) OTHER INFORMATION: /note= "The amino acid at this
           position can be a valine, a leucine or an
           isoleucine."

(ix) FEATURE:
        (A) NAME/KEY: Modified-site
        (B) LOCATION: 6
        (D) OTHER INFORMATION: /note= "The amino acid at this
           position can be a valine, a leucine or an
           isoleucine."

(xi) SEQUENCE DESCRIPTION: SEQ ID NO:3:

Gly Xaa Xaa Xaa Xaa Xaa Xaa Cys
1               5

(2) INFORMATION FOR SEQ ID NO:4:

(i) SEQUENCE CHARACTERISTICS:
        (A) LENGTH: 9 amino acids
        (B) TYPE: amino acid
        (D) TOPOLOGY: linear (ii) MOLECULE TYPE: peptide (ix) FEATURE:
        (A) NAME/KEY: Modified-site
        (B) LOCATION: 9
        (D) OTHER INFORMATION: /note= "The amino acid at this
            position can be a valine or an alanine."

(xi) SEQUENCE DESCRIPTION: SEQ ID NO:4:

Asp Xaa Gly Xaa Tyr Xaa Cys Xaa Xaa
1               5

(2) INFORMATION FOR SEQ ID NO:5:

(i) SEQUENCE CHARACTERISTICS:
        (A) LENGTH: 8 amino acids
        (B) TYPE: amino acid
        (D) TOPOLOGY: linear (ii) MOLECULE TYPE: peptide (ix) FEATURE:
        (A) NAME/KEY: Modified-site
        (B) LOCATION: 3
        (D) OTHER INFORMATION: /note= "The amino acid at this
            position can be an asparagine or a serine."

(ix) FEATURE:
        (A) NAME/KEY: Modified-site
        (B) LOCATION: 4
        (D) OTHER INFORMATION: /note= "The amino acid at this
            position can be a lysine or a phenylalanine."

(ix) FEATURE:
        (A) NAME/KEY: Modified-site
        (B) LOCATION: 6
        (D) OTHER INFORMATION: /note= "The amino acid at this
            position can be an lysine or an isoleucine."

(ix) FEATURE:
        (A) NAME/KEY: Modified-site
        (B) LOCATION: 7
        (D) OTHER INFORMATION: /note= "The amino acid at this
            position can be an arginine or a glutamic acid."

(xi) SEQUENCE DESCRIPTION: SEQ ID NO:5:

Gly Lys Xaa Xaa Thr Xaa Xaa Cys
1               5

(2) INFORMATION FOR SEQ ID NO:6:

(i) SEQUENCE CHARACTERISTICS:
        (A) LENGTH: 9 amino acids
        (B) TYPE: amino acid
        (D) TOPOLOGY: linear (ii) MOLECULE TYPE: peptide (ix) FEATURE:
        (A) NAME/KEY: Modified-site
        (B) LOCATION: 1

(D) OTHER INFORMATION: /note= "The amino acid at this
                        position can be a aspartic acid or a glutamic
                        acid."

(ix) FEATURE:
                    (A) NAME/KEY: Modified-site
                    (B) LOCATION: 2
                    (D) OTHER INFORMATION: /note= "The amino acid at this
                        position can be a histidine or an aspartic acid."

(ix) FEATURE:
                    (A) NAME/KEY: Modified-site
                    (B) LOCATION: 3
                    (D) OTHER INFORMATION: /note= "The amino acid at this
                        position can be a histidine or a glycine."

(ix) FEATURE:
                    (A) NAME/KEY: Modified-site
                    (B) LOCATION: 4
                    (D) OTHER INFORMATION: /note= "The amino acid at this
                        position can be a glycine or a histidine."

(ix) FEATURE:
                    (A) NAME/KEY: Modified-site
                    (B) LOCATION: 5
                    (D) OTHER INFORMATION: /note= "The amino acid at this
                        position can be an alanine or an arginine."

(xi) SEQUENCE DESCRIPTION: SEQ ID NO:6:

Xaa Xaa Xaa Xaa Xaa Asn Phe Ser Cys
1               5

(2) INFORMATION FOR SEQ ID NO:7:

(i) SEQUENCE CHARACTERISTICS:
                    (A) LENGTH: 31 base pairs
                    (B) TYPE: nucleic acid
                    (C) STRANDEDNESS: single
                    (D) TOPOLOGY: linear (ii) MOLECULE TYPE: DNA (xi) SEQUENCE DESCRIPTION: SEQ ID NO:7:

ATTCTGCAGG CAARAAYCTS ACHMTBMGST G                                    31

(2) INFORMATION FOR SEQ ID NO:8:

(i) SEQUENCE CHARACTERISTICS:
                    (A) LENGTH: 31 base pairs
                    (B) TYPE: nucleic acid
                    (C) STRANDEDNESS: single
                    (D) TOPOLOGY: linear (ii) MOLECULE TYPE: DNA (xi) SEQUENCE DESCRIPTION: SEQ ID NO:8:

ATTCTGCAGG CAARAGYTTY ACHMTBGART G                                    31

(2) INFORMATION FOR SEQ ID NO:9:

(i) SEQUENCE CHARACTERISTICS:
                    (A) LENGTH: 31 base pairs
                    (B) TYPE: nucleic acid
                    (C) STRANDEDNESS: single
                    (D) TOPOLOGY: linear (ii) MOLECULE TYPE: DNA (xi) SEQUENCE DESCRIPTION: SEQ ID NO:9:

ATTCTGCAGG CAARTCYTTY ACHMTBGART G                                    31

```
(2) INFORMATION FOR SEQ ID NO:10:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:10:

ATTTCTAGAR AARTTRGCSC CRTGRTSRTC                                       30

(2) INFORMATION FOR SEQ ID NO:11:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:11:

ATTTCTAGAR AARTTSCKRT GSCCRTSKTC                                       30

(2) INFORMATION FOR SEQ ID NO:12:

(i) SEQUENCE CHARACTERISTICS:
        (A) LENGTH: 25 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:12:

GAGACTCTGC ACTATGAGAC CTTCG                                            25

(2) INFORMATION FOR SEQ ID NO:13:

(i) SEQUENCE CHARACTERISTICS:
        (A) LENGTH: 26 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:13:

CAGGTGATTC TCATGCAGAG TCCAGG                                           26

(2) INFORMATION FOR SEQ ID NO:14:

(i) SEQUENCE CHARACTERISTICS:
        (A) LENGTH: 25 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:14:

CCGACATGCT GGTAAGTGTG TCCAA                                            25

(2) INFORMATION FOR SEQ ID NO:15:

(i) SEQUENCE CHARACTERISTICS:
        (A) LENGTH: 17 base pairs
```

(B) TYPE: nucleic acid
            (C) STRANDEDNESS: single
            (D) TOPOLOGY: linear (ii) MOLECULE TYPE: DNA (xi) SEQUENCE DESCRIPTION: SEQ ID NO:15:

GACCATGAGG TGCCAAG                                                          17

(2) INFORMATION FOR SEQ ID NO:16:

(i) SEQUENCE CHARACTERISTICS:
            (A) LENGTH: 17 base pairs
            (B) TYPE: nucleic acid
            (C) STRANDEDNESS: single
            (D) TOPOLOGY: linear (ii) MOLECULE TYPE: DNA (xi) SEQUENCE DESCRIPTION: SEQ ID NO:16:

ATGGTCGTCT CTGCTGG                                                          17

(2) INFORMATION FOR SEQ ID NO:17:

(i) SEQUENCE CHARACTERISTICS:
            (A) LENGTH: 18 base pairs
            (B) TYPE: nucleic acid
            (C) STRANDEDNESS: single
            (D) TOPOLOGY: linear (ii) MOLECULE TYPE: DNA (xi) SEQUENCE DESCRIPTION: SEQ ID NO:17:

TTCACCCTGC GCTGCCAA                                                         18

(2) INFORMATION FOR SEQ ID NO:18:

(i) SEQUENCE CHARACTERISTICS:
            (A) LENGTH: 18 base pairs
            (B) TYPE: nucleic acid
            (C) STRANDEDNESS: single
            (D) TOPOLOGY: linear (ii) MOLECULE TYPE: DNA (xi) SEQUENCE DESCRIPTION: SEQ ID NO:18:

AAAGGGGCTC CGTGGTCG                                                         18

(2) INFORMATION FOR SEQ ID NO:19:

(i) SEQUENCE CHARACTERISTICS:
            (A) LENGTH: 19 base pairs
            (B) TYPE: nucleic acid
            (C) STRANDEDNESS: single
            (D) TOPOLOGY: linear (ii) MOLECULE TYPE: DNA (xi) SEQUENCE DESCRIPTION: SEQ ID NO:19:

CCGGTTCTTG GAGGTGGAA                                                        19

(2) INFORMATION FOR SEQ ID NO:20:

(i) SEQUENCE CHARACTERISTICS:
            (A) LENGTH: 20 base pairs
            (B) TYPE: nucleic acid
            (C) STRANDEDNESS: single
            (D) TOPOLOGY: linear (ii) MOLECULE TYPE: DNA (xi) SEQUENCE DESCRIPTION: SEQ ID NO:20:

CATGACTGTC GCATTCAGCA                                                    20

(2) INFORMATION FOR SEQ ID NO:21:

(i) SEQUENCE CHARACTERISTICS:
             (A) LENGTH: 18 base pairs
             (B) TYPE: nucleic acid
             (C) STRANDEDNESS: single
             (D) TOPOLOGY: linear (ii) MOLECULE TYPE: DNA (xi) SEQUENCE DESCRIPTION: SEQ ID NO:21:

GCAAGAACCT TACCCTAC                                                      18

(2) INFORMATION FOR SEQ ID NO:22:

(i) SEQUENCE CHARACTERISTICS:
             (A) LENGTH: 19 base pairs
             (B) TYPE: nucleic acid
             (C) STRANDEDNESS: single
             (D) TOPOLOGY: linear (ii) MOLECULE TYPE: DNA (xi) SEQUENCE DESCRIPTION: SEQ ID NO:22:

GAAATTGGCT CCATGGTGA                                                     19

(2) INFORMATION FOR SEQ ID NO:23:

(i) SEQUENCE CHARACTERISTICS:
             (A) LENGTH: 315 base pairs
             (B) TYPE: nucleic acid
             (C) STRANDEDNESS: single
             (D) TOPOLOGY: linear (ii) MOLECULE TYPE: DNA (genomic)

(ix) FEATURE:
             (A) NAME/KEY: CDS
             (B) LOCATION: 1..315

(xi) SEQUENCE DESCRIPTION: SEQ ID NO:23:

CCG GAT CGG GTA GAG CTA GTG CCT CTG CCT CCT TGG CAG CCT GTA GGT           48
Pro Asp Arg Val Glu Leu Val Pro Leu Pro Pro Trp Gln Pro Val Gly
  1               5                  10                  15

GAG AAC TTC ACC TTG AGC TGC AGG GTC CCG GGG GCA GGA CCC CGA GCG           96
Glu Asn Phe Thr Leu Ser Cys Arg Val Pro Gly Ala Gly Pro Arg Ala
                 20                  25                  30

AGC CTC ACA TTG ACC TTG CTG CGA GGC GGA CAG GAG CTG ATT CGC CGA          144
Ser Leu Thr Leu Thr Leu Leu Arg Gly Gly Gln Glu Leu Ile Arg Arg
             35                  40                  45

AGT TTC GTA GGC GAG CCA CCC CGA GCT CGG TGT GCG ATG CTC ACC GCC          192
Ser Phe Val Gly Glu Pro Pro Arg Ala Arg Cys Ala Met Leu Thr Ala
         50                  55                  60

ACG GTC CTG GCG CGC AGA GAG GAT CAC AGG GAC AAT TTC TCA TGC CTC          240
Thr Val Leu Ala Arg Arg Glu Asp His Arg Asp Asn Phe Ser Cys Leu
 65                  70                  75                  80

GCG GAG CTT GAC CTG CGG ACA CAC GGC TTG GGA CTG TTT GCA AAC AGC          288
Ala Glu Leu Asp Leu Arg Thr His Gly Leu Gly Leu Phe Ala Asn Ser
                 85                  90                  95

TCA GCC CCC AGA CAG CTC CGC ACG TTT                                      315
Ser Ala Pro Arg Gln Leu Arg Thr Phe (2) INFORMATION FOR SEQ ID NO:24:

(i) SEQUENCE CHARACTERISTICS:
        (A) LENGTH: 105 amino acids
        (B) TYPE: amino acid
        (D) TOPOLOGY: linear (ii) MOLECULE TYPE: protein (xi) SEQUENCE DESCRIPTION: SEQ ID NO:24:

```
Pro Asp Arg Val Glu Leu Val Pro Leu Pro Pro Trp Gln Pro Val Gly
 1               5                  10                  15

Glu Asn Phe Thr Leu Ser Cys Arg Val Pro Gly Ala Gly Pro Arg Ala
            20                  25                  30

Ser Leu Thr Leu Thr Leu Leu Arg Gly Gly Gln Glu Leu Ile Arg Arg
        35                  40                  45

Ser Phe Val Gly Glu Pro Pro Arg Ala Arg Cys Ala Met Leu Thr Ala
    50                  55                  60

Thr Val Leu Ala Arg Arg Glu Asp His Arg Asp Asn Phe Ser Cys Leu
65                  70                  75                  80

Ala Glu Leu Asp Leu Arg Thr His Gly Leu Gly Leu Phe Ala Asn Ser
                85                  90                  95

Ser Ala Pro Arg Gln Leu Arg Thr Phe
            100                 105
```

(2) INFORMATION FOR SEQ ID NO:25:

(i) SEQUENCE CHARACTERISTICS:
        (A) LENGTH: 1295 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:25:

```
NGAATTCCGG CGGATCGGGT AGAGCTAGTG CCTCTGCCTC CTTGGCAGCC TGTAGGTGAG     60

AACTTCACCT TGAGCTGCAG GGTCCCGGGG GCAGGACCCC GAGCGAGCCT CACATTGACC    120

TTGCTGCGAG GCGGCCAGGA GCTGATTCGC CGAAGTTTCG TAGGCGAGCC ACCCCGAGCT    180

CGGGGTGCGA TGCTCACCGC CACGGTCCTG GCGCGCAGAG AGGATCACAG GGCCAATTTC    240

TCATGCCTCG CGGAGCTTGA CCTGCGGCCA CACGGCTTGG GACTGTTTGC AAACAGCTCA    300

GCCCCCAGAC AGCTCCGCAC GTTTGCCATG CCTCCACTTT CCCCGAGCCT TATTGCCCCA    360

CGATTCTTAG AAGTGGGCTC AGAAAGGCCG GTGACTTGCA CTTTGGATGG ACTGTTTCCT    420

GCCCCAGAAG CCGGGGTTTA CCTCTCTCTG GGAGATCAGA GGCTTCATCC TAATGTGACC    480

CTCGACGGGG AGAGCCTTGT GGCCACTGCC ACAGCTACAG CAAGTGAAGA ACAGGAAGGC    540

ACCAAACAGC TGATGTGCAT CGTGACCCTC GGGGGCGAAA GCAGGGAGAC CCAGGAAAAC    600

CTGACTGTCT ACAGCTTCCC GGCTCCTCTT CTGACTTTAA GTGAGCCAGA AGCCCCCGAG    660

GGAAAGATGG TGACCGTAAG CTGCTGGGCA GGGGCCCGAG CCCTTGTCAC CTTGGAGGGA    720

ATTCCAAGGA CCCTCTTACC GGCCCCATCT TTAACCTTAT CGTATCCCCT CTGCCTCATG    780

CCCGCAGACG CACCTCGGCT GGATGACTTG GACTGTCCCA GGAGCTGGAC GTGGCCAGAG    840

GGTCCAGAGC AGACCCTCCA CTGCGAGGCC CGTGGAAACC CTGAGCCCTC CGTGCACTGT    900

GCAAGGCCTG ACGGTGGGGC GGTGCTAGCG CTGGGCCTGT TGGGTCCAGT GACCCGTGCC    960
```

-continued

```
CTCGCGGGCA CTTACCGATG TACAGCAATC AATGGGCAAG GCCAGGCGGT CAAGGATGTG    1020

ACCCTGACTG TGGAATATGC CCCAGCGCTG GACAGTGTAG GCTGCCCAGA ACGTATTACT    1080

TGGCTGGAGG GGACAGAGGC ATCGCTTAGC TGTGTGGCAC ACGGGGTCCC ACCACCTAGC    1140

GTGAGCTGTG TGCGCTCTGG AAAGGAGGAA GTCATGGAAG GGCCCCTGCG TTTTGGCCGG    1200

GAGCACGCTG GCACTTACCG ATGCGAAGCC ATCAACGCCA GGGGATCAGC GGCCAAAAAT    1260

GTGGCTGTCA CGGTGGAATA TGGTCCCCGG AATTC                               1295
```

(2) INFORMATION FOR SEQ ID NO:26:

(i) SEQUENCE CHARACTERISTICS:
        (A) LENGTH: 4900 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:26:

```
CCGAACGCTC CTCGGCCTCT GGTCTNCTCT GGNCCTGGGG ATCCTAGGCA TCTCAGGTAA      60

GAAGAGCCCG CCCGTGGAGC NAGGTGGATA AGGCGGGGC GGAATTGAAG GACCAGAGAG      120

GGCGGCCCGG GTGTCCCCCT CCAGGCTCCG CCCTCTTCTA GCTTCCCACG CTTCTGTCAC     180

CACCTGGAGN TCGGGGCTTC TCCCCGTCCT TCCTCCACCC CAACACACCT CAATCTTTCA     240

GANCTGAACC CAGCACCTTT TCTGGANTNG GGGNNTTGCA CCTAACCTGT CTCAGGAGAN     300

ACTGTGGCTC TCCTGTCCTC TCCTGCTCTG TNATGCCCTA TGGTTCACAG ACTGGCATCA     360

TCCCTATTCA TGATCCTCAA AGACNCCATC TCCTCAACTG TCATAACTCA GAGCTCTATT     420

CCCCCTCCAC CTGGAGCCCT GGAAACCGGC TTTCTAGGGC TTTTCTCCGC GGTTCTTTCC     480

CGGAGTTCAG CGTTGTGGCT TTTTGTCCAA GTTACTCAAG TTTGGGGACA ATCTCCTTTA     540

AGCCTTTGAC TCAGTCTCAT TTCCACTTTG CTTTTGCCCC AAGCCTCTGT GTCTCTCCCC     600

CATTTCCTGA CGATCTGTCA GAGTCTTAAG AGTGATTTGG TTCCCCATCC CCCTCCAAC     660

TGGAGTCTCC TCCTCACTAT TGATGTGTGC ATCTGAGACC CCCATCCCCG CACCGAGTTT     720

CCCCATCTCT GTCAGTAAAG AGCAAGGCTT CCAGAGACAA CCCTCTAATA GCGCGTCAGT     780

CCCGAATCTT GAGTGGGATG CGGGACTCCC GTGCTATTTC TTGGCGGAGG TCTTTCCTGG    840

TCCTTATGGA CACCCCTGGT TTGGGATATG GGGGCCGCTA AGATTTCAGA GATGGGGTCC    900

CTAGGCTGAG NCCGCGTTTT CCCGGGCAGC GGTCGCGCTA GAACCTTTCT GGGCGGACCT    960

TCAGCCCCGC GTGGCGCTCG TGGAGCGCGG GGGCTCGCTG TGGCTCAACT GCAGCACTAA    1020

CTGTCCGAGG CCGGAGCGCG GTGGCCTGGA GACCTCGCTA CGCCGAAACG GGACCCAGAG    1080

GGGTCTGNAC TGNCTGGCTC GACAGCTGGT GGACATCCGA GANCCTGAAA CCCAGCCGGT    1140

CTGCTTCTTC CNCTGCGCGC GCCGCACACT CCAAGCGCGT GGGCTCATCC GAACTTTCCG    1200

TGAGTTCAGG GTGGGCACNC CCCTTGGGTC TCTGGACCTC CCCCTCAAGC TCCTCCCACC    1260

CGCCCTCTGA TCCTCCTGCT TGTTCTGAAA GTACTACAGC TGGCTAGAGC GGAGTTTTTG    1320

GTCCCTTGCA GAGCGACCGG ATCGGGTAGA GCTAGTGCCT CTGCCTCCTT GGCAGCCTGT    1380

AGGTGAGAAC TTCACCTTGA GCTGCAGGGT CCCGGGGGCA GGACCCCGAG CGAGCCTCAC    1440

ATTGACCTTG CTGCGAGGCG GCCAGGAGCT GATTCGCCGA AGTTTCGTAG GCGAGCCACC    1500

CCGAGCTCGG GGTGCGATGC TCACCGCCAC GGTCCTGGCC CGCAGAGAGG ATCACAGGGC    1560

CAATTTCTCA TGCCTCGCGG AGCTTGACCT GCGNCCACAC GGCTTGGGAC TGTTTGCANA    1620
```

-continued

```
CAGCTCAGCC CCCAGACAGC TCCGCACGTT TGGTGAGTGT GGACCCTAAC TGACAGATTT    1680

TAAGAAGTTT AGGGCAGCCA GGCGTGGTGG CATGGTGTCG TAGGCCCTAA GTCCCAGCCC    1740

AAGCAGANCT AAGNCGGATC TCTTGTGAAT TAAAAGTCTA GCTCGTCTAC ATAACGAGGN    1800

CTGCATAGTT AAATCCCCCA AAAGTCTAAG CAGCTAGCCC TTACTTCCAA CACAAGTACT    1860

AGCTTAAGTA CTTTCTCCTG TGAGCTTTTT CCTTTATGTA TTTACTCGTT GAGAGAAAAA    1920

GAGAGTGTGT GTACGTGCCT TTATGCACAT GCCGCAGTGC TTGTATGGAA GTTAAAGAAT    1980

AAGGAGGCGT TCTGCCCTTC CATCCTGTGG GTCCTAGGGG TGGTATTAGC TCCTCAGGCT    2040

TTGTTAGTNA CAAGCGCCTA GGCTTGGGGA GCCATCTCGC CCGCTCCTCT GTATCTTTAG    2100

GGTGAAACCA GACAATGCAT GCAAATTGGT TGATCAACAC TGAATGTTTA GTTCGTAAAT    2160

TCAAGCTCTG TTCTTTGTCT TCCTCAGCCA TGCCTCCACT TTCCCCCGAG CCTTATTGCC    2220

CCACGATTCT TAGAAGTGGG CTCAGAAAGG CCGGTGACKT GCACTTTGGA TGGACTGTTT    2280

CCTGCCCCAG AAGCCGGGGT TTACTTCTCT CTGGGAGATC AGAGGCTTCA TCCTAATGTG    2340

ACCCTCGACG GGGAGAGCCT TGTGGCCACT GCCACAGCTA CAGCAAGTGA AGAACAGGAA    2400

GGCACCAAAC AGCTGATGTG CATCGTGACC CTCGGGGGCG AAAGCAGGGA GACCCAGGAA    2460

AACCTGACTG TCTACAGTAA GGGGAATCCA ACAAGACCTT CAATAGCTCA GACTGGGGCT    2520

GGGGCTGGGT CTGGGTCTGG GGCCAGAGTC TCACAAAGGC GGAGCCTATA AGTGGGCGG    2580

GACCTCCACA CCAGAACAAG CCGGGCGGGA GAGTTCCAGG GCAGGAGCAG ATAGAAGTTG    2640

GAAATTAATA GATTGGGTTG AGTTCCCTGA GTGGGGAGTG AACCCCACCC AATTCTCTGT    2700

CCCCAGGCTT CCCGGCTCCT CTTCTGACTT TAAGTGAGCC AGAAGCCCCC GAGGGAAAGA    2760

TGGTGACCGT AAGCTGCTGG GCAGGGGCCC GAGCCCTTGT CACCTTGGAG GGAATTCCAA    2820

GGACCCTCTT ACCGGCCCCA TCTTTAACCT TATCGTATCC CCTCTGCCTC ATGCCCGCAG    2880

ACGCACCTCG GCTGGATGAC TTGGACTGTC CCAGGAGCTG GACGTGGCCA GAGGGTCCAG    2940

AGCAGACCCC CCACTGCGAG GCCCGTGGAA ACCCTGAGCC CTCCGTGCAC TGTGCAAGGC    3000

CTGACGGTGG GGCGGTGCTA GCGCTGGGCC TGTTGGGTCC AGTGACCCGT GCCCTCGCGG    3060

GCACTTACCG ATGTACAGCA ATCAATGGGC AAGGCCAGGC GGTCAAGGAT GTGACCCTGA    3120

CTGTGGAATG TGAGTAGGGG GAGGTGGGCA TGCTTATCCC TTTAAGGTCA CGGAGTGTAC    3180

TGGGAGACTG GCTATACGGA AAGGAAAGAA GCCTAGGTTC AGCAGGGATT GGGAAAACAC    3240

TGAAGGAAAG TGGTGTGGTG TTTACAAACT TAACGGTGGT AACTGGGCAC GGTCTGGCAA    3300

AAACAGACAG CCAAGAGAGT GTGCCTGGGA AGCTGCAATG GGGGCTTTGT GGGAATTGGT    3360

CAACAGCACC CTGAGATCTC AGGAAAGGGG CCTGAAGTTA TCTCCAGAAC CCATGTGAAG    3420

GCAGGAAGAG AGAACGCCCA CCTTTTCCTG CTCCCCCCAA CCCCCCCCCA CATATCACAC    3480

GGAGTATATA AATAAATAAA ATGGCTCCTG CCGGAGGGAG TGAGAAGCTG TCTCCTGCAG    3540

GCTCAGAGCA GTGGTAGTGC ATGCCTTTAA TCCCAGCACT CGGTAGGCAA AGGCAGGCAG    3600

ATCTCTGTGA ATGTGGGGCC AGCCTGGTCT GTACAGAGAA ATCCTGTCTC AAAACAAACC    3660

AGCAAAGAAA CAAAACCAAA ATCAATTCCA GATGCCCCAG CGCTGGACAG TGTAGGCTGC    3720

CCANGACGTA TTACTTGNCT GGAGGGGACA GAGGCATCGC TTAGCTGTGT GGCACACGGG    3780

GTCCCACCAC CTAGCGTGAG CTGTGTGCGC TCTGGAAAGG AGGAAGTCAT GGAAGGGCCC    3840

CTGCGTGTGG CCCGGGAGCA CGCTGGCACT TACCGATGCG AAGCCATCAA CGCCAGGGGA    3900

TCAGCGGNCA AAAATGTGGC TGTCACGGTG GAATGTGAGT AGGGGTGGCT ACGGAAATGT    3960
```

```
CCACACCTGC GTCCTCTGTC CTCAGTGTGA ACTCCTATTT CCCTGCTTCC TAGATGGTCC      4020

CAGTTNTGAG GAGTTGGGCT GCCCCAGCAA CTGGACTTGG GTAGAAGGAT CTGGAAAACT      4080

GTTTTCCTGT GAAGTTGATG GGAAGCCGGA ACCACGCGTG GAGTGCGTGG GCTCGGAGGG      4140

TGCAAGCGAA GGGGTAGTGT TGCCCCTGGT GTCCTCGAAC TCTGGTTCCA GAAACTCTAT      4200

GACTCCTGGT AACCTGTCAC CGGGTATTTA CCTCTGCAAC GCCACCAACC GGCATGGCTC      4260

CACAGTCAAA ACAGTCGTCG TGAGCGCGGA ATGTGAGCAG GGGCCCAGGT GGGCGGAGAG      4320

TACCGGGTGT CCCAGGATCT TTTCTTTCCC TGATGCCCCT CCTTATGGTG GCTGATCTGC      4380

AGCACCGCCA CAGATGGATG AATCCAGTTG CCCGAGTCAC CAGACATGGC TGGAAGGAGC      4440

CGAGGCTACT GCGCTGGCCT GCAGTGACAG GGGNCGCCCC TCTCCACGCG TGCGCTGTTC      4500

CAGGGAAGGT GCAGCCAGGC TGGAGAGGCT ACAGGTGTCC CGAGAGGATG CGGGGACCTA      4560

CCTGTGTGTG GCTACCAACG CGCATGGCAC GGATTCACGG ACCGTCACTG TGGGTGTGGA      4620

ATGTGAGTGA GGACAGCGCT GAATGAAGAC GACTCAGACC GCCAGAAAAG TGCCTTGAGG      4680

CCTGGGATGT ATGATCCAGT GGGTAGAGTG CTCAATTAGC ACTCACTAAA ATGTATATTC      4740

TATTCCTAAT ACTCTTTAAT TTTANCCTTT GGGAGGCAGA GACAGGCAGA TCTCTGTTCC      4800

GGGATAACCT GCTCTCTGTC TAGGACAGCT TGGTCTACAG AGGGGNTACA GGCCCCCCCT      4860

CCCAAGATTG NATAGCAACC CTCTGGCTCC CTGTCTCTCT                            4900
```

(2) INFORMATION FOR SEQ ID NO:27:

(i) SEQUENCE CHARACTERISTICS:
        (A) LENGTH: 4533 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:27:

```
AAGCTTGCAT GCCTGCAGGT CGACTCTAGA GGATCCTAGG CATCTCAGGT AAAGAAGANC        60

CCGCCGNCGG AGCCAGGTGG ATAAGGCGGG GGCGGAATTG AAGGACCAGA GAGGGCGGCC       120

CGGGTGTCCC CTCCAGGCTC CGCCCTCTTC TAGCTTCCCA CGCTTCTGCC ACCACCTGGA       180

GCTCCGGGCT TCTCCCTGTC CTTCCTCCAC CCCAACACAC CTCGATCTTT CAGANNGGAA       240

NCCAGCACCT TTTCTGAANT NGGGGTNTTG CACCCAACCT GGCTCAGGAG ANACTGTGGC       300

TCTCCTGTTC TCTCCTGCTC TGTCGTGTCC TATGGTTCAC AGACTAGCAT CATCCCTATT       360

TATGATCCTC AAAGACCCTA TCTCCTCAAC TGTCATAACT CAGAGGCCCT GTTTCCCCTC       420

CACCTGGAGC CCTGNCAACC GGCTTTCTAG GGCTTTCCTC ANGGTTCCTT CCNGGAATCT       480

AACCTTGTGG CTTTCTGTCC AAGTTACTCA AGTTTGGGGA CAATCTCCTT TAAGCCTTTG       540

ACTCAGTCTC TCATTTCTAC TTTGCTTTCG CCCCCAGCCT NGGTGTCTCT CCCCCCCATT       600

TCCTGACGAC CTGTCAGGGT CTTAAGAGTG ACTTGGTTCC CCATCCCCCC AAATTGGAAT       660

CTCCTCCTCC TCACTATTGA TGTGTTCATC TGAGACCCCA TCNCTGCNCC GAGCTTCCCC       720

ATCTCTNCCA TAGNCAGCAA GGCTTCCAGA GACGCCCCTC TAAGAGTGCG TCAGTCCCGA       780

ATCTTGAGTG GGATGCGGGA CTCCCGTGCT ATTTCTTGGC GGTGGTCTTT CCTCGTCCTT       840

ACAGACACCC CTGGTTTGGG AGATGGGGGC CACTAAGATT TCAGAGATGG GGTCCCTAGG       900

CTGAGCCCGC GTTTTCCTGG GCAGCGGTCG CGCTAGAACC TTTCTGGGCG GACCTTCARC       960

CACCGCGTGK CGCTCGTGGA GCRCGGGGGC TCYCTGTGKC TCAACTGCAG CACTAACTGT      1020
```

-continued

| | |
|---|---|
| CCNCGNCCGG AGCRCGGTGK CCTGGAGACC TCNCTACRCC GAAACGGGAN CCAGAGGGGT | 1080 |
| CTNCKCTGNC TGNCTCGNCA GCTGGTGGAC ATCCGAGANC CTGAGANCCA NCNGGTCTGC | 1140 |
| TTCTTCCGCT GCGCGCGCCK CACACTCCAA GCGCGTGGAC TCATCCGAAC TTTCCGTGAG | 1200 |
| TACAGTGTGR ACACNCCCCT TGGNTGCCCT GGACCTCCCC CTAAAGCTCC GCCCACCCGT | 1260 |
| TCTCTGGTCC TCCTTCCTAG GCTTGTNCTG AGANCACTAC AGCTCGCTAA AGCCCAGGTT | 1320 |
| TTGGTCCCTT GCAGANCGAC CGGATCGGGT AGANCTGGTN CCGCTCCCTT CTTGGCAGCC | 1380 |
| AGTGGGCGAG AACTTCACCT TGANCTGCAG GKYCCNGGKA GCAGGACCCC GAGCGAGCCT | 1440 |
| CACATTGACC CTGCTGCGGG GCGGCCAGGA GCTGATTCGC CGCAGTTTCG TAGGCGAGCC | 1500 |
| ACCCCGAGCG CGGGGTGCGA TGCTCACCGC CAGGGTCCTG GCACGCAGGG AGGACCACAG | 1560 |
| GGTCAATTTC TCATGCNTCG CCGANCNTGA GCTNNNNNNN NNNNNNNNNN NNNNNNNNNN | 1620 |
| NNNNNNNNNN NNNNNNNNNN NNNNNNNNNN NNNNNNNNNN NNNNNNNNNN NNNNNNNNNN | 1680 |
| NNNNNNNNNN NNNNNNNNNN NNNNNNNNNN NNNACACTGT AGCTGTCTTC AGACACACCA | 1740 |
| GAAGAGGGCG TCAGATCTCA TNACAGATGG NTGTGANCCA CCATGTGGNT CCTGGGATTT | 1800 |
| GNACTTCGGA CCTNCGSAAG AGCAGTCGGG TGCTCTTACC CACTTGAGCC ATCTCTCCAG | 1860 |
| NCCCAAGTGC TTTCTTCTGY GGTCTTYTTC TTTATGCATT TATTTATTGA GAGAAAAAGA | 1920 |
| GAGTGTGTGT ATATGCGTTT ATGCACATGC CACAGTGCAT GTGTGGAAGT TAAAGGATAA | 1980 |
| GTAGGAGTTT AGTTCTCTCT TTCCATCATG TAGGTCCTGG GGATCGAGTC AAGTCAGGCT | 2040 |
| TAACAACAAG CACCTAAACT TGTGGTGCCA TCTCGCCCGC CCTTCTGTAT TTTTAGGATG | 2100 |
| AAACCAAACA ATGCATGCAA ATTGGCTTGT CAACACTGAA TGCTTAGTTC ATAAACTCAA | 2160 |
| ATCCTGTTCT TTGTCCGCCC CAGCCATGCC TCCACATTNC CCCGAGTCTT ATTGCTCCCC | 2220 |
| GAGTCTTAGA AGTGGACTCA GAAAGNCCGG TGANKTSCAC GWTGGATGGA CTGTTTCCTG | 2280 |
| CCCCAGAAGC CGGGGTTTAC CTCTCTCTGG GAGATCAGAG GCTCCAATCC TAATGTGACC | 2340 |
| CTCGATGGGG ACAGNCKKGC TGNCCACTGC NACAGCTACA CCAANCGCAG AACAGGAAGG | 2400 |
| CACCACNCAN CTGATGTGCG TCGTGACCCT CGGGGCGAA AGCAGGGAGA CCCAGGAAAA | 2460 |
| CCTGNCTGTT TACAGTAAGG GGAATCCAGG GGGCCTTCAT TGTCTGGGGC TGGAACCAGA | 2520 |
| GTCTCACAGA GGCGGAGCCA ATAAAGTGGG NGGGGCGTCT ACACCAGAAA AAGCAGGGCA | 2580 |
| GGAGAGTTCC AGGGCAGGAG CAGGTAGAAG CTGGAAATGA ATAAATAGAA GGGGTTGAGT | 2640 |
| TACCTGAGTG GGGAGTGAAC CCCACCCAAT TCTCCGCCCT CAGGCTTCAC CGACTCCTCT | 2700 |
| TCTGACTTTT GAGTGAGCCA GAAGCCNCCC GAGGGAAAAA ATGGTGACCA TAANCTNCTG | 2760 |
| GNCAGGGGCT CGANCCCTTG TCACCCTGGA GGGAATTCCA GCTGCGGTCC CGGGGCAGCC | 2820 |
| CNCTGAGCTC CAGNTAAATG TTACAAAGAN CGATGACAAN CGGGGCTTCT TCTNCGACNC | 2880 |
| CGCCCTCGAT GTGGTRCGGG GAAACTCTAA GAAAAAACCA GAGCTCTGAG CTTCGTGTCC | 2940 |
| TGTGTGAGTG GATGCTCACC CTANCTCTGT GACCTCCAAA GCCCCTATTA CCTGCTCCAT | 3000 |
| CYTTAACCTT ATCTATCTCC TCTGCCTCGT GCCCGCAGAT GCACCTCNCC TGGATGACTT | 3060 |
| GGATTGTCCC AGAANCTGGA CGTGNCCAGA GGGTCCAGAG CAGACCCTCY WCTGSGNGNM | 3120 |
| NMGMGRAAAC CCTGAGCCCT CGGTGCACTG TGCAAGGCCT GAGGNCGGGN CGGTGCTAGC | 3180 |
| RSTGGSCGCT ATTGGGTCCA GTGACCCGTG CCCTCGCAGG CACTTACCGA TGCACAGCAG | 3240 |
| TCAATGGGCA AGGCCAGGCG GTCAAAGATG TGACCCTGAC CGTGGAATGT GAGTCGGGAG | 3300 |
| AGGCATGCAT GCCCAAGTTC ACCGAGTTAG GGGAGACGGG CCTATACGGA CAGGAAAGAA | 3360 |
| GCTGGATTCT NCAGGGATTG GGAAAACACT GAAGGGAAGT GTAGGTGGGA CTGTGGGACT | 3420 |

```
GGGTACAGTC TGNCAAAAAC AGNCAGTCAA GAGAGTGTAC CGGGGAGTGC TTTGTGGGGW    3480

TCAGTCAGCA GCATCCTGAG ACCTCAGGAA AGGGNCCTGA TCACCTGAAG TGATGNCCAG    3540

AACCCATGTG AAGGTGGGAG GAGAGAACGC CTACCTTTTC ATGCTTTCCC ACACACATAT    3600

CGTACAGAGT AAATAGAAAA GTAAAATGGT ACATGCCAGA GTGAGAAGCT GTCTCCCGAA    3660

GGCATAGAAC AGTGGTAATN CACGCCTTTA ATCCCAGCAC CCTGTAGSCA AAGGCAGGCA    3720

CATCTCTGAG TTTGAGGCCA GCCTGGTCTA CAGAGCAAGT TCCAGNCCAG CCTGNTCTAC    3780

ATAGGGAATT CCTGTCTCAA AATAAACANA CANNAANCCA AAACCWWAGT CSATYCNAGA    3840

WGCCCCAGCG CTGGACAGTG TAGNCTGCCC AGAACATATT ACTTGNCTGG AGGGAACGGA    3900

GGCATCGCTT ANCTGTGTGG CACACGGGGT CCCACCACCT AGCGTGAGTT GTGTGCGCTC    3960

TGGAAAGGAG GAAGTCATGG AAGGGCCTCT GCGCGTGGCC CGGGAGCACG CCGGCACTTA    4020

CCGATGCGAA GCCATCAACG CCAGAGGATC AGCGNCCAAA AATGTGNCCG TCACGGTGGA    4080

ATGTGAGTAG GGGTGACTGC AGAGAAGTCC CGCACCCGCA TCCTCTGTCC TCTATGTCCA    4140

AACTCTTATT TNCCTGNTTC CKAGATGGKS MMAGTTTTGA GGAGTTGGGC TGCCCCAGCA    4200

ACTGGACGTG GGTAGAGGGA TCTGGAAAGC TGTTTTCCTG TGAAGTTGAT GGGAAGCCAG    4260

AACCACGTGT GGAGTGCGTA GGCTCGGAGG GTGCAAGCGA AGGGATAGTG TTGCCCTTGG    4320

TGTCCTCAAA CTCTGGTCCT AGAAACTCTA TGACCCCTGG TAACCTGTCA CCGGGCATTT    4380

ACCTCTGCAA CGCCACCAAC CGGCACGGCT CCACAGTCAA AACAGTCGTC GTGAGCGCGG    4440

AGTGTGAGCA GGGGCCCAGG TGGGCGGAAA GTACCGGGTG TCCCAGGATC CCCGGGTACC    4500

GAGCTCGAAT TCGCCCTATA GTGAGTCGTA GGC                                 4533

(2) INFORMATION FOR SEQ ID NO:28:

(i) SEQUENCE CHARACTERISTICS:
        (A) LENGTH: 5 amino acids
        (B) TYPE: amino acid
        (D) TOPOLOGY: linear (ii) MOLECULE TYPE: peptide (xi) SEQUENCE DESCRIPTION: SEQ ID NO:28:

Asp Gly Gln Ser Thr
1               5

(2) INFORMATION FOR SEQ ID NO:29:

(i) SEQUENCE CHARACTERISTICS:
        (A) LENGTH: 5 amino acids
        (B) TYPE: amino acid
        (D) TOPOLOGY: linear (ii) MOLECULE TYPE: peptide (xi) SEQUENCE DESCRIPTION: SEQ ID NO:29:

Gly Asp Gln Arg Leu
1               5

(2) INFORMATION FOR SEQ ID NO:30:

(i) SEQUENCE CHARACTERISTICS:
        (A) LENGTH: 28 base pairs
        (B) TYPE: nucleic acid
        (C) STRANDEDNESS: single
        (D) TOPOLOGY: linear (ii) MOLECULE TYPE: DNA
```

(xi) SEQUENCE DESCRIPTION: SEQ ID NO:30:

ACCGAATTCG TTTCTGGGCG ACCTTCAG                                              28

(2) INFORMATION FOR SEQ ID NO:31:

(i) SEQUENCE CHARACTERISTICS:
        (A) LENGTH: 27 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:31:

TGGAATTCGC TCACGGAAAG TTCGGAT                                               27

(2) INFORMATION FOR SEQ ID NO:32:

(i) SEQUENCE CHARACTERISTICS:
        (A) LENGTH: 28 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:32:

GCGAATTCGG GTAGAGCTAG TGCCTCTG                                              28

(2) INFORMATION FOR SEQ ID NO:33:

(i) SEQUENCE CHARACTERISTICS:
        (A) LENGTH: 27 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:33:

TGGAATTCGA AACGTGCGGA GCTGTCT                                               27

(2) INFORMATION FOR SEQ ID NO:34:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:34:

CTGCCCCTGA ATCACCCTCG A                                                     21

(2) INFORMATION FOR SEQ ID NO:35:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:35:

GTAAAACGAC GGCCAGT                                                          17

(2) INFORMATION FOR SEQ ID NO:36:

(i) SEQUENCE CHARACTERISTICS:
        (A) LENGTH: 33 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:36:

CAGGTCCCGG TCATCATCAT CATCATCATT AAT                                    33

(2) INFORMATION FOR SEQ ID NO:37:

(i) SEQUENCE CHARACTERISTICS:
        (A) LENGTH: 40 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:37:

TAGATTAATG ATGATGATGA TGATGACCGG GACCTGAGCT                                40

(2) INFORMATION FOR SEQ ID NO:38:

(i) SEQUENCE CHARACTERISTICS:
        (A) LENGTH: 10 amino acids
        (B) TYPE: amino acid
        (D) TOPOLOGY: linear (ii) MOLECULE TYPE: peptide (xi) SEQUENCE DESCRIPTION: SEQ ID NO:38:

Val Leu Ser Ala Gly Gly Ser Leu Phe Val
  1               5                 10

(2) INFORMATION FOR SEQ ID NO:39:

(i) SEQUENCE CHARACTERISTICS:
        (A) LENGTH: 10 amino acids
        (B) TYPE: amino acid
        (D) TOPOLOGY: linear (ii) MOLECULE TYPE: peptide (xi) SEQUENCE DESCRIPTION: SEQ ID NO:39:

Leu Ser Ala Gly Gly Ser Leu Phe Val Asn
  1               5                 10

(2) INFORMATION FOR SEQ ID NO:40:

(i) SEQUENCE CHARACTERISTICS:
        (A) LENGTH: 33 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:40:

AGAGGGGAGG GGTGCTAGCT CCACCCGTTC TGG                                    33

(2) INFORMATION FOR SEQ ID NO:41:

-continued

```
    (i) SEQUENCE CHARACTERISTICS:
        (A) LENGTH: 27 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:41:

GAGCGTGTGG AGCTAGCACC CCTGCCT                                       27

(2) INFORMATION FOR SEQ ID NO:42:

(i) SEQUENCE CHARACTERISTICS:
        (A) LENGTH: 27 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:42:

GGGGGAGTCG CTAGCAGGAC AAAGGTC                                       27

(2) INFORMATION FOR SEQ ID NO:43:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:43:

CGAACCTTTG TCCTGCTAGC GACCCCCCCG CGCCTC                             36

(2) INFORMATION FOR SEQ ID NO:44:

(i) SEQUENCE CHARACTERISTICS:
        (A) LENGTH: 39 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:44:

TGAGACCTCT GGCTTCCTTA AGATCACGTT GGGCGCCGG                          39

(2) INFORMATION FOR SEQ ID NO:45:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:45:

GACCCATTGT GAACTTAAGC GAGCCCACCG                                    30
```